(12) United States Patent
Zhang et al.

(10) Patent No.: US 8,852,599 B2
(45) Date of Patent: Oct. 7, 2014

(54) IMMUNOCONJUGATES, COMPOSITIONS FOR MAKING THEM, AND METHODS OF MAKING AND USE

(75) Inventors: Qian Zhang, Danville, CA (US); Sanjeev Gangwar, Foster City, CA (US); Chin Pan, Los Altos, CA (US); Daniel W. Derwin, San Francisco, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/477,219

(22) Filed: May 22, 2012

(65) Prior Publication Data

US 2012/0301490 A1    Nov. 29, 2012

Related U.S. Application Data

(60) Provisional application No. 61/490,117, filed on May 26, 2011.

(51) Int. Cl.
| | | |
|---|---|---|
| A61K 39/395 | (2006.01) | |
| C07K 7/06 | (2006.01) | |
| C07K 5/08 | (2006.01) | |
| C07K 16/18 | (2006.01) | |
| C07F 9/572 | (2006.01) | |
| A61P 35/00 | (2006.01) | |
| C07K 5/10 | (2006.01) | |
| A61K 47/48 | (2006.01) | |
| C07D 403/06 | (2006.01) | |
| C07D 403/14 | (2006.01) | |
| C07D 209/60 | (2006.01) | |

(52) U.S. Cl.
CPC ..... *A61K 47/48615* (2013.01); *A61K 47/48569* (2013.01); *A61K 47/48592* (2013.01); *A61K 47/48384* (2013.01); *C07D 403/06* (2013.01); *A61K 47/486* (2013.01); *C07D 403/14* (2013.01); *A61K 47/48638* (2013.01); *C07D 209/60* (2013.01)
USPC ..... 424/181.1; 530/330; 530/331; 530/391.7; 548/414

(58) Field of Classification Search
CPC .......... A61K 47/48384; A61K 47/48569; A61K 47/48592; A61K 47/486; A61K 47/48615; A61K 47/48638; C07D 209/60; C07D 403/06; C07D 403/14
USPC ........ 530/330, 331, 391.7; 548/414; 424/181.1
See application file for complete search history.

(56) References Cited

U.S. PATENT DOCUMENTS

| | | | |
|---|---|---|---|
| 5,595,756 A * | 1/1997 | Bally et al. | 424/450 |
| 5,659,022 A | 8/1997 | Kutyavin et al. | |
| 5,686,072 A * | 11/1997 | Uhr et al. | 424/183.1 |
| 6,989,452 B2 | 1/2006 | Ng et al. | |
| 7,129,261 B2 | 10/2006 | Ng et al. | |
| 7,498,302 B2 | 3/2009 | Ng et al. | |
| 7,507,420 B2 | 3/2009 | Ng et al. | |
| 7,517,903 B2 | 4/2009 | Chen et al. | |
| 7,655,660 B2 | 2/2010 | Zhao et al. | |
| RE41,252 E | 4/2010 | Ng et al. | |
| 7,691,962 B2 | 4/2010 | Boyd et al. | |
| 7,875,278 B2 | 1/2011 | Cardarelli et al. | |
| 7,968,586 B2 | 6/2011 | Gangwar et al. | |
| 8,097,703 B2 | 1/2012 | Rao-Naik et al. | |
| 8,124,738 B2 | 2/2012 | Terret et al. | |
| 2008/0279868 A1 | 11/2008 | Boyd et al. | |
| 2009/0074660 A1 | 3/2009 | Korman et al. | |
| 2009/0297438 A1 | 12/2009 | Huang et al. | |
| 2010/0034826 A1 | 2/2010 | Terrett et al. | |
| 2010/0104509 A1 | 4/2010 | King et al. | |
| 2010/0113476 A1 | 5/2010 | Chen et al. | |
| 2010/0143368 A1 | 6/2010 | King et al. | |
| 2010/0145036 A1 | 6/2010 | Sufi et al. | |
| 2010/0150950 A1 | 6/2010 | Coccia et al. | |
| 2010/0209432 A1 | 8/2010 | Terrette et al. | |

(Continued)

FOREIGN PATENT DOCUMENTS

| | | |
|---|---|---|
| WO | WO 91/16324 | 10/1991 |
| WO | WO 02/096910 | 12/2002 |

(Continued)

OTHER PUBLICATIONS

Michael B. Sporn, Chemoprevention of cancer,2000, Carcinogenesis, vol. 21 No. 3, pp. 535-530.*

(Continued)

*Primary Examiner* — Julie Ha
*Assistant Examiner* — Erinne Dabkowski
(74) *Attorney, Agent, or Firm* — Yuan Chao

(57) ABSTRACT

An immunoconjugate in which a phosphate-prodrugged DNA minor groove binding agent of formula (I), where X is a nucleophilically displaceable leaving group, is conjugated to an antibody or an antigen binding fragment of an antibody, and compounds that can be used for making such immunoconjugates, and uses of such immunoconjugates.

(I)

20 Claims, 30 Drawing Sheets

(56) References Cited

U.S. PATENT DOCUMENTS

| | | |
|---|---|---|
| 2011/0020329 A1 | 1/2011 | King et al. |
| 2011/0085970 A1 | 4/2011 | Terrett et al. |
| 2011/0262448 A1 | 10/2011 | Terrett et al. |
| 2012/0027782 A1 | 2/2012 | Terrett et al. |

FOREIGN PATENT DOCUMENTS

| | | | |
|---|---|---|---|
| WO | WO 03/000201 | | 1/2003 |
| WO | WO 03/086318 A2 | | 10/2003 |
| WO | WO 2007/089149 A2 | | 8/2007 |
| WO | WO2008074004 | * | 6/2008 .............. C12P 21/08 |
| WO | WO 2009045957 A1 | * | 4/2009 .............. A61K 39/00 |
| WO | WO 2009/073524 A2 | | 6/2009 |
| WO | WO 2009/073533 A2 | | 6/2009 |
| WO | WO 2009/073546 A2 | | 6/2009 |

OTHER PUBLICATIONS

Trisha Gura, Systems for Identifying New Drugs are Often Faulty, 1997, Science, vol. 278 No. 5340, pp. 1041-1042.*
Robert Auerbach, Angiogenesis assays: Problems and Pitfalls, 2000, Cancer and Metastasis Reviews, vol. 19, pp. 167-172.*
Stephen Neidle, Cancer Drug Design and Discovery, 2008, Elsevier/Academic Press, pp. 427-431.*
Rakesh K. Jain, Barriers to Drug Delivery in Solid Tumors, 1994, Scientific Journal, pp. 58-65.*
Takahiro Ishiguro, Anti-Glypican 3 Antibody as a potential antitumor agent for human liver cancer, Cancer Research, 2008; 68:9832-9838.*
Jihua Liu, Biorecognition and Subcellular Trafficking of HPMA Copolymer-Anti-PSMA Antibody Conjugates by Prostate Cancer Cells, Molecular Pharmaceutics, 2009; vol. 6, pp. 959-970.*
Best, M.D., "Click Chemistry and Bioorthogonal Reactions: Unprecedented Selectivity in the Labeling of Biological Molecules", Biochemistry, vol. 48, No. 28, pp. 6571-6584 (2009).
Boger, D.L. et al., "CBI Prodrug Analogs of CC-1065 and the Duocarmycins", Synthesis, No. SI, pp. 1505-1509 (1999).
Cacciari, B. et al., "CC-1065 and the duocarmycins: recent developments", Expert Opinion on Therapeutic Patents, vol. 10, No. 12, pp. 1853-1871 (2000).
Dubowchik, G.M. et al., "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity", Bioconjugate Chem., vol. 13, No. 4, pp. 855-869 (2002).
Kobayashi, E. et al., "Characteristics of Antitumor Activity of KW-2189, a Novel Water-Soluble Derivative of Duocarmycin, Against Murine and Human Tumors", Cancer Research, vol. 54, pp. 2404-2410 (1994).
Suckling, C.J., "Minor groove binders 1998-2004", Expert Opin. Ther. Patents., vol. 14, No. 12, pp. 1693-1724 (2004).
Zhao, R.Y. et al., Poster 45: "An improved synthesis of CC-1065 analogs and development of prodrugs", 28th National Medicinal Chemistry Symposium (San Diego, CA, Jun. 8-12, 2002) (Abstract) [2002a].
Zhao, R.Y. et al., Poster MEDI 147: "New water-soluble CC-1065 analog prodrugs: Design, synthesis and evaluation", 224th National Meeting of the American Chemical Society (Boston, MA, Aug. 18-22, 2002) (Abstract) [2002b].
Asai et al., "Synthesis and antitumor activity of water-soluble duocarmycin B1 prodrugs," Bioorg. Med. Chem. Lett. 1999, 9 (20), 2995-2998.
Boger et al., "1,2,9,9a-Tetrahydrocyclopropa[c]benz[e]-indol-4-one (CBI) analogs of CC-1065 and the duocarmycins: synthesis and evaluation," Bioorg. Med. Chem. 1995, 3(11), 1429-1453.
Denny et al., "Prodrug strategies in cancer therapy," Eur. J. Med. Chem., 2001, 36 (7-8), 577-595.
Denny et al., "Tumor-activated Prodrugs—a New Approach to Cancer Therapy," Cancer Investigation 2004, 22 (4), 604-619.
Warpehoski et al., "Stereoelectronic Factors Influencing the Biological Activity and DNA Interaction of Synthetic Antitumor Agents Modeled on CC-1065," J. Med. Chem. 1988, 31, 590-603.
International Search Report and Written Opinion for counterpart patent application No. PCT/US2012/039312, Nov. 13, 2012.

* cited by examiner

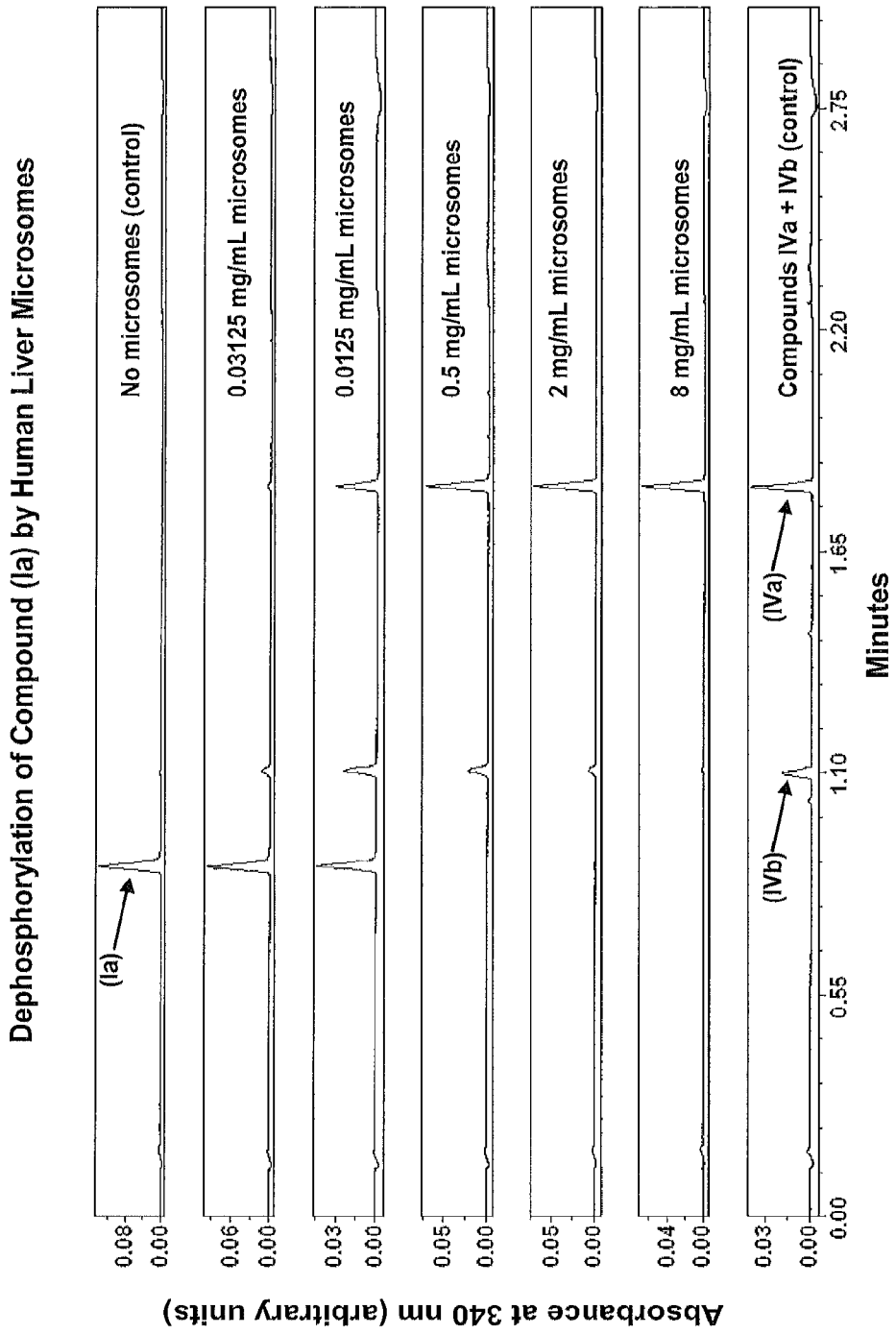

SEQUENCE LISTING

```
<160> NUMBER OF SEQ ID NOS: 60

<210> SEQ ID NO 1
<211> LENGTH: 5
<212> TYPE: PRT
<213> ORGANISM: Homo sapiens

<400> SEQUENCE: 1

Ser Tyr Ile Met His
1               5

<210> SEQ ID NO 2
<211> LENGTH: 17
<212> TYPE: PRT
<213> ORGANISM: Homo sapiens

<400> SEQUENCE: 2

Val Ile Ser Tyr Asp Gly Arg Asn Lys Tyr Tyr Ala Asp Ser Val Lys
1               5                   10                  15

Gly

<210> SEQ ID NO 3
<211> LENGTH: 9
<212> TYPE: PRT
<213> ORGANISM: Homo sapiens

<400> SEQUENCE: 3

Asp Thr Asp Gly Tyr Asp Phe Asp Tyr
1               5

<210> SEQ ID NO 4
<211> LENGTH: 11
<212> TYPE: PRT
<213> ORGANISM: Homo sapiens

<400> SEQUENCE: 4

Arg Ala Ser Gln Ser Val Ser Ser Tyr Leu Ala
1               5                   10

<210> SEQ ID NO 5
<211> LENGTH: 7
```

```
<212> TYPE: PRT
<213> ORGANISM: Homo sapiens

<400> SEQUENCE: 5

Asp Ala Ser Asn Arg Ala Thr
1               5

<210> SEQ ID NO 6
<211> LENGTH: 9
<212> TYPE: PRT
<213> ORGANISM: Homo sapiens

<400> SEQUENCE: 6

Gln Gln Arg Thr Asn Trp Pro Leu Thr
1               5

<210> SEQ ID NO 7
<211> LENGTH: 5
<212> TYPE: PRT
<213> ORGANISM: Homo sapiens

<400> SEQUENCE: 7

Ile Tyr Gly Met His
1               5

<210> SEQ ID NO 8
<211> LENGTH: 17
<212> TYPE: PRT
<213> ORGANISM: Homo sapiens

<400> SEQUENCE: 8

Val Leu Trp Tyr Asp Gly Ser His Glu Tyr Tyr Ala Asp Ser Val Lys
1               5                   10                  15
Gly

<210> SEQ ID NO 9
<211> LENGTH: 13
<212> TYPE: PRT
<213> ORGANISM: Homo sapiens

<400> SEQUENCE: 9

Asp Gly Asp Tyr Tyr Asp Ser Gly Ser Pro Leu Asp Tyr
1               5                   10

<210> SEQ ID NO 10
<211> LENGTH: 11
<212> TYPE: PRT
<213> ORGANISM: Homo sapiens

<400> SEQUENCE: 10

Arg Ala Ser Gln Ser Val Ser Ser Tyr Leu Ala
1               5                   10

<210> SEQ ID NO 11
<211> LENGTH: 7
<212> TYPE: PRT
<213> ORGANISM: Homo sapiens

<400> SEQUENCE: 11

Asp Ala Ser Asn Arg Ala Thr
1               5

<210> SEQ ID NO 12
<211> LENGTH: 9
```

```
<212> TYPE: PRT
<213> ORGANISM: Homo sapiens

<400> SEQUENCE: 12

Gln Gln Arg Ser Asn Trp Pro Leu Thr
1               5

<210> SEQ ID NO 13
<211> LENGTH: 5
<212> TYPE: PRT
<213> ORGANISM: Homo sapiens

<400> SEQUENCE: 13

Ser Ser Trp Ile Gly
1               5

<210> SEQ ID NO 14
<211> LENGTH: 17
<212> TYPE: PRT
<213> ORGANISM: Homo sapiens

<400> SEQUENCE: 14

Ile Ile Tyr Pro Asp Asp Ser Asp Thr Arg Tyr Ser Pro Ser Phe Gln
1               5                   10                  15

Gly

<210> SEQ ID NO 15
<211> LENGTH: 12
<212> TYPE: PRT
<213> ORGANISM: Homo sapiens

<400> SEQUENCE: 15

His Val Thr Met Ile Trp Gly Val Ile Ile Asp Phe
1               5                   10

<210> SEQ ID NO 16
<211> LENGTH: 11
<212> TYPE: PRT
<213> ORGANISM: Homo sapiens

<400> SEQUENCE: 16

Arg Ala Ser Gln Gly Ile Ser Ser Ala Leu Ala
1               5                   10

<210> SEQ ID NO 17
<211> LENGTH: 7
<212> TYPE: PRT
<213> ORGANISM: Homo sapiens

<400> SEQUENCE: 17

Asp Ala Ser Ser Leu Glu Ser
1               5

<210> SEQ ID NO 18
<211> LENGTH: 9
<212> TYPE: PRT
<213> ORGANISM: Homo sapiens

<400> SEQUENCE: 18

Gln Gln Phe Asn Ser Tyr Pro Tyr Thr
1               5

<210> SEQ ID NO 19
<211> LENGTH: 5
```

```
<212> TYPE: PRT
<213> ORGANISM: Homo sapiens

<400> SEQUENCE: 19

Ser Asn Trp Ile Gly
1               5

<210> SEQ ID NO 20
<211> LENGTH: 17
<212> TYPE: PRT
<213> ORGANISM: Homo sapiens

<400> SEQUENCE: 20

Ile Ile Tyr Pro Gly Asp Ser Asp Thr Arg Tyr Ser Pro Ser Phe Gln
1               5                  10                  15

Gly

<210> SEQ ID NO 21
<211> LENGTH: 10
<212> TYPE: PRT
<213> ORGANISM: Homo sapiens

<400> SEQUENCE: 21

Gln Thr Gly Phe Leu Trp Ser Ser Asp Leu
1               5                  10

<210> SEQ ID NO 22
<211> LENGTH: 11
<212> TYPE: PRT
<213> ORGANISM: Homo sapiens

<400> SEQUENCE: 22

Arg Ala Ser Gln Asp Ile Ser Ser Ala Leu Ala
1               5                  10

<210> SEQ ID NO 23
<211> LENGTH: 7
<212> TYPE: PRT
<213> ORGANISM: Homo sapiens

<400> SEQUENCE: 23

Asp Ala Ser Ser Leu Glu Ser
1               5

<210> SEQ ID NO 24
<211> LENGTH: 9
<212> TYPE: PRT
<213> ORGANISM: Homo sapiens

<400> SEQUENCE: 24

Gln Gln Phe Asn Ser Tyr Pro Leu Thr
1               5

<210> SEQ ID NO 25
<211> LENGTH: 5
<212> TYPE: PRT
<213> ORGANISM: Homo sapiens

<400> SEQUENCE: 25

Ser Tyr Trp Ile Ala
1               5

<210> SEQ ID NO 26
<211> LENGTH: 17
```

```
<212> TYPE: PRT
<213> ORGANISM: Homo sapiens

<400> SEQUENCE: 26

Ile Ile Phe Pro Gly Asp Ser Asp Thr Arg Tyr Ser Pro Ser Phe Gln
1               5                   10                  15
Gly

<210> SEQ ID NO 27
<211> LENGTH: 8
<212> TYPE: PRT
<213> ORGANISM: Homo sapiens

<400> SEQUENCE: 27

Thr Arg Glu Gly Tyr Phe Asp Tyr
1               5

<210> SEQ ID NO 28
<211> LENGTH: 12
<212> TYPE: PRT
<213> ORGANISM: Homo sapiens

<400> SEQUENCE: 28

Arg Ala Val Gln Ser Val Ser Ser Ser Tyr Leu Ala
1               5                   10

<210> SEQ ID NO 29
<211> LENGTH: 7
<212> TYPE: PRT
<213> ORGANISM: Homo sapiens

<400> SEQUENCE: 29

Gly Ala Ser Ser Arg Ala Thr
1               5

<210> SEQ ID NO 30
<211> LENGTH: 8
<212> TYPE: PRT
<213> ORGANISM: Homo sapiens

<400> SEQUENCE: 30

Gln Gln Tyr Gly Ser Ser Pro Thr
1               5

<210> SEQ ID NO 31
<211> LENGTH: 6
<212> TYPE: PRT
<213> ORGANISM: Homo sapiens

<400> SEQUENCE: 31

Ser Asn Tyr Met Asn Trp
1               5

<210> SEQ ID NO 32
<211> LENGTH: 16
<212> TYPE: PRT
<213> ORGANISM: Homo sapiens

<400> SEQUENCE: 32

Val Ile Tyr Gly Ser Gly Arg Thr Tyr Tyr Ala Asp Ser Val Lys Gly
1               5                   10                  15

<210> SEQ ID NO 33
<211> LENGTH: 7
```

```
<212> TYPE: PRT
<213> ORGANISM: Homo sapiens

<400> SEQUENCE: 33

Asp Thr Tyr Ala Met Asp Val
1               5

<210> SEQ ID NO 34
<211> LENGTH: 12
<212> TYPE: PRT
<213> ORGANISM: Homo sapiens

<400> SEQUENCE: 34

Arg Ala Ser Gln Ser Val Ser Ser Ser Tyr Leu Ala
1               5                   10

<210> SEQ ID NO 35
<211> LENGTH: 7
<212> TYPE: PRT
<213> ORGANISM: Homo sapiens

<400> SEQUENCE: 35

Gly Ala Ser Ser Arg Ala Thr
1               5

<210> SEQ ID NO 36
<211> LENGTH: 10
<212> TYPE: PRT
<213> ORGANISM: Homo sapiens

<400> SEQUENCE: 36

Gln Gln Tyr Gly Ser Ser Pro Met Tyr Thr
1               5                   10

<210> SEQ ID NO 37
<211> LENGTH: 5
<212> TYPE: PRT
<213> ORGANISM: Homo sapiens

<400> SEQUENCE: 37

Ser Tyr Val Met His
1               5

<210> SEQ ID NO 38
<211> LENGTH: 16
<212> TYPE: PRT
<213> ORGANISM: Homo sapiens

<400> SEQUENCE: 38

Val Ile Gly Thr Gly Gly Val Thr His Tyr Ala Asp Ser Val Lys Gly
1               5                   10                  15

<210> SEQ ID NO 39
<211> LENGTH: 16
<212> TYPE: PRT
<213> ORGANISM: Homo sapiens

<400> SEQUENCE: 39

Trp Gly Tyr Tyr Gly Ser Gly Ser Tyr Glu Asn Asp Ala Phe Asp Ile
1               5                   10                  15

<210> SEQ ID NO 40
<211> LENGTH: 12
<212> TYPE: PRT
<213> ORGANISM: Homo sapiens
```

```
<400> SEQUENCE: 40

Arg Ala Ser Gln Ser Val Ser Ser Ser Tyr Leu Ala
1               5                   10

<210> SEQ ID NO 41
<211> LENGTH: 7
<212> TYPE: PRT
<213> ORGANISM: Homo sapiens

<400> SEQUENCE: 41

Gly Ala Ser Ser Arg Ala Thr
1               5

<210> SEQ ID NO 42
<211> LENGTH: 8
<212> TYPE: PRT
<213> ORGANISM: Homo sapiens

<400> SEQUENCE: 42

Gln Gln Tyr Ser Ser Ser Leu Thr
1               5

<210> SEQ ID NO 43
<211> LENGTH: 5
<212> TYPE: PRT
<213> ORGANISM: Homo sapiens

<400> SEQUENCE: 43

Ser Tyr Ala Met Asn
1               5

<210> SEQ ID NO 44
<211> LENGTH: 17
<212> TYPE: PRT
<213> ORGANISM: Homo sapiens

<400> SEQUENCE: 44

Trp Ile Asn Thr Asn Thr Gly Asn Pro Thr Tyr Ala Gln Gly Phe Thr
1               5                   10                  15

Gly

<210> SEQ ID NO 45
<211> LENGTH: 10
<212> TYPE: PRT
<213> ORGANISM: Homo sapiens

<400> SEQUENCE: 45

Leu Phe Tyr Tyr Tyr Phe Gly Met Asp Val
1               5                   10

<210> SEQ ID NO 46
<211> LENGTH: 14
<212> TYPE: PRT
<213> ORGANISM: Homo sapiens

<400> SEQUENCE: 46

Thr Gly Thr Ser Ser Asp Val Gly Ser Tyr Asn Leu Val Ser
1               5                   10

<210> SEQ ID NO 47
<211> LENGTH: 7
<212> TYPE: PRT
<213> ORGANISM: Homo sapiens
```

```
<400> SEQUENCE: 47

Glu Val Ser Lys Arg Pro Ser
1               5

<210> SEQ ID NO 48
<211> LENGTH: 10
<212> TYPE: PRT
<213> ORGANISM: Homo sapiens

<400> SEQUENCE: 48

Cys Ser Tyr Ala Asn Ser Ser Thr Leu Val
1               5                   10

<210> SEQ ID NO 49
<211> LENGTH: 5
<212> TYPE: PRT
<213> ORGANISM: Homo sapiens

<400> SEQUENCE: 49

Ser Tyr Ala Phe His
1               5

<210> SEQ ID NO 50
<211> LENGTH: 17
<212> TYPE: PRT
<213> ORGANISM: Homo sapiens

<400> SEQUENCE: 50

Val Ile Ser Tyr Asp Gly Ser Ile Lys Tyr Tyr Ala Asp Ser Val Lys
1               5                   10                  15

Gly

<210> SEQ ID NO 51
<211> LENGTH: 6
<212> TYPE: PRT
<213> ORGANISM: Homo sapiens

<400> SEQUENCE: 51

Thr Tyr Tyr Phe Asp Tyr
1               5

<210> SEQ ID NO 52
<211> LENGTH: 11
<212> TYPE: PRT
<213> ORGANISM: Homo sapiens

<400> SEQUENCE: 52

Arg Ala Ser Gln Ser Ile Gly Ser Ser Leu His
1               5                   10

<210> SEQ ID NO 53
<211> LENGTH: 7
<212> TYPE: PRT
<213> ORGANISM: Homo sapiens

<400> SEQUENCE: 53

Tyr Ala Ser Gln Ser Phe Ser
1               5

<210> SEQ ID NO 54
<211> LENGTH: 9
<212> TYPE: PRT
<213> ORGANISM: Homo sapiens
```

```
<400> SEQUENCE: 54

His Gln Ser Ser Ser Leu Pro Ile Thr
1               5

<210> SEQ ID NO 55
<211> LENGTH: 5
<212> TYPE: PRT
<213> ORGANISM: Homo sapiens

<400> SEQUENCE: 55

Ile Tyr Ala Met Ser
1               5

<210> SEQ ID NO 56
<211> LENGTH: 17
<212> TYPE: PRT
<213> ORGANISM: Homo sapiens

<400> SEQUENCE: 56

Ala Ile Ser Asp Ser Gly Gly Arg Thr Tyr Phe Ala Asp Ser Val Arg
1               5                   10                  15

Gly

<210> SEQ ID NO 57
<211> LENGTH: 11
<212> TYPE: PRT
<213> ORGANISM: Homo sapiens

<400> SEQUENCE: 57

Val Asp Tyr Ser Asn Tyr Leu Phe Phe Asp Tyr
1               5                   10

<210> SEQ ID NO 58
<211> LENGTH: 12
<212> TYPE: PRT
<213> ORGANISM: Homo sapiens

<400> SEQUENCE: 58

Arg Ala Ser Gln Ser Ile Ser Ser Ser Tyr Leu Ala
1               5                   10

<210> SEQ ID NO 59
<211> LENGTH: 7
<212> TYPE: PRT
<213> ORGANISM: Homo sapiens

<400> SEQUENCE: 59

Gly Ala Ser Ser Arg Ala Thr
1               5

<210> SEQ ID NO 60
<211> LENGTH: 9
<212> TYPE: PRT
<213> ORGANISM: Homo sapiens

<400> SEQUENCE: 60

Gln Gln Tyr Gly Ser Ser Pro Tyr Thr
1               5
```

IMMUNOCONJUGATES, COMPOSITIONS FOR MAKING THEM, AND METHODS OF MAKING AND USE

CROSS-REFERENCE TO RELATED APPLICATIONS

This application claims the benefit under 35 U.S.C. §119 (e) of U.S. Provisional Application No. 61/490,117, filed May 26, 2011; the disclosure of which is incorporated herein by reference.

SEQUENCE LISTING

Incorporated herein by reference in its entirety is a Sequence Listing named "SEQT_11770USNP.txt", comprising SEQ ID NO:1 through SEQ ID NO:60, which include nucleic acid and/or amino acid sequences disclosed herein. The Sequence Listing has been submitted herewith in ASCII text format via EFS-Web, and thus constitutes both the paper and computer readable form thereof. The Sequence Listing was first created using PatentIn 3.5 on Apr. 27, 2012 and is 10 KB in size

BACKGROUND OF THE INVENTION

This invention relates to therapeutic immunoconjugates, compositions that can be utilized to make them, and methods of making and using such compositions and immunoconjugates.

The natural products CC-1065 and the duocarmycins are potent cytotoxic agents that bind to the minor groove of DNA. They are characterized by a fused cyclopropyl ring (dotted box in structures below) that is destabilized by conformational changes induced upon binding within the minor groove and reacts with a DNA adenine base in a ring-opening alkylation reaction. The damage to the DNA can be irreparable, leading to cell death.

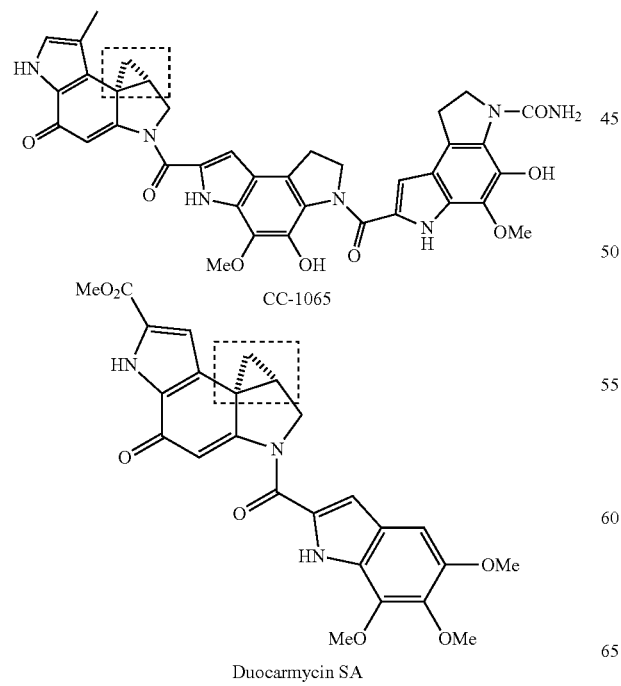

Duocarmycin SA

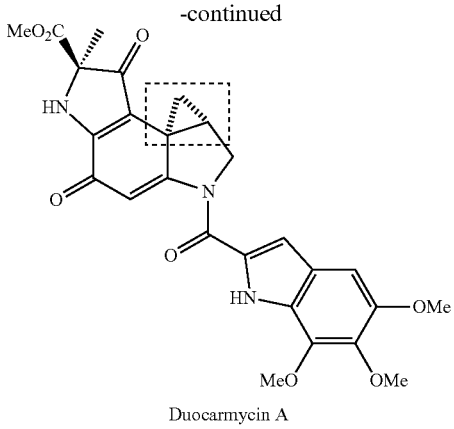

Duocarmycin A

The potency of these natural products has stimulated research aimed at developing analogs useful as anti-cancer drugs. See, e.g., Cacciari et al. 2000 and Suckling 2004. (Full citations of the documents cited herein by first author or inventor and year are listed at the end of this specification. Such listed documents are incorporated herein by reference.) The analogs have either the fused cyclopropyl pharmacophore or a ring-opened (seco) equivalent thereof, as shown in the structures below, where Ar represents an aromatic ring that typically is phenyl or pyrrole and X represents a leaving group such as Cl or Br. The seco form is convertible to the cyclopropyl form by the elimination of HX, a process that can occur either in vitro or in vivo.

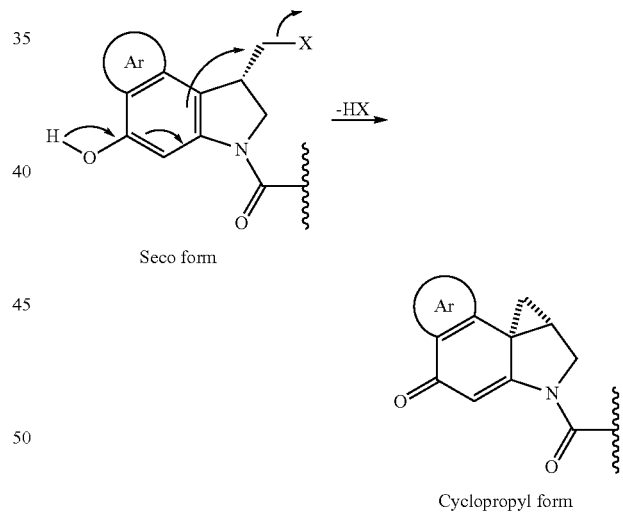

Hereinafter the term "minor groove binding agent" or "MGBA" will be used to refer to CC-1065/duocarmycin type compounds having the fused cyclopropyl ring or its seco form, although other types of DNA minor groove binding compounds are known.

Immunoconjugates represent an area of high current interest in anti-cancer therapy. In an immunoconjugate, a drug moiety is conjugated (covalently linked) to an antibody whose antigen is uniquely expressed or overexpressed by a cancer cell ("tumor associated antigen"). In binding to its antigen, the antibody functions as a targeting agent for delivering the drug moiety to the cancer cell with high specificity. The antigen can be a protein on the surface of the cancer cell.

Upon binding of the antibody to the antigen, the antigen-immunoconjugate complex is internalized and eventually finds its way inside a vesicular body such as a lysosome, where the covalent linker between the drug moiety and the antibody is cleaved, liberating the drug moiety to exert its cytotoxic effect. Alternatively, the tumor associated antigen can be one that is secreted by tumor cells into the vicinal extracellular space.

Advantageously, the covalent linker is designed such that cleavage is effected by a factor prevalent inside a lysosome but not in plasma. One such factor is the lower lysosomal pH, so that the covalent linker can be an acid-sensitive group such as a hydrazone. Another such factor is the generally higher intracellular concentration of glutathione, allowing for the cleavage of disulfide covalent linkers by a disulfide exchange mechanism. Yet another such factor is the presence of lysosomal enzymes such as cathepsin B, which can cleave peptidyl linkers designed to be preferred substrates (Dubowchik et al. 2002).

Their potency makes MGBAs attractive candidates for the drug moiety in an immunoconjugate. Illustrative disclosures relating to MGBAs and their use in immunoconjugates include: Boyd et al. 2008 and 2010; Chen et al. 2010; Gangwar et al. 2008; Ng et al. 2002, 2006a, 2006b, 2009a, 2009b, and 2010; and Sufi et al. 2010.

There exists the possibility of adventitious cleavage of the covalent linker while the immunoconjugate is still in general circulation and has not yet been delivered to the target cancer cell, resulting in the premature release of the drug moiety and posing the risk of systemic toxicity. Such risk is of particular concern where the drug moiety is a highly potent cytotoxin such as an MGBA. However, where an immunoconjugate employs a seco-MGBA, the risk can be reduced by derivatizing the phenolic hydroxyl group to block conversion to the cyclopropyl form. Then, in the event of adventitious cleavage, what is released is an inactive derivatized seco-MGBA. By selecting a derivative that is cleaved inside a lysosome, the derivative functions as a prodrugging group and provides a safety factor: two cleavages, of the linker and of the prodrugging group, must occur before active cytotoxin is released.

One such prodrugging group is a carbamate, which can be cleaved by lysosomal and/or cytosolic carboxyesterase as shown below. ($R^a$ and $R^b$ represent generic radical groups.) For illustrative disclosures relating to seco-MGBA immunoconjugates prodrugged with a carbamate group, see Aristoff et al. 1991; Boger et al. 1999; Boyd et al. 2008 and 2010; Chen et al. 2010; Gangwar et al. 2008; Kobayashi 1994; Ng et al. 2002, 2006a, 2006b, 2009a, 2009b, and 2010; Sufi et al. 2010; and Zhao et al. 2010.

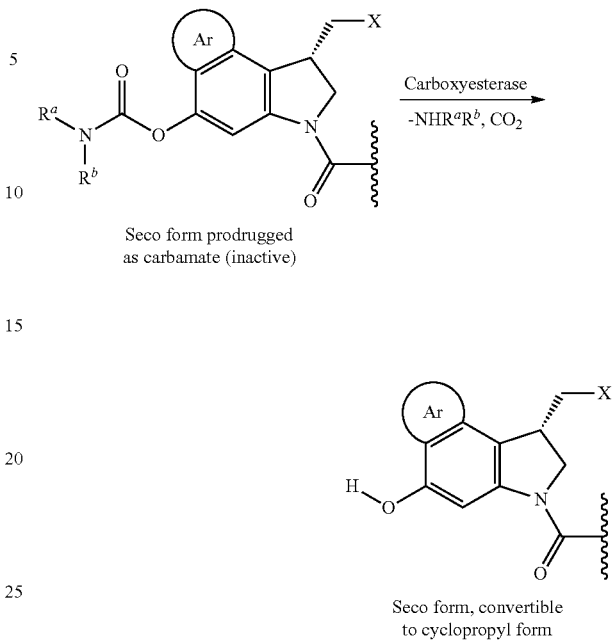

Seco form prodrugged as carbamate (inactive)

Seco form, convertible to cyclopropyl form

Another prodrugging group that can be used with seco-MGBAs is a phosphate, in which case the cleaving enzyme is a phosphatase, found inside lysosomes and/or in the cytosol. Illustrative disclosures relating to phosphate prodrugging groups in seco-MGBAs include Boyd et al. 2010, Chen et al. 2009, Glazier 2003, King et al. 2011, Kutyavin et al. 1997, Ng et al. 2002, Zhao et al. 2002a and 2002b, and Zhao et al. 2010.

An MGBA compound that has been extensively studied has the structure (A) (Boyd et al. 2008 and Sufi et al. 2010). It has a carbamate prodrugging group; a valine-citrulline (Val-Cit, recited in N-to-C direction, i.e., from the amino ($NH_2$) terminus to the carboxyl ($CO_2H$) terminus) dipeptide linker, designed to be cleaved by cathepsin B (Dubowchik et al. 2002); and a maleimide group, for immunoconjugation by the Michael addition of an antibody sulfhydryl group. An immunoconjugate of compound (A) and an anti-CD70 antibody has been undergoing clinical trials.

(A)

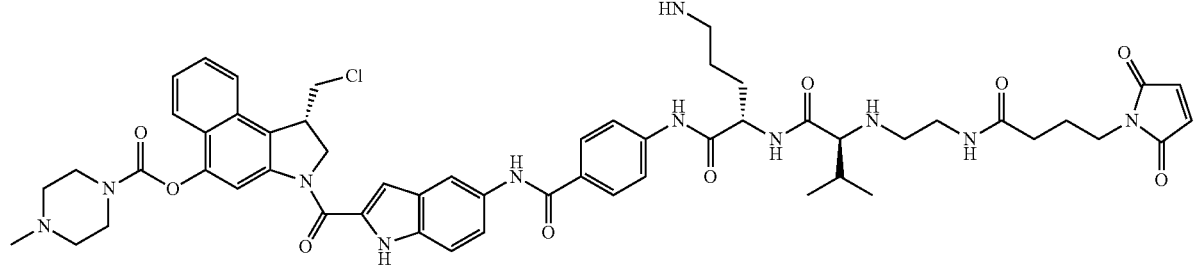

BRIEF SUMMARY OF THE INVENTION

We have observed that in some instances a carbamate-prodrugged seco-MGBA immunoconjugate such as one derived from compound (A) is not as potent an anti-cancer agent as might be desired. We hypothesize that the lower potency is attributable to insufficient carboxyesterase activity inside some types of cancer cells and consequent inefficient decarbamoylation. Thus, it is desirable to develop pro-drugged seco-MGBA immunoconjugates that are not dependent on carboxyesterase for their activation.

In one aspect, this invention provides an immunoconjugate comprising an antibody (or an antigen binding fragment thereof) and a phosphate-prodrugged seco-MGBA compound. The removal of the phosphate prodrugging group is independent of carboxyesterase activity within the target cell, thus avoiding the drawback noted above. Rather, compounds of this invention rely on phosphatase, which our experiments show to be present at sufficient levels across a range of human tumor cells. One embodiment is an immunoconjugate wherein a compound of the formula (I)

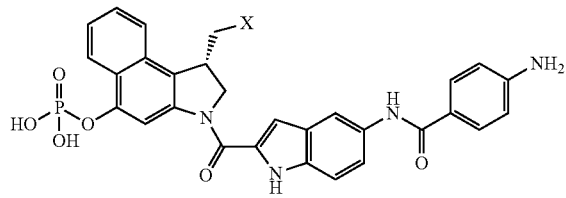

(I)

wherein X is a nucleophilically displaceable leaving group, or a pharmaceutically acceptable salt thereof, is conjugated at the —NH$_2$ group thereof via a peptidyl linker to an antibody or antigen binding fragment of such antibody. Preferably, the antibody is a human monoclonal antibody that recognizes a human antigen selected from the group consisting of CD70, mesothelin, PSMA, CD19, glypican-3, B7H4, RG-1, CD22, and PTK7.

In another aspect, there is provided a phosphate-prodrugged seco-MGBA compound adapted for conjugation to an antibody or antigen binding fragment thereof. Generally, such a compound comprises a phosphate-prodrugged seco-MGBA moity, an enzymatically cleavable peptidyl linker, a spacer moiety, and a reactive functional group for attachment to an antibody or antigen-binding fragment thereof. One embodiment is represented by a compound of formula (II)

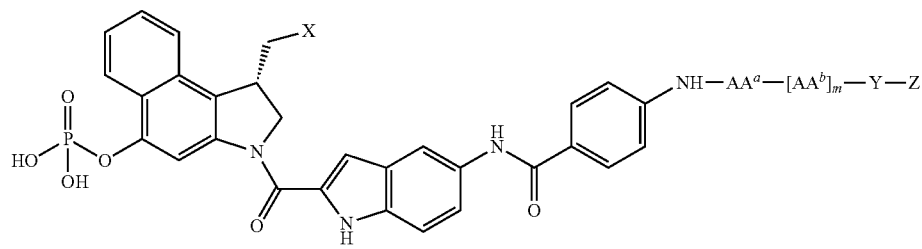

(II)

wherein
X is a nucleophilically displaceable leaving group;
AA$^a$ and each AA$^b$ are independently selected from the group consisting of alanine, β-alanine, γ-aminobutyric acid, arginine, asparagine, aspartic acid, γ-carboxyglutamic acid, citrulline, cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine;
M is 0, 1, 2, 3, 4, or 5;
Y is a spacer moiety; and
Z is a reactive functional group capable of conjugation to an antibody;
or a pharmaceutically acceptable salt thereof.

In another aspect, there is provided a phosphate prodrugged compound that can be used to prepare immunoconjugates, as embodied by a compound of formula (I):

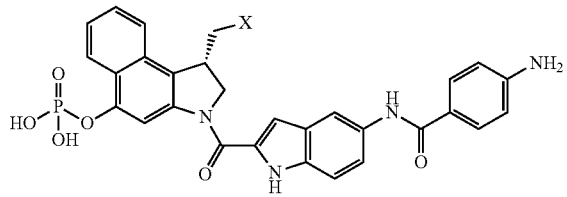

(I)

wherein X is a nucleophilically displaceable leaving group, or a pharmaceutically acceptable salt thereof. Compound (I) can be combined with a peptidyl linker, spacer, and reactive functional group as described above and then conjugated to an antibody or antigen-binding fragment thereof.

In yet another aspect, there is provided a method of treating a cancer in a subject—preferably a human—suffering from such cancer, comprising administering to the subject a therapeutically effective amount of an immunoconjugate of this invention. The cancer can be a cancer whose cells express an antigen selected from the group consisting of CD70, mesothelin, PSMA, CD19, glypican-3, B7H4, RG-1, CD22, and PTK7. Examples of cancers that can be so treated include renal cancer, pancreatic cancer, ovarian cancer, lymphoma, colon cancer, mesothelioma, gastric cancer, lung cancer, prostate cancer, adenocarcinoma, liver cancer, and breast cancer.

In yet another aspect, there is provided the use of an immunoconjugate of this invention for the preparation of a medicament for the treatment of cancer.

BRIEF DESCRIPTION OF THE DRAWING(S)

FIGS. 1A and 1B in combination show the synthesis of a compound of this invention, having a maleimide reactive functional group.

FIG. 2 shows the synthesis of another compound of this invention.

FIGS. 3A through 3D in combination show the synthesis of yet another compound of this invention.

FIGS. 4A through 4R compare the cell proliferation inhibitory properties of phosphate prodrugged immunoconjugates of this invention against those of carbamate prodrugged immunoconjugates, using a $^3$H thymidine incorporation proliferation assay. The test cell lines included the following human cancer cell lines: 786-O (renal carcinoma), prostate specific membrane antigen (PSMA), HPAC (pancreatic cancer), OVCAR3 (ovarian cancer), Ramos (Burkitt's lymphoma), H226 (mesothelioma), N87 (gastric cancer), H292 (mucoepidermoid pulmonary carcinoma), H1650 (adenocarcinoma), Hep 3b (hepatocellular carcinoma), Hep G2 (hepatocellular carcinoma), HCC-1954 (breast cancer), MDA-MB-468 (breast cancer), HCT116 (colon cancer) and H520 (lung cancer). Additionally, a mesothelin-expressing transfected CHO (Chinese hamster ovary) cell line was used.

FIG. 5 depicts chromatographic traces showing the dephosphorylation of a phosphate prodrugged compound of this invention by human liver microsome enzymes.

DETAILED DESCRIPTION OF THE INVENTION

Definitions

Figure 1A:
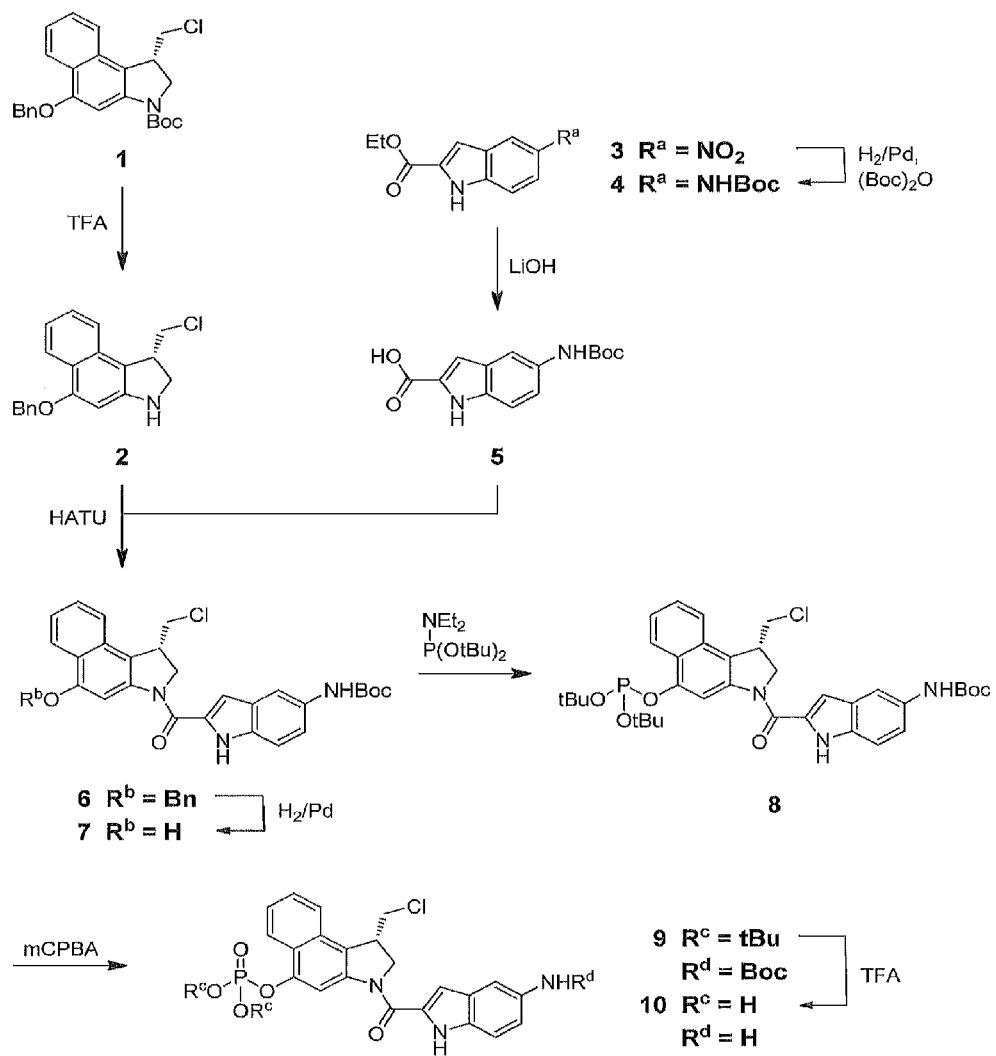

"Antibody" means whole antibodies and any antigen binding fragment (i.e., "antigen-binding portion") or single chains thereof. A whole antibody is a glycoprotein comprising at least two heavy (H) chains and two light (L) chains interconnected by disulfide bonds. Each heavy chain comprises a heavy chain variable region ($V_H$) and a heavy chain constant region comprising three domains, $C_{H1}$, $C_{H2}$ and $C_{H3}$. Each light chain comprises a light chain variable region ($V_L$ or $V_k$) and a light chain constant region comprising one single domain, $C_L$. The $V_H$ and $V_L$ regions can be further subdivided into regions of hypervariability, termed complementarity determining regions (CDRs), interspersed with more conserved framework regions (FRs). Each $V_H$ and $V_L$ comprises three CDRs and four FRs, arranged from amino- to carboxy-terminus in the following order: FR1, CDR1, FR2, CDR2, FR3, CDR3, and FR4. The variable regions contain a binding domain that interacts with an antigen. The constant regions may mediate the binding of the antibody to host tissues or factors, including various cells of the immune system (e.g., effector cells) and the first component (Clq) of the classical complement system. An antibody is said to "specifically bind" to an antigen X if the antibody binds to antigen X with a $K_D$ of $5\times10^{-8}$ M or less, more preferably $1\times10^{-8}$ M or less, more preferably $6\times10^{-9}$ M or less, more preferably $3\times10^{-9}$ M or less, even more preferably $2\times10^{-9}$ M or less. The antibody can be chimeric, humanized, or, preferably, human. The heavy chain constant region can be engineered to affect glycosylation type or extent, to extend antibody half-life, to enhance or reduce interactions with effector cells or the complement system, or to modulate some other property. The engineering can be accomplished by replacement, addition, or deletion of one or more amino acids or by replacement of a domain with a domain from another immunoglobulin type, or a combination of the foregoing.

"Antibody fragment" and "antigen-binding portion" of an antibody (or simply "antibody portion") mean one or more fragments of an antibody that retain the ability to specifically bind to an antigen. It has been shown that the antigen-binding function of an antibody can be performed by fragments of a full-length antibody, such as (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, for example, Abbas et al., *Cellular and Molecular Immunology*, 6th Ed., Saunders Elsevier 2007); (iv) an Fd fragment consisting of the $V_H$ and $C_{H1}$ domains; (v) an Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ regions pair to form monovalent molecules (known as single chain Fv, or scFv); see, e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" or "antigen-binding fragment" of an antibody.

An "isolated antibody" means an antibody that is substantially free of other antibodies having different antigenic specificities (e.g., an isolated antibody that specifically binds antigen X is substantially free of antibodies that specifically bind antigens other than antigen X). An isolated antibody that specifically binds antigen X may, however, have cross-reactivity to other antigens, such as antigen X molecules from other species. In certain embodiments, an isolated antibody specifically binds to human antigen X and does not cross-react with other (non-human) antigen X antigens. Moreover, an isolated antibody may be substantially free of other cellular material and/or chemicals.

"Monoclonal antibody" or "monoclonal antibody composition" means a preparation of antibody molecules of single molecular composition, which displays a single binding specificity and affinity for a particular epitope.

"Human antibody" means an antibody having variable regions in which both the framework and CDR regions (and the constant region, if present) are derived from human germline immunoglobulin sequences. Human antibodies may include later modifications, including natural or synthetic modifications. Human antibodies may include amino acid residues not encoded by human germline immunoglobulin sequences (e.g., mutations introduced by random or site-specific mutagenesis in vitro or by somatic mutation in vivo). However, "human antibody" does not include antibodies in which CDR sequences derived from the germline of another mammalian species, such as a mouse, have been grafted onto human framework sequences.

"Human monoclonal antibody" means an antibody displaying a single binding specificity, which has variable regions in which both the framework and CDR regions are derived from human germline immunoglobulin sequences. In one embodiment, human monoclonal antibodies are produced by a hybridoma that includes a B cell obtained from a transgenic nonhuman animal, e.g., a transgenic mouse, having a genome comprising a human heavy chain transgene and a light chain transgene fused to an immortalized cell.

Unless particular stereoisomers are specifically indicated (e.g., by a bolded or dashed bond at a relevant stereocenter in a structural formula, by depiction of a double bond as having E or Z configuration in a structural formula, or by use of stereochemistry-designating nomenclature), all stereoisomers are included within the scope of the invention, as pure compounds as well as mixtures thereof. Unless otherwise indicated, individual enantiomers, diastereomers, geometrical isomers, and combinations and mixtures thereof are all encompassed by the present invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Pharmaceutically acceptable salt" means a salt of a compound suitable for pharmaceutical formulation. Where a compound has one or more basic groups, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, lactobionate, suberate, tosylate, and the like. Where a compound has one or more acidic groups, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenylcyclohexylamine salt, benzathine salt, sodium salt, tetramethylammonium salt, and the like. Polymorphic crystalline forms and solvates are also encompassed within the scope of this invention. In respect of phosphate groups, specific examples of pharmaceutically acceptable salts include the sodium, potassium, and ammonium salts.

Compositions

In one aspect, a composition of this invention is an immunoconjugate wherein a compound of the formula (I)

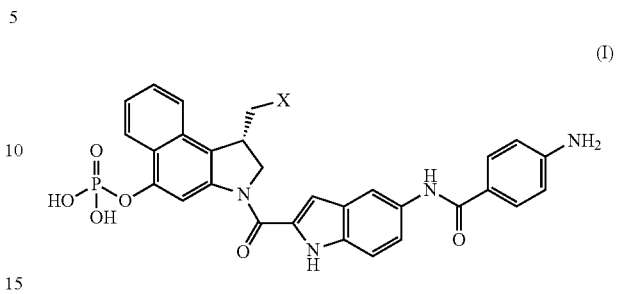

(I)

wherein X is a nucleophilically displaceable leaving group, or a pharmaceutically acceptable salt thereof, is conjugated via a peptidyl linker to an antibody or an antigen binding fragment thereof. The conjugation preferably is through the 4-$NH_2$ group thereof. The peptidyl linker preferably is a dipeptide selected from Val-Cit, Phe-Cit, Phe-Lys, Val-Lys, Val-Glu, Val-Asp, Val-Ser, and Val-Gly, each dipeptide being recited in the N-to-C direction.

In one embodiment, the immunoconjugate has a structure represented by formula (IIIa)

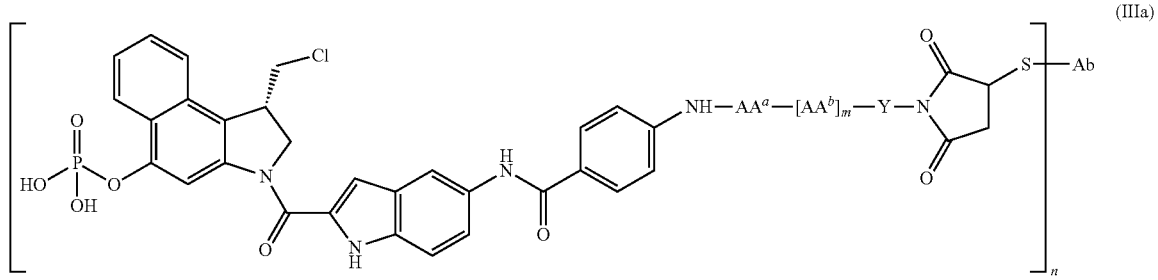

(IIIa)

where $AA^a$, $AA^b$, m, and Y are as defined hereinabove in respect of formula (II), Ab represents an antibody or an antigen-binding fragment of an antibody, and n is 1, 2, 3, 4, or 5; or a pharmaceutically acceptable salt thereof. Preferred embodiments and/or combinations of $AA^a$, $AA^b$, m, Y, Ab, and n are described hereinbelow.

A preferred immunoconjugate according to formula (IIIa) has a structure according to formula (IIIa')

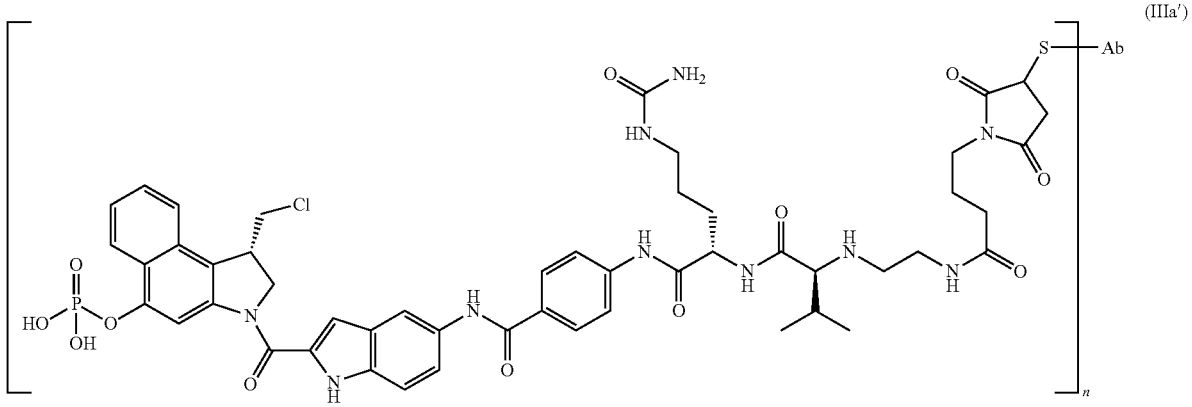

(IIIa')

where Ab and n are as defined above, or a pharmaceutically acceptable salt thereof. Thus, this embodiment has a Val-Cit dipeptide linker, with those skilled in the art understanding that in structural formula (IIIa') the dipeptide is drawn in a C-to-N orientation when read in a left to right direction.

In another embodiment, the immunoconjugate has a structure represented by formula (IIIb)

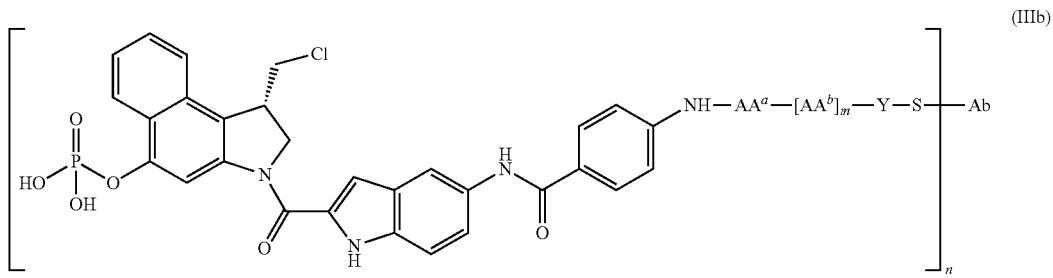

(IIIb)

where $AA^a$, $AA^b$, m, and Y are as defined hereinabove in respect of formula (II), Ab represents an antibody or an antigen-binding fragment of an antibody, and n is 1, 2, 3, 4, or 5; or a pharmaceutically acceptable salt thereof. Preferred embodiments and/or combinations of $AA^a$, $AA^b$, m, Y, Ab, and n are described hereinbelow.

A preferred immunoconjugate according to formula (IIIb) has a structure according to formula (IIIb')

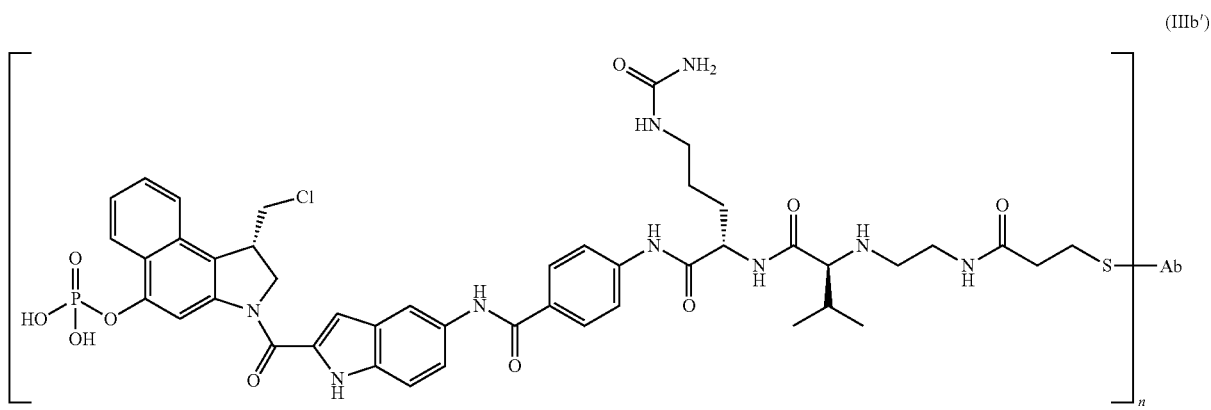

(IIIb')

where Ab and n are as defined above, or a pharmaceutically acceptable salt thereof.

As reflected by the subscript n in formulae (IIIa), (IIIa'), (IIIb), and (IIIb'), each antibody can conjugate with more than one prodrugged seco-MGBA moiety, depending on the number of sites the antibody has available for conjugation and the experimental conditions employed. Those skilled in the art will appreciate that, while each individual antibody is conjugated to an integer number of prodrugged moieties, an immunoconjugate preparation may assay for a non-integer ratio of prodrugged seco-MGBA moieties per antibody ("substitution ratio" or "SR"), reflecting a statistical average. SR preferably is between 1 and 5, more preferably between 2.5 and 3.5.

Another aspect of this invention is a compound adapted for conjugation to an antibody, represented by formula (II)

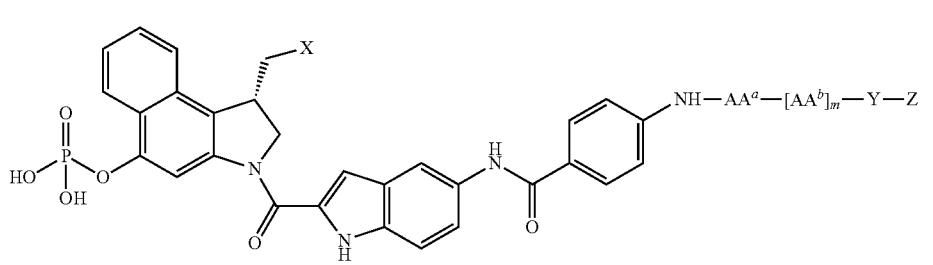

where $AA^a$, $AA^b$, m, Y, and Z are as previously defined, or a pharmaceutically acceptable salt thereof. Preferred embodiments and/or combinations of $AA^a$, $AA^b$, m, Y, and Z are described hereinbelow.

A preferred embodiment according to formula (II) has the structure of formula (IIa)

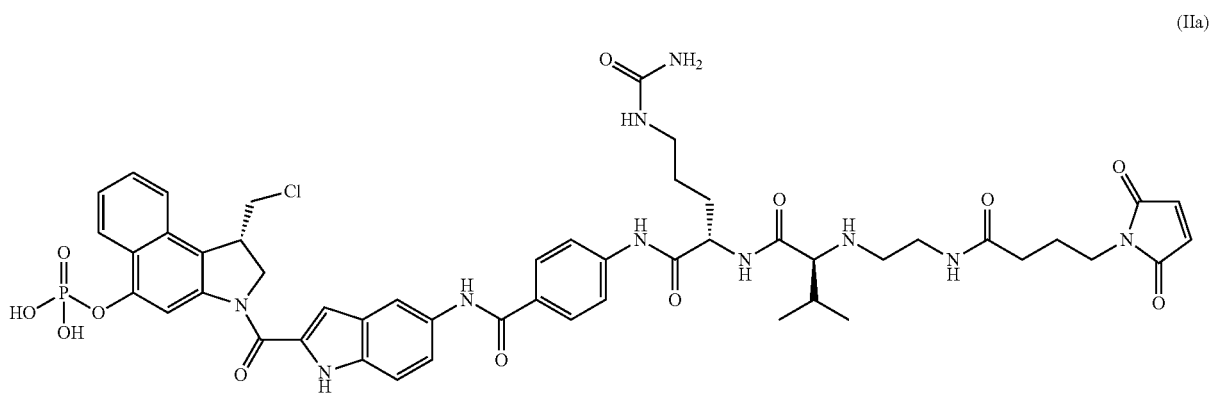 [SMILES: CC(C)[C@H](NCCNC(=O)CCCN1C(=O)C=CC1=O)C(=O)N[C@@H](CCCNC(N)=O)C(=O)Nc1ccc(C(=O)Nc2ccc3[nH]c(C(=O)N4C[C@@H](CCl)c5c4cc(OP(=O)(O)O)c4ccccc54)cc3c2)cc1]

or a pharmaceutically acceptable salt thereof.

Other preferred embodiments according to formula (II) have the structures of formulae (IIb)-(IIg):

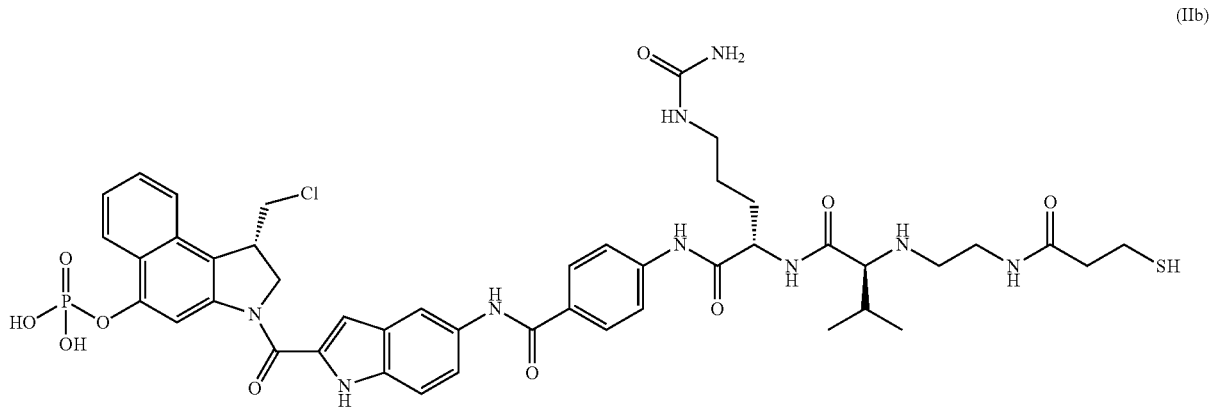

-continued
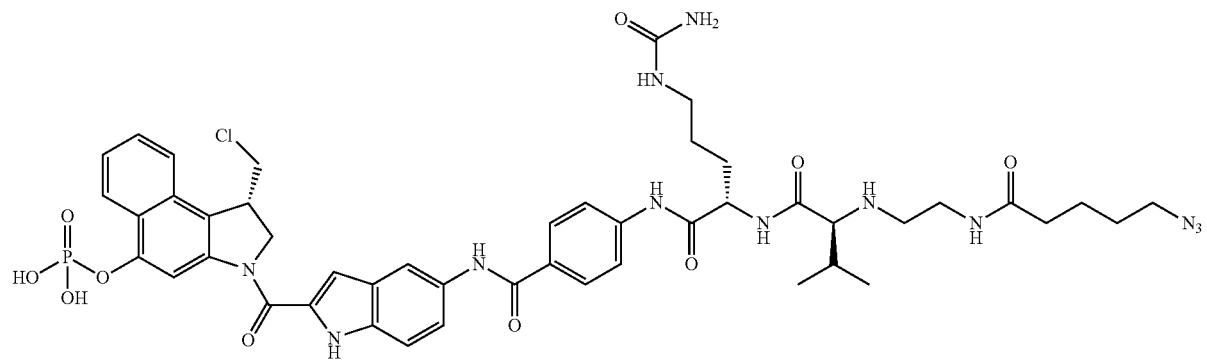
(IIc)
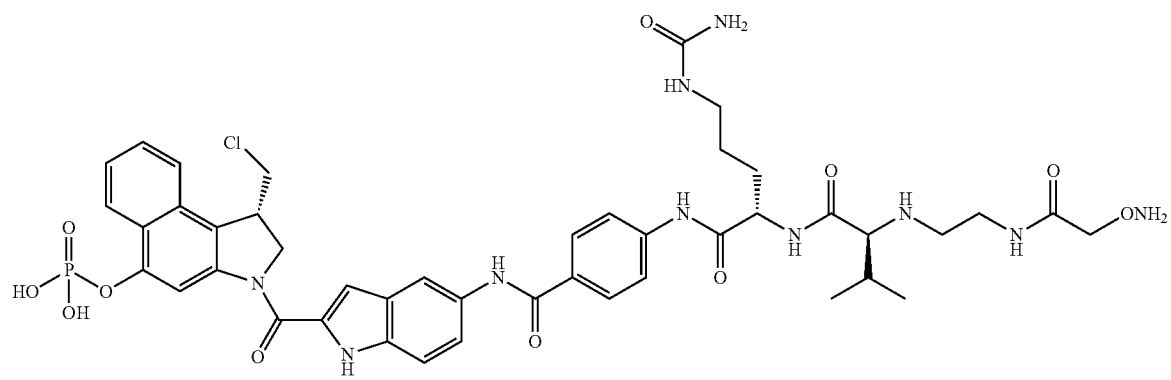
(IId)
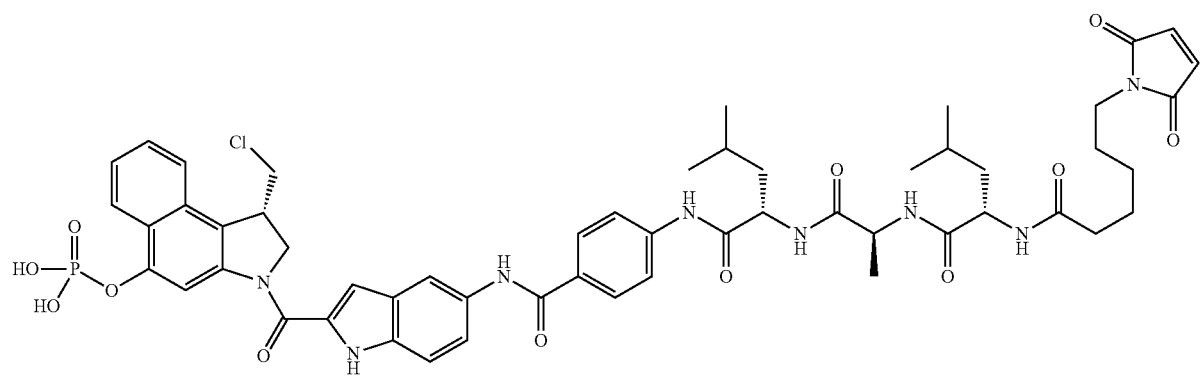
(IIe)
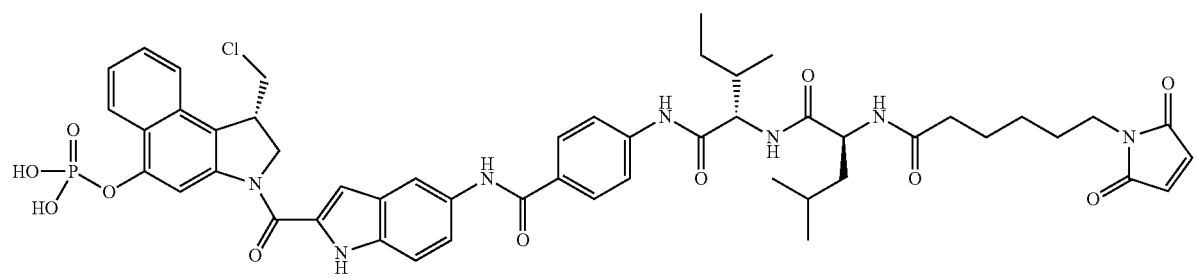
(IIf)

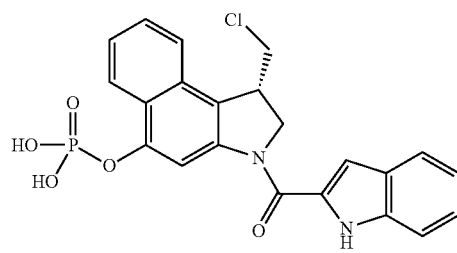
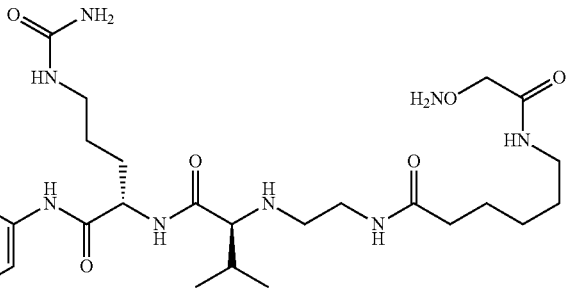

or a pharmaceutically acceptable salt thereof.

In formulae (I) and (II), X is a nucleophilically displaceable group, preferably Cl, Br, or tosylate, more preferably Cl.

In formulae (II), (IIIa) and (IIIb), $AA^a$ and each $AA^b$ are independently selected from the group consisting of alanine, β-alanine, γ-aminobutyric acid, arginine, asparagine, aspartic acid, γ-carboxyglutamic acid, citrulline (Cit), cysteine, glutamic acid, glutamine, glycine, histidine, isoleucine, leucine, lysine, methionine, norleucine, norvaline, ornithine, phenylalanine, proline, serine, threonine, tryptophan, tyrosine, and valine. Preferably, $AA^a$ and $AA^b$ are selected from the group consisting of arginine, aspartic acid, citrulline, glutamic acid, glutamine, glycine, histidine, lysine, phenylalanine, serine, threonine, tryptophan, tyrosine, and valine.

The moiety -$AA^a$-[$AA^b$]$_m$- in formulae (II), (IIIa) and (IIIb) represents a peptidyl linker where consecutive amino acids are joined by peptidyl bonds. It preferably is one that is cleavable by an intracellular or extracellular enzyme associated with the target cell. The enzyme can be, for example, cathepsin B, cathepsin E, legumain, or CD10. The peptidyl linker preferably consists of one to six, more preferably one to three, and most preferably one to two amino acids. $AA^a$ preferably is Cit, Lys, Glu, Ser, Ile, Leu, or Thr, more preferably Cit or Lys, especially in combination with m equals 0, 1, or 2.

The suffix m in formulae (II), (IIIa) and (IIIb) is 0, 1, 2, 3, 4, or 5. Preferably, m is 0, 1, or 2, more preferably 1. Thus, -$AA^a$-[$AA^b$]$_m$- represents a single amino acid linker, a dipeptide linker, a tripeptide linker, and so forth, according to the value of m, with $AA^a$ being at the C-terminus and $AA^b$ at the N-terminus. Where m is 1, so that $AA^a$ and $AA^b$ in combination form a dipeptide, preferred dipeptides are Val-Cit, Phe-Cit, Phe-Lys, Val-Lys, Val-Glu, Val-Asp, Val-Ser, and Val-Gly, each dipeptide being recited in the conventional N-to-C direction. A Val-Cit dipeptide linker is especially preferred. Where the peptidyl linker consists of a single amino acid (i.e., m is 0), it preferably is Cit, Glu, Lys, or Ser, as taught in Chen et al. 2010, the disclosure of which is incorporated herein by reference. Preferably, the foregoing dipeptide and single peptide linkers are cleavable by cathepsin B. Another enzyme that can be utilized for cleaving peptidyl linkers is legumain, a lysosomal cysteine protease that preferentially cleaves at Ala-Ala-Asn. The peptides Leu-Ala-Leu and Leu-Ile are designed to be cleaved by CD10 and cathepsin E, respectively.

Spacer Y in formulae (II), (IIIa), and (IIIb) provides spatial separation between the prodrugged seco-MGBA and the antibody (or antigen binding fragment thereof), lest the former sterically interfere with antigen binding by latter or the latter sterically interfere with cleavage of the peptidyl linker. Further, spacer Y can be used to confer increased solubility or decreased aggregation properties to the conjugates. Spacer Y can comprise one or more modular segments, which can be assembled in any number of combinations. Examples of suitable segments for spacer Y are:

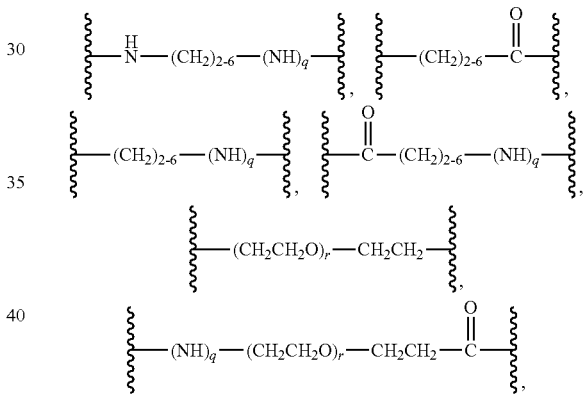

and combinations thereof, where the subscript q is 0 or 1 independently for each occurrence thereof and the subscript r is 1 to 24, preferably 2 to 4, independently for each occurrence thereof. These segments can be combined, such as shown below:

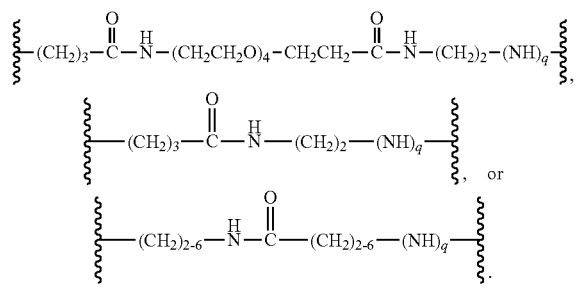

Spacer Y preferably provides a linear separation of from 5 to 20 atoms, more preferably from 5 to 15 atoms, between the amino acid $AA^a$ or $AA^b$ to which it is bonded and the reactive functional group Z.

In another preferred embodiment, spacer Y is connected to AA$^a$ or AA$^b$, as the case may be, by other than a carboxylic acyl group directly attached to the alpha-amino group of AA$^a$ or AA$^b$. Preferably, spacer Y is connected to the alpha-amino group of AA$^a$ or AA$^b$, as the case may be, via a methylene group in spacer Y.

In formula (II), Z is a reactive functional group capable of conjugation to an antibody. Preferably, —Z is —NH$_2$, —OH, —ONH$_2$ (hydroxylamine), —CO$_2$H, —SH, cyclooctyne, azide (—N$_3$),

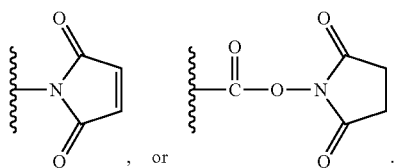 [SMILES: *N1C(=O)C=CC1=O ; *C(=O)ON1C(=O)CCC1=O]

More preferably, —Z is —ONH$_2$, —SH, —N$_3$, or

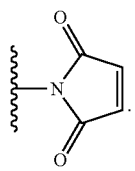

An —OH group can be esterified with a carboxy group on the antibody, for example, on an aspartic or glutamic acid side chain.

A —CO$_2$H group can be esterified with a —OH group or amidated with an amino group (for example on a lysine side chain) on the antibody.

A maleimide group can be conjugated with an —SH group on the antibody (e.g., from cysteine or from the chemical modification of the antibody to introduce a sulfhydryl functionality), in a Michael addition reaction.

An N-hydroxysuccinimide group is functionally an activated carboxyl group and can conveniently be amidated by reaction with an amino group (e.g., from lysine).

An —SH group is particularly useful for conjugation where the antibody has been modified to introduce a maleimide group thereto, in a Michael addition reaction that is the "mirror image" of that described above. Antibodies can be modified to have maleimide groups with N-succinimidyl 4-(maleimidomethyl)-cyclohexanecarboxylate (SMCC) or its sulfonated variant sulfo-SMCC, both reagents being available from Sigma-Aldrich.

Azide and cyclooctyne are complementary functional groups that can effect conjugation via so-called "click chemistry," in which the azide adds across the strained alkyne bond of the cyclooctyne to form an 1,2,3-triazole ring. The azide can be the Z-group in a compound of formula (II) and the cyclooctyne can be situated on the antibody or antigen binding fragment thereof, or vice-versa. A cyclooctyne group can be provided by a DIBO reagent (available from Invitrogen/Molecular Probes, Eugene, Oreg.).

Techniques for introducing non-natural amino acids into antibodies can be utilized, with the non-natural amino acid providing a functionality for conjugation with the reactive functional group. For instance, the non-natural amino acid p-acetylphenylalanine can be incorporated into an antibody, as taught in Tian et al., WO 2008/030612 A2 (2008). The ketone group in p-acetylphenylalanine can be a conjugation site by the formation of an oxime with a hydroxylamino reactive functional group. Other non-natural amino acids also can be incorporated using the ReCODE™ technology of Ambrx, Inc. (La Jolla, Calif.).

In the foregoing immunoconjugates, the antibody preferably is an antibody against a tumor associated antigen, allowing the immunoconjugate to selectively or preferentially target cancer cells. Examples of such antigens include: mesothelin, prostate specific membrane antigen (PSMA), CD19, CD22, CD30, CD70, B7H4 (also known as O8E), protein tyrosine kinase 7 (PTK7), glypican-3, RG1, CTLA-4, and CD44. The antibody can be animal (e.g., murine), chimeric, humanized, or, preferably, human. The antibody preferably is monoclonal, especially a monoclonal human antibody. The preparation of human monoclonal antibodies against some of the aforementioned antigens is disclosed in Korman et al., US 2009/0074660 A1 (B7H4); Rao-Naik et al., U.S. Pat. No. 8,097,703 B2 (CD19); King et al., US 2010/0143368 A1 (CD22); Keler et al., U.S. Pat. No. 7,387,776 B2 (2008) (CD30); Terrett et al., U.S. Pat. No. 8,124,738 B2 (CD70); Korman et al., U.S. Pat. No. 6,984,720 B1 (2006) (CTLA-4); Korman et al., US 2009/0217401 A1 (PD-1); Huang et al., US 2009/0297438 A1 and Cardarelli et al., U.S. Pat. No. 7,875,278 B2 (PSMA); Lu et al., US 2010/0034826 A1 (PTK7); Terrett et al., US 2010/0209432 (A1) (glypican-3); Harkins et al., U.S. Pat. No. 7,335,748 B2 (2008) (RG1); Terrett et al., US 2011/0262448 A1 (mesothelin); and Xu et al., US 2010/0092484 A1 (CD44); the disclosures of which are incorporated herein by reference. Preferably, the antibody is a human monoclonal antibody against CD70, mesothelin, CD19, glypican-3, B7H4, RG-1, CD22, or PTK7.

Another aspect of the invention is a prodrugged compound of the formula (I)

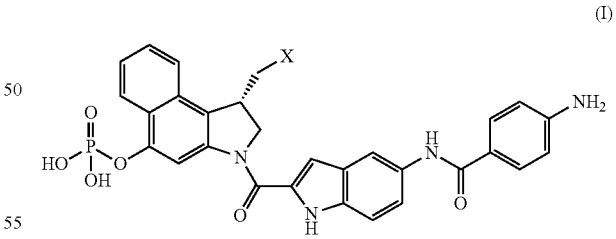

or a pharmaceutically acceptable salt thereof, where X is a nucleophilically displaceable leaving group, which preferably is Cl, Br, or tosylate and more preferably is Cl. A compound of formula (I) can be conjugated to an antibody or an antigen-binding fragment thereof to make a therapeutically useful immunoconjugate by the employment of an appropriate linker, spacer, and reactive functional group, as discussed above. A preferred embodiment of formula (I) in which X is Cl corresponds to a structure of formula (Ia):

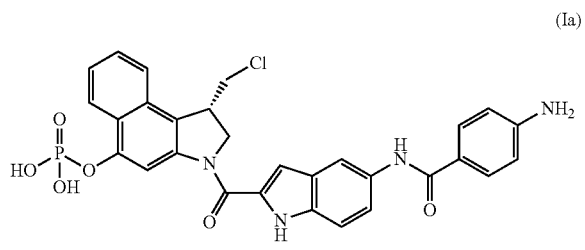 [SMILES: Nc1ccc(C(=O)Nc2ccc3[nH]c(C(=O)N4C[C@@H](CCl)c5c4cc(OP(=O)(O)O)c4ccccc54)cc3c2)cc1]

(Ia)

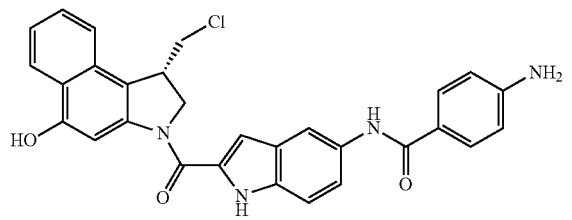

(IV)

Biological Activity

A series of cell proliferation experiments were conducted, in which the ability of immunoconjugates prepared from compound (IIa) and prior art compound (A) were compared. In each instance, the technique used was the $^3$H thymidine incorporation assay, the procedural details of which are provided in the Examples hereinbelow.

Figure 4A:
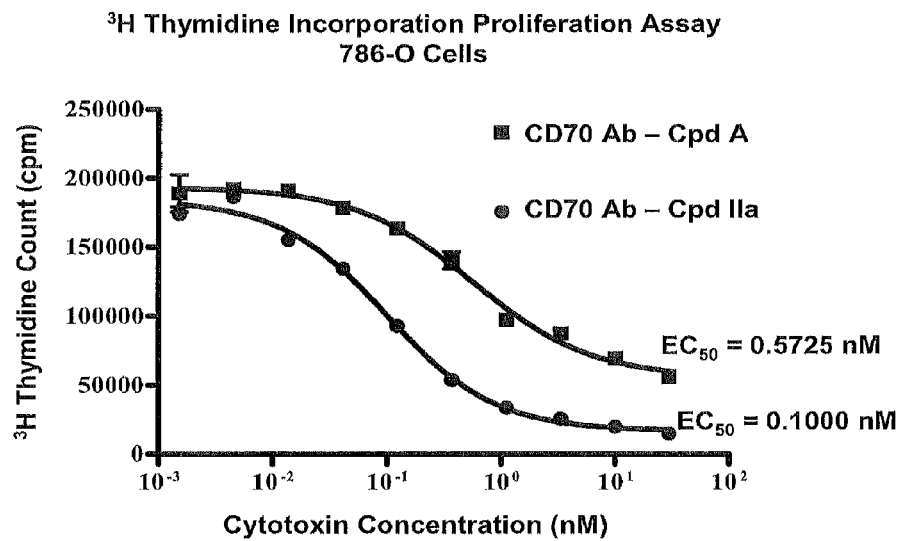

FIG. 4A shows the inhibitory activity of the two immunoconjugates on the proliferation of 786-O cells, which are CD70-expressing human renal cancer cells. In each instance the conjugated antibody was 2H5, an anti-CD70 human monoclonal antibody. The compound (IIa) immunoconjugate not only had a lower $EC_{50}$ (0.1000 nM versus 0.5725 nM) but

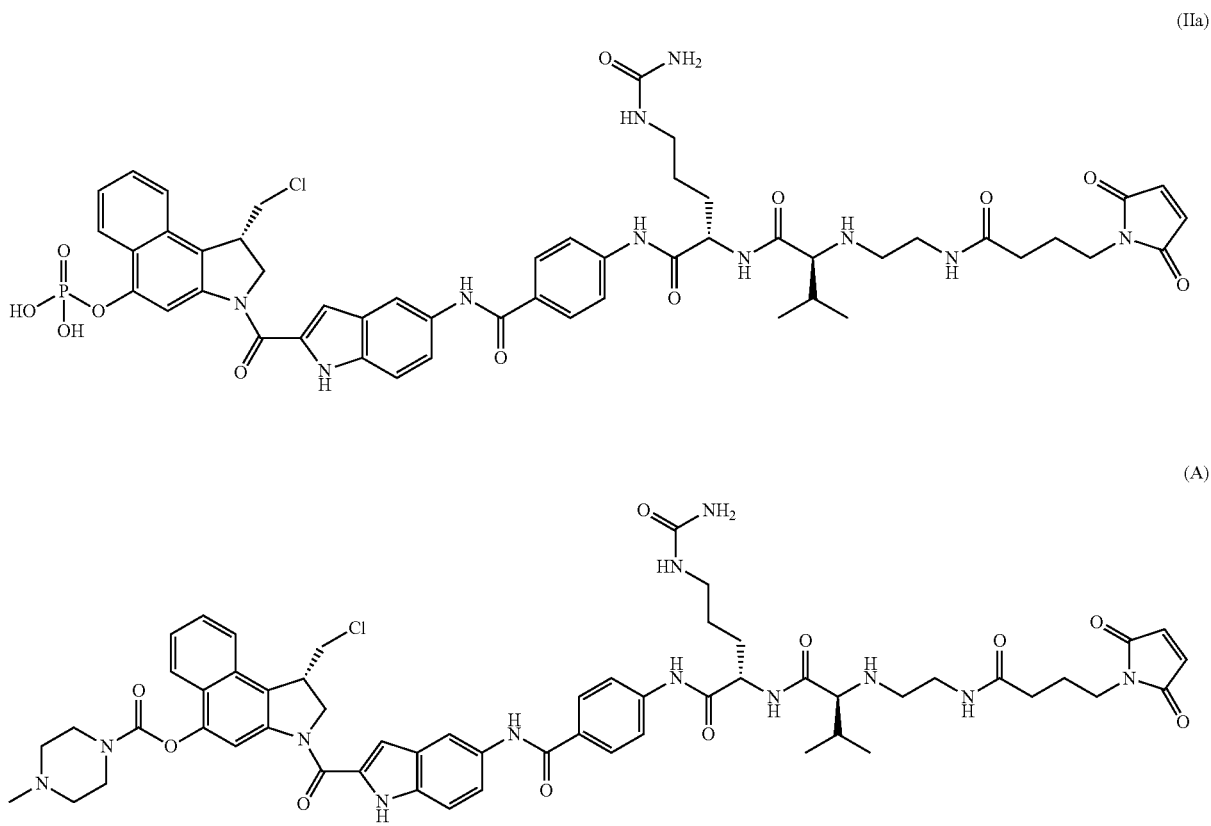

Since the immunoconjugates are identical except for the prodrugging group—phosphate versus carbamate—and the same drug of formula (IV) is released after cleavage of the peptidyl linker and removal of the prodrugging group, the experiments provide a comparison of the effect of the prodrugging group on immunoconjugate potency. These side-by-side results show that, unexpectedly, immunoconjugates of compound (IIa) are significantly more potent than those of compound (A), even though the same ultimate active compound (IV) is involved in each instance.

also had a higher overall percentage of inhibition, as evidenced by the depth of its inhibition curve. (The full sequence information for antibody 2H5 is disclosed in Coccia et al. 2010 and Terret et al. 2012b; the disclosures of which are incorporated herein by reference. The $V_H$ CDR1, CDR2, and CDR3 and $V_K$ CDR1, CDR2, and CDR3 sequences for antibody 2H5 are given in SEQ ID NO:1, SEQ ID NO:2, SEQ ID NO:3, SEQ ID NO:4, SEQ ID NO:5, and SEQ ID NO:6, respectively.)

Figure 4B:
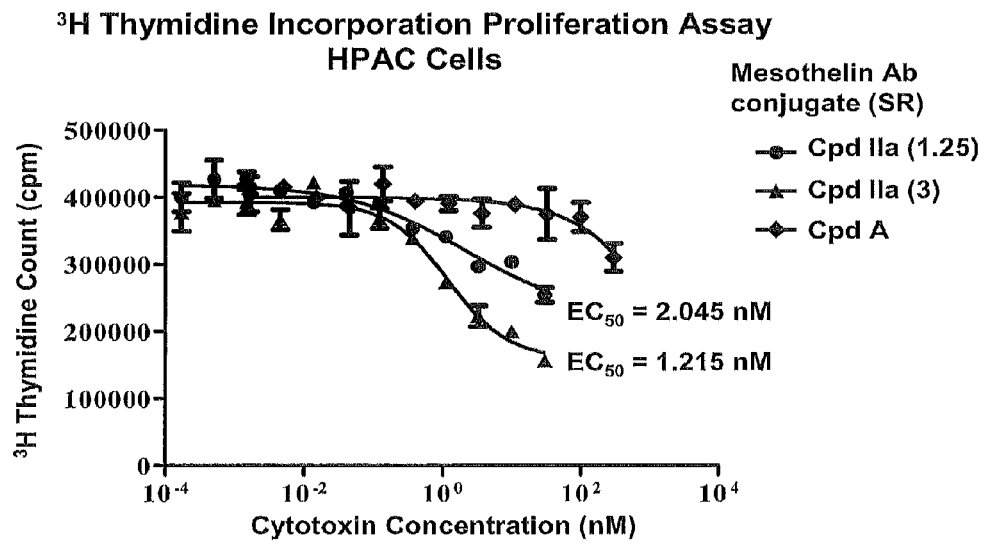

FIG. 4B is a similar study, but using HPAC cells, which are mesothelin expressing human pancreatic cancer cells. In each instance, the conjugated antibody was 6A4, an anti-mesothelin human monoclonal antibody. In this experiment, two different compound (IIa) conjugates were prepared, with substitution ratios of 1.25 and 3. (The cytotoxin concentrations on the X-axis are adjusted to reflect the substitution ratio.) FIG. 4B shows that the compound (A) immunoconjugate was essentially inactive, while the compound (IIa) immunoconjugates had approximately nanomolar $EC_{50}$'s. It is also noteworthy that the higher substitution ratio compound (IIa) immunoconjugate showed higher overall percentage of inhibition (deeper curve). (The full sequence information for antibody 6A4 is disclosed in Terrett et al. 2011b, the disclosure of which is incorporated by reference. The $V_H$ CDR1, CDR2, and CDR3 and $V_K$ CDR1, CDR2, and CDR3 sequences for antibody 6A4 are given in SEQ ID NO:7, SEQ ID NO:8, SEQ ID NO:9, SEQ ID NO:10, SEQ ID NO:11, and SEQ ID NO:12, respectively.)

Figure 4C:
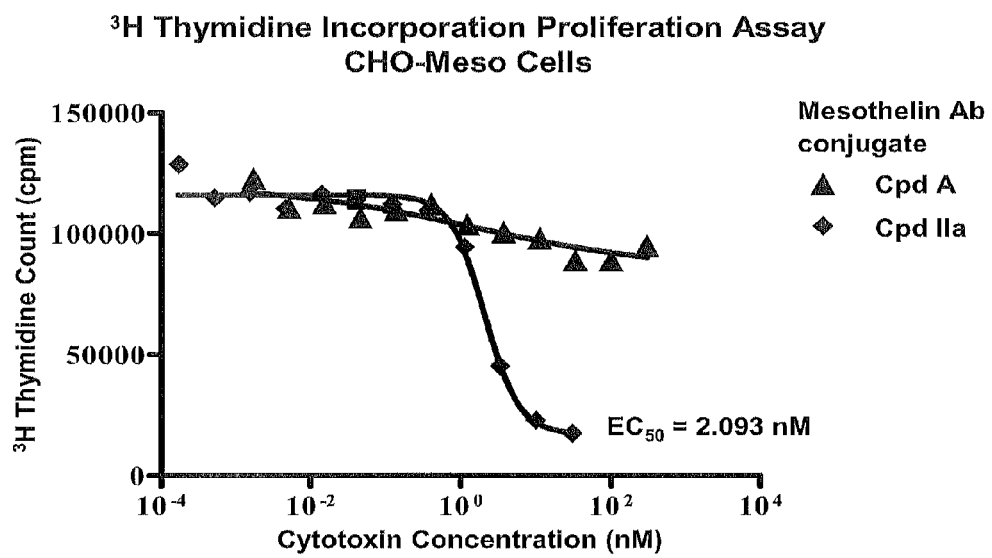

FIG. 4C is another similar study, this time using CHO-meso cells, which are Chinese hamster ovary cells transfected to express mesothelin. The conjugated antibody was, again, 6A4. The compound (A) immunoconjugate was essentially inactive, while the compound (IIa) immunoconjugate had an $EC_{50}$ of about 2 nM.

Figure 4D:
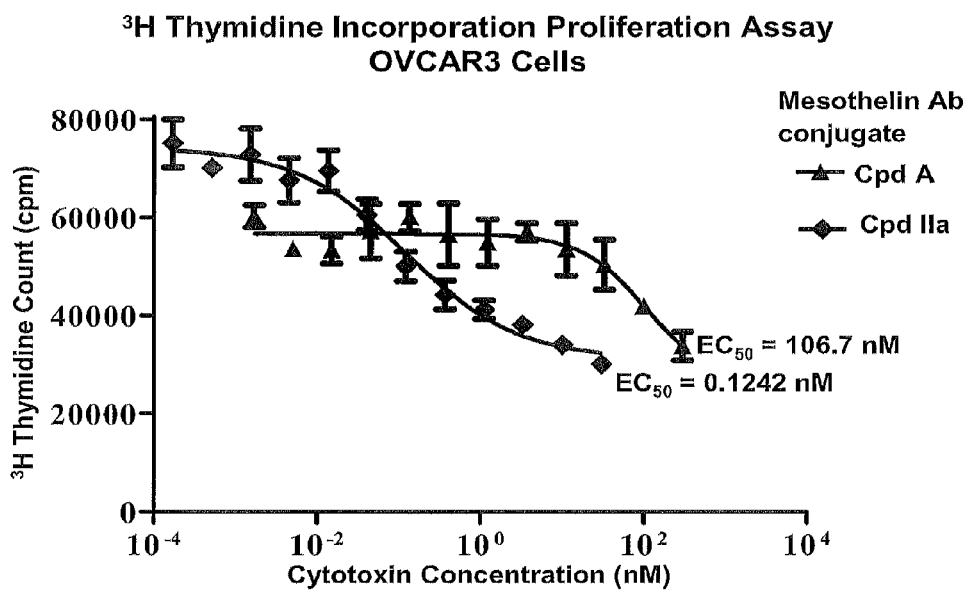

FIG. 4D is yet another similar study, this time using OVCAR3 cells, which are mesothelin-expressing human ovarian cancer cells. Again, the conjugated antibody was 6A4. The $EC_{50}$ for the compound (IIa) immunoconjugate was approximately 1000 times lower than that for the compound (A) immunoconjugate.

Figure 4E:
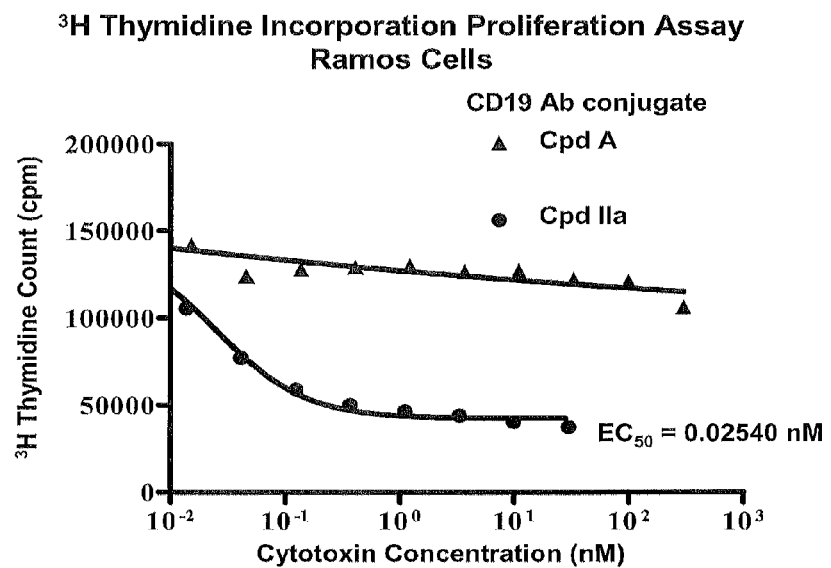

FIG. 4E is yet another similar study, this time using Ramos cells, which are CD19-expressing human Burkitt's lymphoma cells. The conjugated antibody was 21D4, an anti-CD 19 human monoclonal antibody. The disparity between the compound (A) and (IIa) immunoconjugates was again marked, with the former being essentially inactive while the latter had a sub-nanomolar $EC_{50}$. (The full sequence information for antibody 21D4 is disclosed in King et al. 2010a and Rao-Naik et al. 2012; the disclosures of which are incorporated by reference. The $V_H$ CDR1, CDR2, and CDR3 and $V_K$ CDR1, CDR2, and CDR3 sequences for antibody 21D4 are given in SEQ ID NO:13, SEQ ID NO:14, SEQ ID NO:15, SEQ ID NO:16, SEQ ID NO:17, and SEQ ID NO:18, respectively.)

Figure 4F:
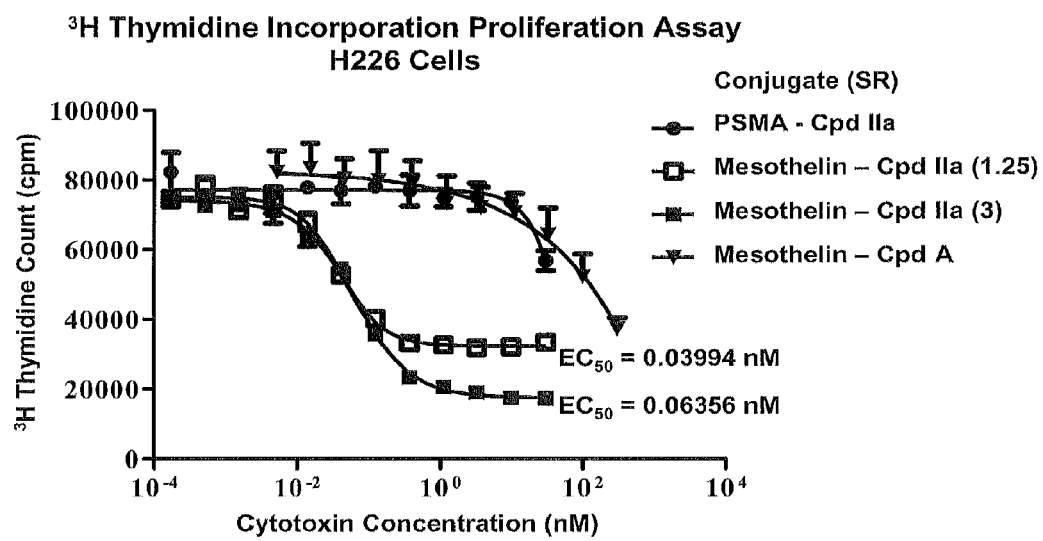

FIG. 4F is yet another similar study, this time with NC1-H226 (H226) cells, which are mesothelin-expressing human lung-derived mesothelioma cells. The conjugated antibody was, again, 6A4. Additionally, as an isotype control, compound (IIa) was conjugated to 2A10, which is a human monoclonal antibody against prostate specific membrane antigen ("PSMA"). As expected, the PSMA immunoconjugate had very little or no activity, as H226 cells do not express PSMA. The compound (A) immunoconjugate had similarly low or no activity. In contrast, the two compound (IIa) immunoconjugates each had sub-nanomolar $EC_{50}$'s. As in previous examples, the immunoconjugate with the higher substitution ratio exhibited a higher overall percentage of proliferation inhibition. (The full sequence information for antibody 2A10 is disclosed in Huang et al. 2009 and Cardarelli et al. 2011; the disclosures of which are incorporated by reference. The $V_H$ CDR1, CDR2, and CDR3 and $V_K$ CDR1, CDR2, and CDR3 sequences for antibody 2A10 are given in SEQ ID NO:19, SEQ ID NO:20, SEQ ID NO:21, SEQ ID NO:22, SEQ ID NO:23, and SEQ ID NO:24, respectively.)

Figure 4G:
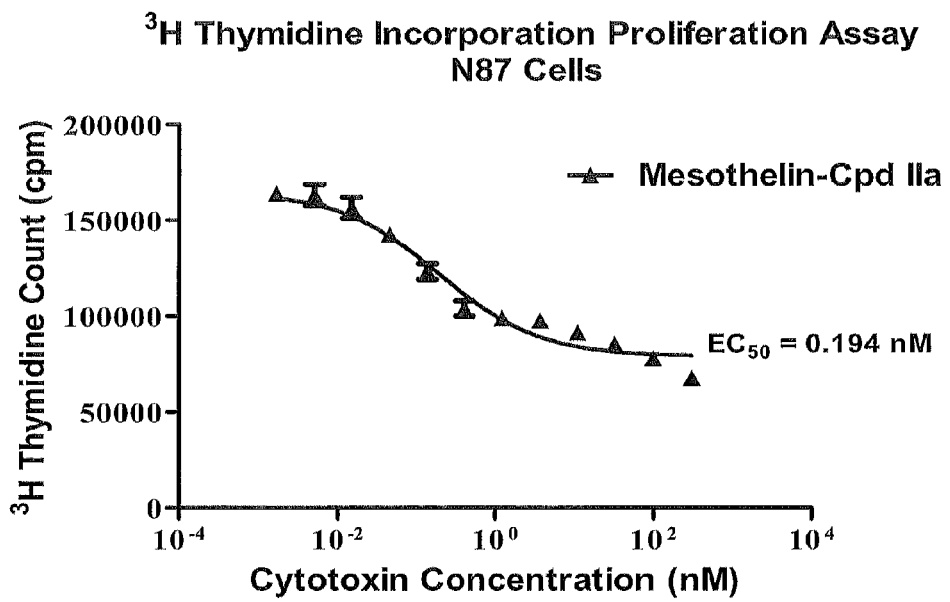

FIG. 4G shows the activity of an immunoconjugate of anti-mesothelin antibody 6A4 and compound (IIa) against N87 human gastric carcinoma cells, which express mesothelin. A subnanomolar $EC_{50}$ was observed.

Figure 4H:
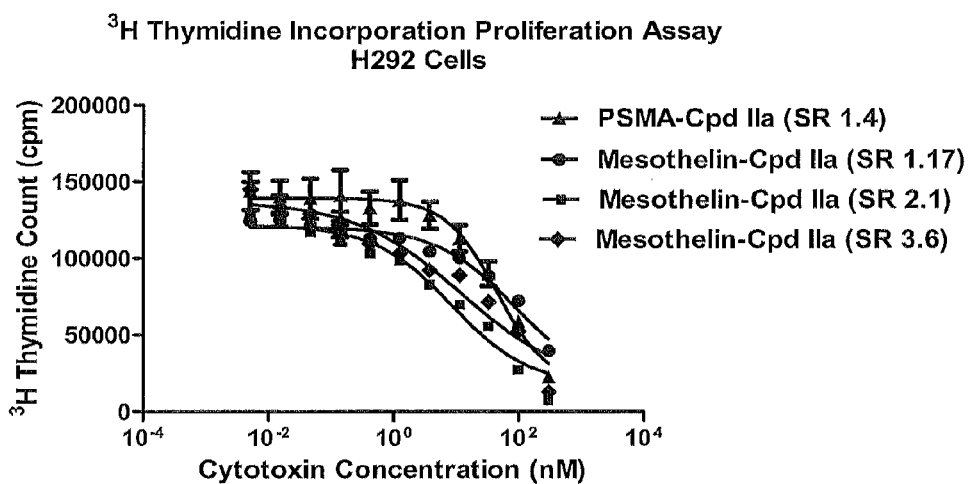

FIG. 4H shows the activity of immunoconjugates of antibody 6A4 and compound (IIa) at various substitution ratios (SRs) against H292 cells, which are mesothelin expressing human mucoepidermoid pulmonary carcinoma cells. An immunoconjugate of anti-PSMA antibody 2A10 and compound (IIa) was used as a control. The $EC_{50}$ values are shown in Table I, below. They show that there is a significant increase in potency when the SR is increased to about two or above.

TABLE I

Activity against H292 Cells

| Immunoconjugate | $EC_{50}$ (nM) |
|---|---|
| PSMA - Cpd IIa | 44.8 |
| Mesothelin - Cpd IIa (SR 1.17) | 86.5 |
| Mesothelin - Cpd IIa (SR 2.1) | 8.36 |
| Mesothelin - Cpd IIa (SR 3.6) | 11.9 |

Figure 4I:
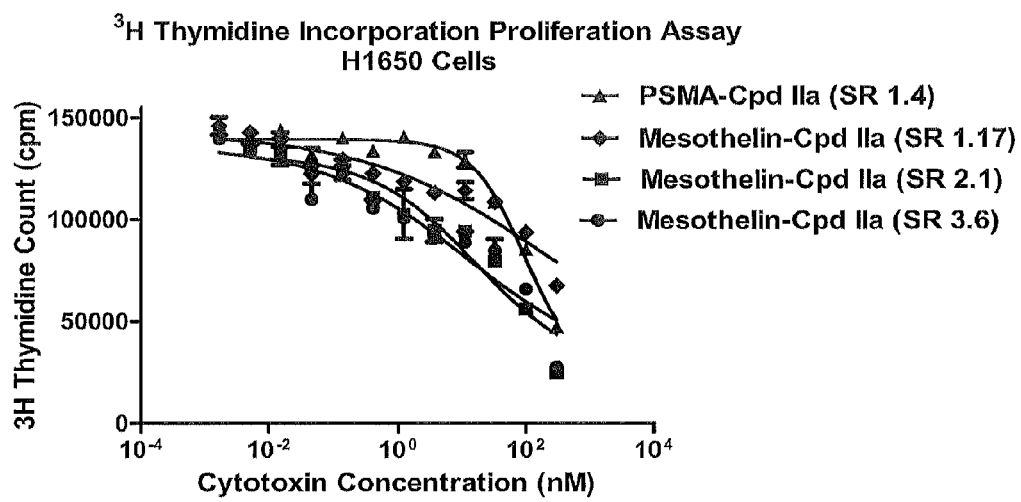

FIG. 4I shows a study similar to that of FIG. 4H, but against H1650 cells, which are mesothelin expressing human adenocarcinoma cells. The $EC_{50}$ values are presented in Table II. Again, a jump in potency was noted at SR above about two.

TABLE II

Activity against H1650 Cells

| Immunoconjugate | $EC_{50}$ (nM) |
|---|---|
| PSMA - Cpd IIa | 95.3 |
| Mesothelin - Cpd IIa (SR 1.17) | 180 |
| Mesothelin - Cpd IIa (SR 2.1) | 16.6 |
| Mesothelin - Cpd IIa (SR 3.6) | 12.1 |

Figure 4J:
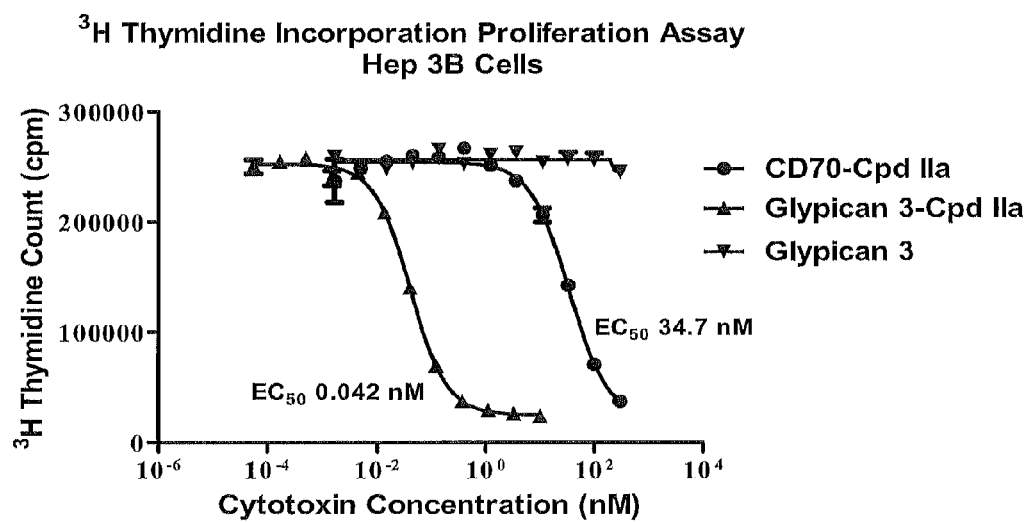
Figure 4K:
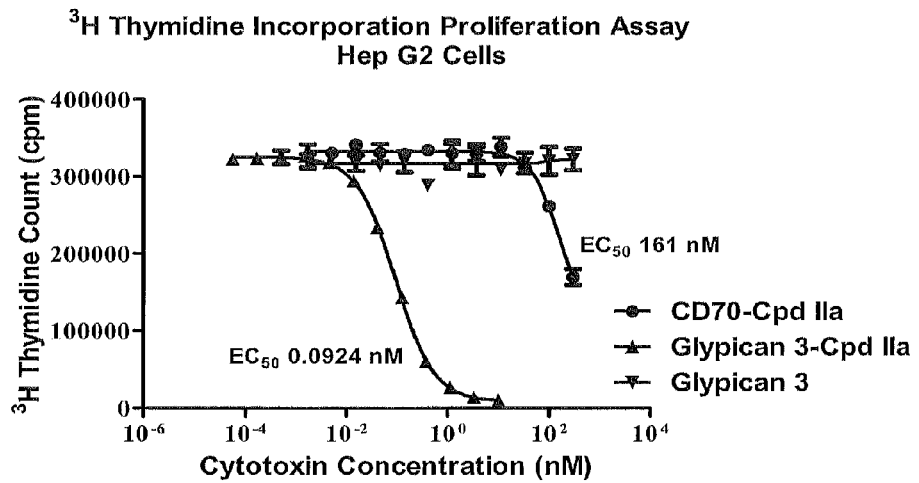

FIGS. 4J and 4K are studies of immunoconjugates of this invention against two human hepatocellular carcinoma cell lines, Hep 3B and Hep G2, both of which express glypican-3. The potency of the anti-glypican-3 human monoclonal antibody 4A6 alone and when conjugated to compound (IIa) were compared, along with a control immunoconjugate of anti-CD70 antibody 2H5 and compound (IIa). (Neither Hep 3B nor Hep G2 cells express CD70.) The results show that the 4A6 immunoconjugate was very potent, about 1000× more active than the control CD70 immunoconjugate. The anti-glypican-3 antibody 4A6 alone was inactive. (The sequence information for antibody 4A6 is disclosed in Terrett et al. 2010b, the disclosure of which is incorporated by reference. The $V_H$ CDR1, CDR2, and CDR3 and $V_K$ CDR1, CDR2, and CDR3 sequences for antibody 4A6 are given in SEQ ID NO:25, SEQ ID NO:26, SEQ ID NO:27, SEQ ID NO:28, SEQ ID NO:29, and SEQ ID NO:30, respectively.)

Figure 4L:
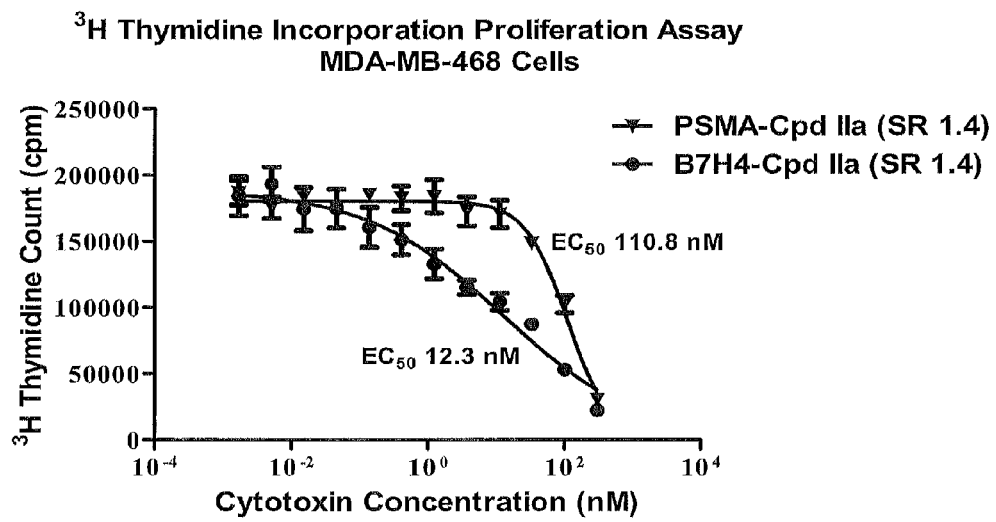
Figure 4M:
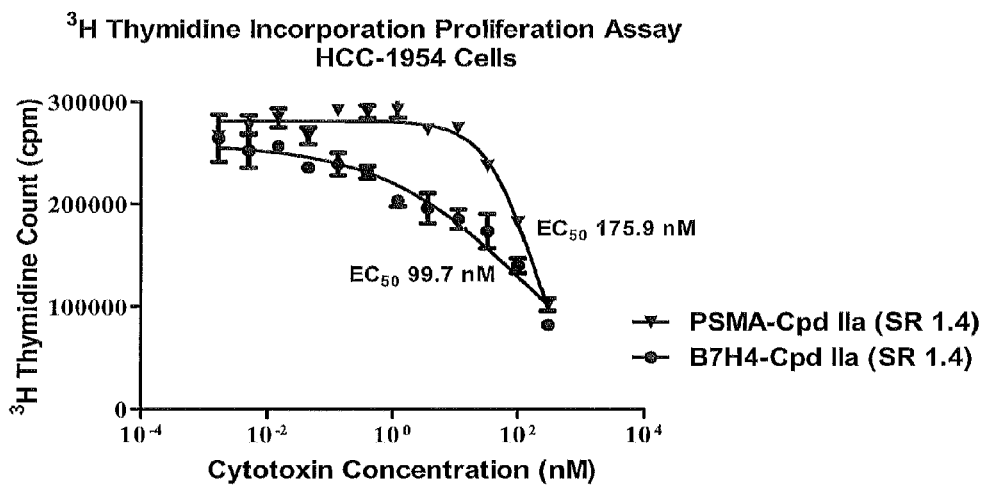
Figure 4N:
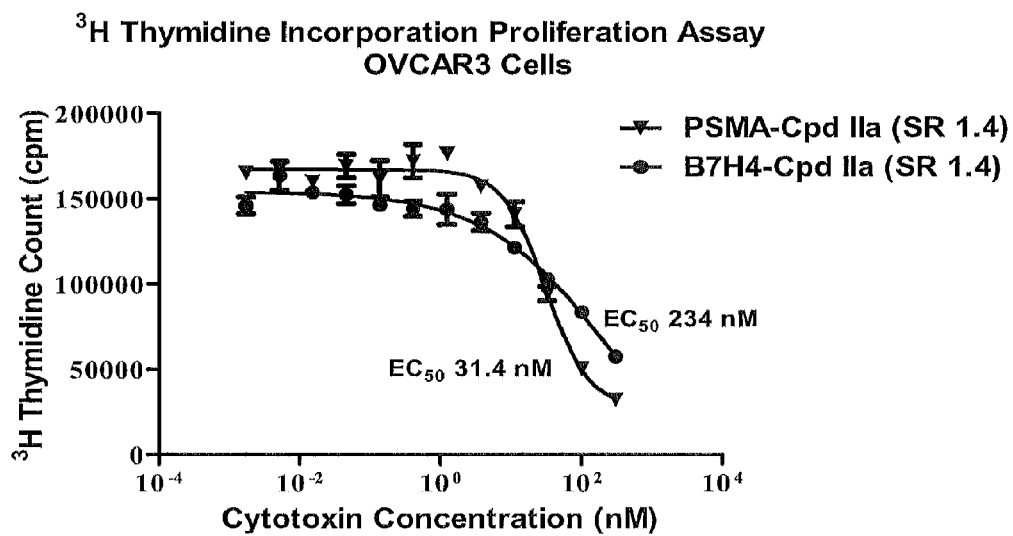

FIGS. 4L, 4M, and 4N are studies of the activity of an immunoconjugate of the anti-B7H4 human monoclonal antibody 2A7 and compound (IIa) against MDA-MB-468, HCC-1954, and OVCAR3 cell lines. The first two are human breast cancer cell lines, while the third one is a human ovarian cancer cell line, all of which express B7H4 but not CD70. An immunoconjugate of anti-PSMA antibody 2A10 and compound IIa was used as control. It can be seen from figures that there was some specific activity against the breast cancer cell lines but little or none against OVCAR3 cells. (The full sequence information for antibody 2A7 is disclosed in Korman et al. 2009 and Terrett et al. 2011a; the disclosures of which are incorporated by reference. The $V_H$ CDR1, CDR2, and CDR3 and $V_L$ CDR1, CDR2, and CDR3 sequences for antibody 2A7 are given in SEQ ID NO:31, SEQ ID NO:32, SEQ ID NO:33, SEQ ID NO:34, SEQ ID NO:35, and SEQ ID NO:36, respectively.)

Figure 4O:
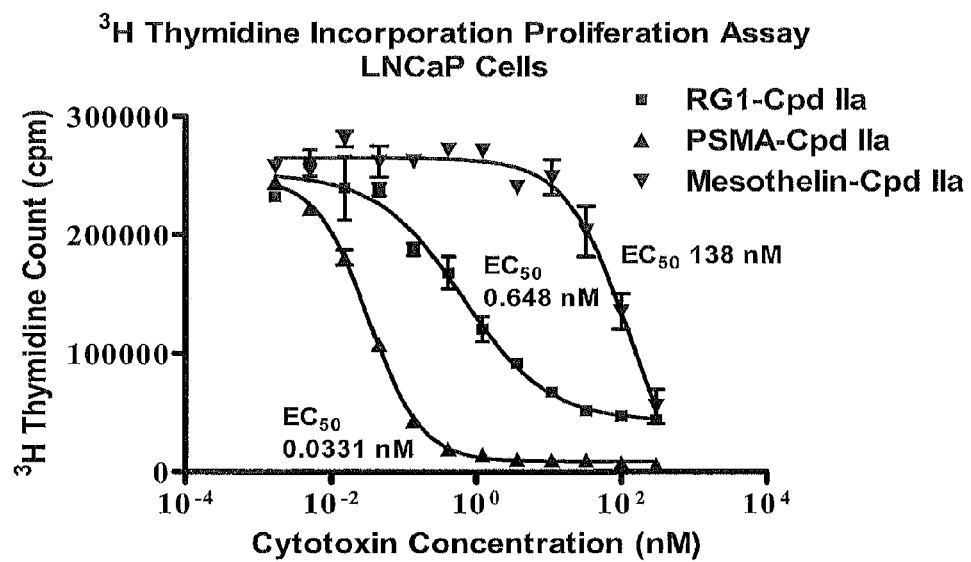

FIG. 4O is a study of the activity of immunoconjugates of the anti-PSMA human monoclonal antibody 2A10 and the anti-RG-1 human monoclonal antibody 19G9, each conjugated to compound (IIa), against LNCap human prostate cancer cells, which express both PSMA and RG-1. Comparison data is provided for an immunoconjugate of anti-mesothelin antibody 6A4 and compound (IIa), as a control. It can be seen that both the PSMA and RG-1 conjugates were were effective, each with subnanomolar $EC_{50}$'s. (The full sequence information for antibody 19G9 is disclosed in King et al. 2011, the disclosure of which is incorporated herein by reference. The $V_H$ CDR1, CDR2, and CDR3 and $V_L$ CDR1, CDR2, and CDR3 sequences for antibody 19G9 are given in SEQ ID NO:37, SEQ ID NO:38, SEQ ID NO:39, SEQ ID NO:40, SEQ ID NO:41, and SEQ ID NO:42, respectively.)

Figure 4P:
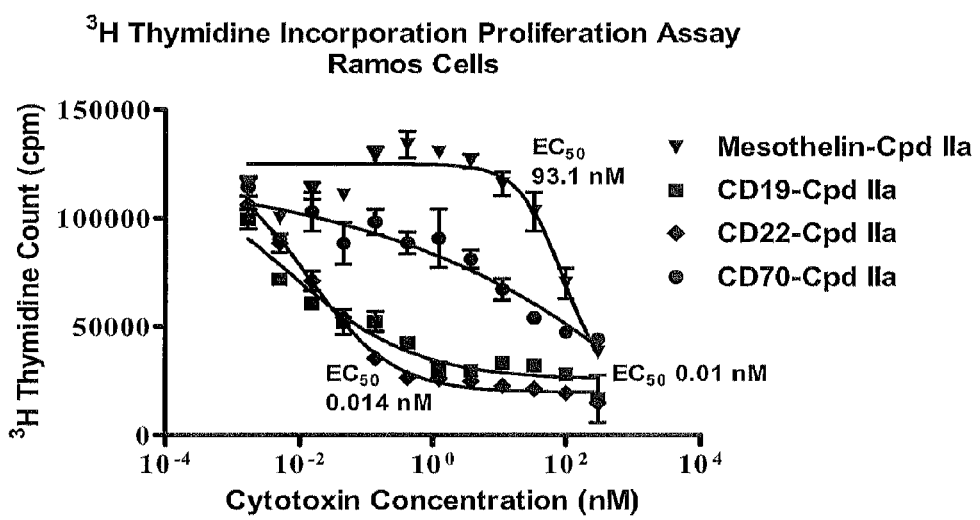

FIG. 4P is a study of the activity of immunoconjugates of the anti-CD19 human monoclonal antibody 21D4 and the anti-CD22 human monoclonal antibody 12C5, each conjugated to compound (IIa), against Ramos cells, which express both CD19 and CD22. Comparison data is provided for immunoconjugates of anti-mesothelin antibody 6A4 and anti-CD70 antibody 2H5 compound (IIa). Both of the anti-CD19 and anti-CD22 immunoconjugates were highly potent, each with subnanomolar $EC_{50}$'s. (The full sequence information for antibody 12C5 is disclosed in King et al. 2010b, the disclosure of which is incorporated by reference. The $V_H$ CDR1, CDR2, and CDR3 and $V_K$ CDR1, CDR2, and CDR3 sequences for antibody 12C5 are given in SEQ ID NO:43, SEQ ID NO:44, SEQ ID NO:45, SEQ ID NO:46, SEQ ID NO:47, and SEQ ID NO:48, respectively.)

Figure 4Q:
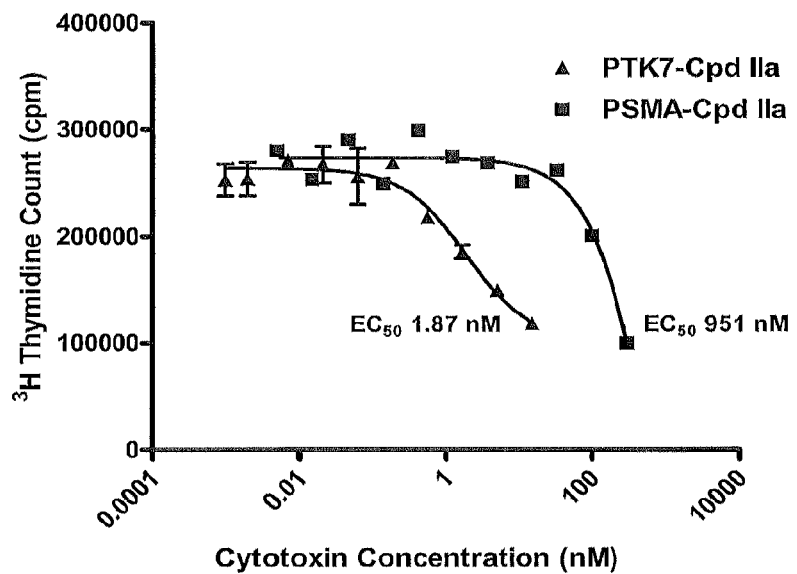

FIG. 4Q shows the activity of an immunoconjugate of anti-PTK7 human monoclonal antibody 4D5 with compound IIa against HCT116 cells, which are human colon carcinoma cells. The immunoconjugate had an $EC_{50}$ of 1.87 nM, while a control immunoconjugate of the anti-PSMA antibody 2A10 was much less potent, with an $EC_{50}$ of 951 nM. (The full sequence information for antibody 4D5 is disclosed in Terrett et al. 2010a and Terrett et al. 2012a; the disclosures of which are incorporated by reference. The $V_H$ CDR1, CDR2, and CDR3 and $V_K$ CDR1, CDR2, and CDR3 sequences for antibody 4D5 are given in SEQ ID NO:49, SEQ ID NO:50, SEQ ID NO:51, SEQ ID NO:52, SEQ ID NO:53, and SEQ ID NO:54, respectively.)

Figure 4R:
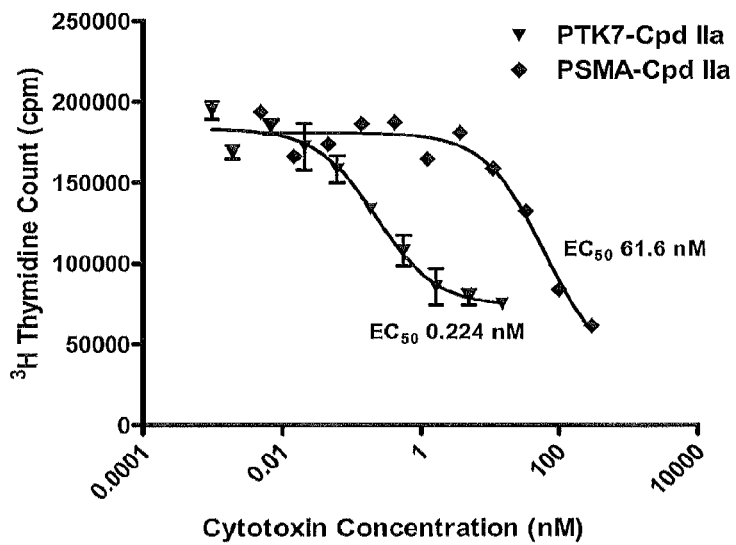

FIG. 4R shows the activity of an immunoconjugate of the aforementioned anti-PTK7 antibody 4D5 against H520 cells, which are human lung squamous cell carcinoma cells. The PTK7 immunoconjugate had an $EC_{50}$ of 0.224 nM, while the control PSMA immunoconjugate again was much less potent, with an $EC_{50}$ of 61.6 nM.

The foregoing results demonstrate that, unexpectedly, the nature of the prodrugging group—phosphate versus carbamate—plays a substantial role in the potency of immunoconjugates that are otherwise identical. Without being bound by theory, our hypothesis is that different human cells (including cancer cells) contain different levels of carboxyesterase and that many, if not most, contain insufficient carboxyesterase levels to cleave the carbamate prodrugging group in an efficient manner. However, the immunoconjugates prodrugged with a phosphate group are not afflicted with such a problem, presumably because in most, if not all cells, the level of phosphatase activity is sufficiently high for efficient cleavage of the phosphate group.

Uses

Immunoconjugates of this invention be used for treating diseases such as, but not limited to, hyperproliferative diseases, including: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; ovarian cancer; small cell and non-small cell lung cancer (SCLC and NSCLC); breast cancer sarcomas, such as fibrosarcoma, malignant fibrous histiocytoma, embryonal rhabdomyosarcoma, leiomysosarcoma, neurofibrosarcoma, osteosarcoma, synovial sarcoma, liposarcoma, and alveolar soft part sarcoma; leukemias such as acute promyelocytic leukemia (APL), acute myelogenous leukemia (AML), acute lymphoblastic leukemia (ALL), and chronic myelogenous leukemia (CML); neoplasms of the central nervous systems, particularly brain cancer; multiple myeloma (MM), lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma. Clinically, practice of the methods and use of compositions described herein will result in a reduction in the size or number of the cancerous growth and/or a reduction in associated symptoms (where applicable). Pathologically, practice of the method and use of compositions described herein will produce a pathologically relevant response, such as inhibition of cancer cell proliferation, reduction in the size of the cancer or tumor, prevention of further metastasis, and inhibition of tumor angiogenesis. The method of treating such diseases comprises administering a therapeutically effective amount of an inventive combination to a subject. The method may be repeated as necessary. Especially, the cancer can be a cancer whose cells express CD70, mesothelin, CD19, glypican-3, B7H4, RG-1, CD22, or PTK7. In a preferred embodiment, the cancer being treated is renal cancer, pancreatic cancer, ovarian cancer, lymphoma, colon cancer, mesothelioma, gastric cancer, lung cancer, prostate cancer, adenocarcinoma, liver cancer, or breast cancer.

Immunoconjugates of this invention can be administered in combination with other therapeutic agents, including antibodies, alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, immunomodulators, microtubule stabilizers, nucleoside (purine or pyrimidine) analogs, nuclear export inhibitors, proteasome inhibitors, topoisomerase (I or II) inhibitors, tyrosine kinase inhibitors, and serine/threonine kinase inhibitors. Specific therapeutic agents include adalimumab, ansamitocin P3, auristatin, bendamustine, bevacizumab, bicalutamide, bleomycin, bortezomib, busulfan, callistatin A, camptothecin, capecitabine, carboplatin, carmustine, cetuximab, cisplatin, cladribin, cytarabin, cryptophycins, dacarbazine, dasatinib, daunorubicin, docetaxel, doxorubicin, duocarmycin, dynemycin A, epothilones, etoposide, floxuridine, fludarabine, 5-fluorouracil, gefitinib, gemcitabine, ipilimumab, hydroxyurea, imatinib, infliximab, interferons, interleukins, β-lapachone, lenalidomide, irinotecan, maytansine, mechlorethamine, melphalan, 6-mercaptopurine, methotrexate, mitomycin C, nilotinib, oxaliplatin, paclitaxel, procarbazine, suberoylanilide hydroxamic acid (SAHA), 6-thioguanidine, thiotepa, teniposide, topotecan, trastuzumab, trichostatin A, vinblastine, vincristine, and vindesine.

Immunoconjugates of this invention can be formulated and administered using techniques conventional for biologic drugs. Formulations can include excipients, such as taught in Gennaro, ed., *Remington: The Science and Practice of Pharmacy*, 20th Ed. (Lippincott Williams & Wilkins 2003), the disclosure of which is incorporated herein by reference.

Exemplary excipients include, without limitation, buffering agents (e.g., phosphates, acetate, tris(hydroxymethyl)aminomethane (Tris)), solubilizers and emulsifiers (e.g., polysorbate), preservatives (e.g., thimerosal, benzyl alcohol), salts (e.g., NaCl, KCl) chelators (e.g., EDTA), carbohydrates (e.g., sucrose, dextrose, maltose, trehalose), carriers (e.g., albumin), amino acids and their respective hydrochloride salts, citrates, sorbitol, dextran, and the like.

The immunoconjugates can be provided as lyophilized powders with or without excipients, which can then be dissolved in a medium such as sterile water for injection, sodium chloride solution for injection, or dextrose solution for injection, with or without additional excipients.

Alternatively, the immunoconjugate can be provided as a concentrated solution, optionally including excipients, which is then diluted to the desired concentration prior to administration. Alternative forms include dispersions, microemulsion, and liposomes.

Preferably, a pharmaceutical composition is suitable for intravenous ("IV"), intramuscular, subcutaneous, parenteral, spinal or epidermal administration (e.g., by injection or infusion). The phrase "parenteral administration" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Preferred modes of administration include IV infusion, IV bolus, subcutaneous, and intramuscular.

A "therapeutically effective amount" preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective amount" preferably inhibits tumor growth by at least about 20%, more preferably by at least about 40%, even more preferably by at least about 60%, and still more preferably by at least about 80% relative to untreated subjects. A therapeutically effective amount of a therapeutic compound can decrease tumor size, or otherwise ameliorate symptoms in a subject, which is typically a human but can be another mammal.

Dosage regimens are adjusted to provide a therapeutic response. For example, a single dose may be administered, several divided doses may be administered over time, or the dose may be proportionally reduced or increased as indicated by the exigencies of the situation. It is especially advantageous to formulate parenteral compositions in dosage unit form for ease of administration and uniformity of dosage. "Dosage unit form" refers to physically discrete units suited as unitary dosages for the subjects to be treated; each unit containing a predetermined quantity of active compound calculated to produce the desired therapeutic response, in association with the required pharmaceutical carrier. Devices such as prefilled syringes, two-chamber syringes, and autoinjectors can be used.

The dosage will vary according to the disease being treated, patient traits such as age, gender, and genotype, and the stage of the treatment regimen. Typically, the dose can be from about 0.5 mg/kg to about 300 mg/kg.

EXAMPLES

The practice of this invention can be further understood by reference to the following examples, which are provided by way of illustration and not of limitation.

Example 1

Compound (IIa)

Figure 1B:
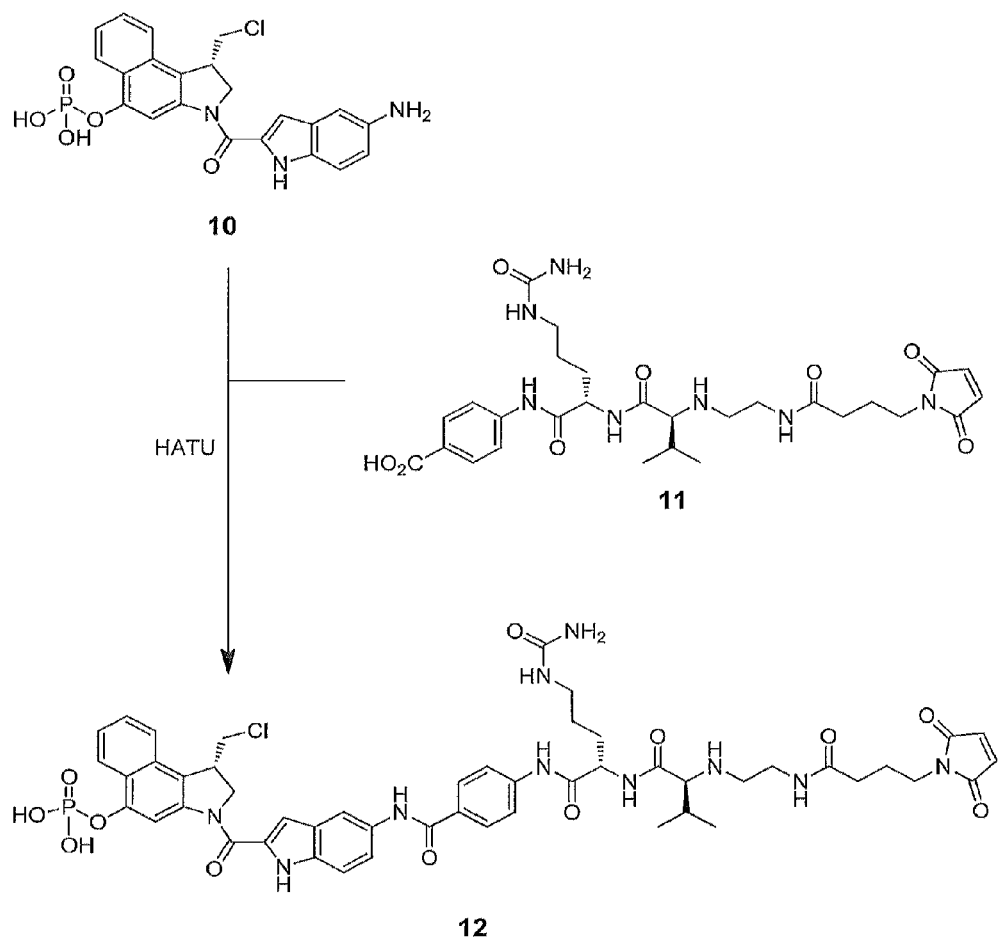

This example describes the synthesis of compound 12 of this invention (also referred to herein as compound (IIa)). FIGS. 1A and 1B combine to show the scheme for its synthesis.

Compound 2. Trifluoroacetic acid ("TFA," Fisher, 5 mL) was added to a solution of compound 1 (1 g, 2.36 mmol) in anhydrous dichloromethane ("DCM," Sigma-Aldrich, 5 mL). The reaction mixture was stirred at room temperature ("RT," circa 25° C.) for 30 min. High pressure liquid chromatography ("HPLC") analysis showed the reaction was complete. The reaction mixture was concentrated and dried under high vacuum overnight to yield 1.15 g of compound 2 as a greenish solid (TFA salt).

Compound 4. Di-tert-butyl dicarbonate ("(Boc)$_2$O," 10.24 g, 46.97 mmol) in anhydrous methanol (Acros, 100 mL) and palladium (Aldrich, 10% on activated carbon, 400 mg) were added to a suspension of ethyl 5-nitroindole-2-carboxylate (compound 3, Acros, 10 g, 42.7 mmol). The reaction mixture was hydrogenated under H$_2$ (30 psi) for 8 hr. The reaction mixture was filtered and the filtrate was concentrated and dried under high vacuum to yield compound 4 (10.5 g, 81%) as a yellow solid. $^1$HNMR (DMSO) δ 11.68 (s, 1 H), 9.19 (s, 1 H), 7.76 (s, 1H), 7.26 (m, 2 H), 7.02 (d, 1 H), 4.30 (q, 2 H), 1.46 (s, 9 H) 1.33 (t, 3 H).

Compound 5. A solution of LiOH monohydrate (Sigma-Aldrich) in water (150 mL, 0.57 M) was added to a solution of compound 4 (10.5 g, 34.5 mmol) in acetonitrile (150 mL). The reaction mixture was heated at 40° C. overnight, after which hydrolysis was complete per HPLC analysis. The reaction mixture was diluted with water (300 mL) and concentrated under vacuum to remove the acetonitrile. The resultant solution was extracted with EtOAc (2×150 mL) and the organic layers were discarded. The aqueous layer was acidified to pH 4 by adding 10% KHSO$_4$ (Aldrich) solution. The resultant mixture was again extracted with EtOAc (3×150 mL). The organic layers from the three later extractions were combined, dried over anhydrous MgSO$_4$ and concentrated under vacuum to yield compound 5 as a brown solid (9.7 g, 84%). $^1$HNMR (DMSO) δ 12.84 (s, 1 H), 11.65 (s, 1 H), 9.20 (s, 1 H), 7.73 (s, 1 H), 7.23 (m, 2 H), 6.92 (s, 1 H), 1.42 (s, 9 H); MS (ESI) m/z 299 (M+Na)$^+$.

Compound 6. A solution of compound 5 (779 mg, 2.83 mmol) and N,N,N',N'-tetramethyl-O-(7-azabenzotriazol-1-yl)uronium hexafluorophosphate ("HATU," Oakwood, 1.07 g, 2.83 mmol) in anhydrous N,N-dimethylformamide ("DMF," Sigma-Aldrich, 10 mL) was prepared. N,N-diisopropylethylamine ("DIPEA") was added to adjust the pH of the reaction solution to above 8. The reaction mixture was stirred at RT for 15 min. Crude compound 2 (1.15 g, estimated as 2.36 mmol) was added, followed by adding more DIPEA to adjust the pH of the reaction mixture to above 8. The reaction mixture was stirred at RT overnight. HPLC analysis showed the reaction was almost complete. The reaction mixture was diluted with EtOAc and washed with water and then brine. The organic phases were concentrated to a slurry with 2 g silica gel. The slurry was purified on a 40 g CombiFlash column with 0-50% EtOAc gradient in hexanes to yield compound 6 as a yellow solid (1.05 g, 76%). ¹HNMR (DMSO-d⁶): δ 11.61 (s, 1H), 9.18 (s, 1H), 8.22 (d, 1H), 8.16 (m, 1H), 7.95 (m, 1H), 7.81 (s, 1H), 7.58 (m, 3H), 7.42 (m, 3H), 7.33 (m, 3H), 7.15 (s, 1H), 5.15 (s, 2H), 4.82 (t, 1H), 4.59 (d, 1H), 4.30 (m, 1H), 4.04 (m, 1H), 3.90 (m, 1H), 1.48 (s, 9H).

Compound 7. A reaction mixture consisting of compound 6 (780 mg, 1.34 mmol) and Pd/C (Sigma-Aldrich, 10%, 150 mg) in anhydrous DCM (Sigma-Aldrich, 10 mL) and anhydrous methanol (5 mL) was stirred under a hydrogen balloon overnight. HPLC analysis showed that the reaction was complete. The reaction mixture was filtered through CELITE™ and the filtrate was concentrated to yield compound 7 as a slightly yellow solid (562 mg, 86%), which was used for next step without further purification.

Compound 9. A solution of compound 7 (260 mg, 0.53 mmol), di-tert-butyl diethylphosphoramidite (Sigma-Aldrich, 0.58 mL, 2.1 mmol) and tetrazole (Sigma-Aldrich, 0.45 M in acetonitrile, 14 mL) in tetrahydrofuran ("THF," Sigma-Aldrich, anhydrous, 25 mL) was stirred at RT for 2 hr. HPLC analysis showed staring material 7 was completely transformed to compound 8. Without isolating compound 8, a solution of m-chloroperbenzoic acid ("mCPBA," Sigma-Aldrich, 365 mg, 2.12 mmol) in DCM (anhydrous, Sigma-Aldrich, 10 mL) was added. The resulting reaction mixture was stirred at RT for 0.5 hr. HPLC analysis showed that the reaction was complete. The reaction mixture was concentrated with 0.5 g of silica gel to form a slurry. The slurry was purified on a 4 g CombiFlash column with 10-50% EtOAc gradient in hexane. The product-containing fractions were combined and dried under high vacuum to yield compound 9 as a white solid (212 mg, 59%).

Compound 10. TFA (Fisher, 3 mL) was added to a solution of compound 9 (212 mg, 0.031 mmol) in anhydrous DCM (Sigma-Aldrich, 3 mL). The reaction mixture was stirred at RT for 30 min. HPLC analysis showed that the reaction was complete. The reaction mixture was concentrated and dried under high vacuum overnight to yield compound 10 as greenish solid (271 mg). ¹HNMR of TFA salt (DMSO-d⁶): δ 11.81 (s, 1H), 8.42 (s, 1H), 8.12 (d, 1H), 7.94 (d, 1H), 7.55 (m, 1H), 7.42 (m, 3H), 7.18 (s, 1H), 7.02 (d, 1H), 4.78 (t, 1H), 4.68 (d, 1H), 4.32 (s, 1H), 4.02 (m, 1H), 3.90 (m, 1H).

Compound 12. The pH of a solution of compound 11 (179 mg, 0.25 mmol assuming mono-TFA salt, prepared per Sufi et al. 2010, the disclosure of which is incorporated herein by reference) and HATU (Oakwood, 84.4 mg, 0.222 mmol) in anhydrous DMF (Sigma-Aldrich, 3 mL) was adjusted to above 8 by the addition of DIPEA. The reaction mixture was stirred at RT for 15 min. HPLC analysis showed most of compound 11 was activated. Compound 10 (130 mg, 0.222 mmol assuming mono-TFA salt) was added to the reaction mixture. The pH was adjusted to above 8 by adding DIPEA. The reaction mixture was stirred at RT for 15 min. HPLC analysis showed the reaction was complete. The reaction mixture was injected into a preparative HPLC and purified with 10-100% acetonitrile gradient in water (with 0.1% TFA) as the eluent. The product-containing fractions were combined and lyophilized to yield compound 12 as a white solid (138 mg, 55%). MS: [M+H] 1055.

Those skilled in the art will appreciate that the synthesis described above and in FIGS. 1A and 1B involves the convergent assembly of precursors of fragments a and a' and that alternative synthetic strategies may be employed, for instance through the assembly of precursors to fragments b, b' and b" or fragments c, c', and c" as shown below. The latter two strategies are illustrated in Sufi et al. 2010, the disclosure of which is incorporated by reference and can be adapted for the synthesis of compounds of this invention, mutatis mutandis.

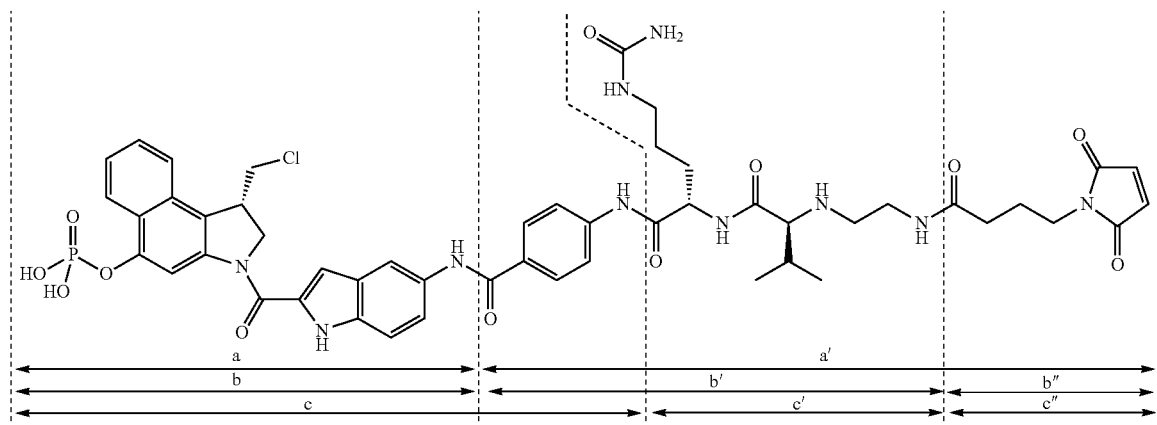 [SMILES: CC(C)[C@H](NCCNC(=O)CCCN1C(=O)C=CC1=O)C(=O)N[C@@H](CCCNC(N)=O)C(=O)Nc1ccc(C(=O)Nc2ccc3[nH]c(C(=O)N4C[C@@H](CCl)c5c4cc(OP(=O)(O)O)c4ccccc54)cc3c2)cc1]

Example 2

Compound (Ia)

Figure 2:
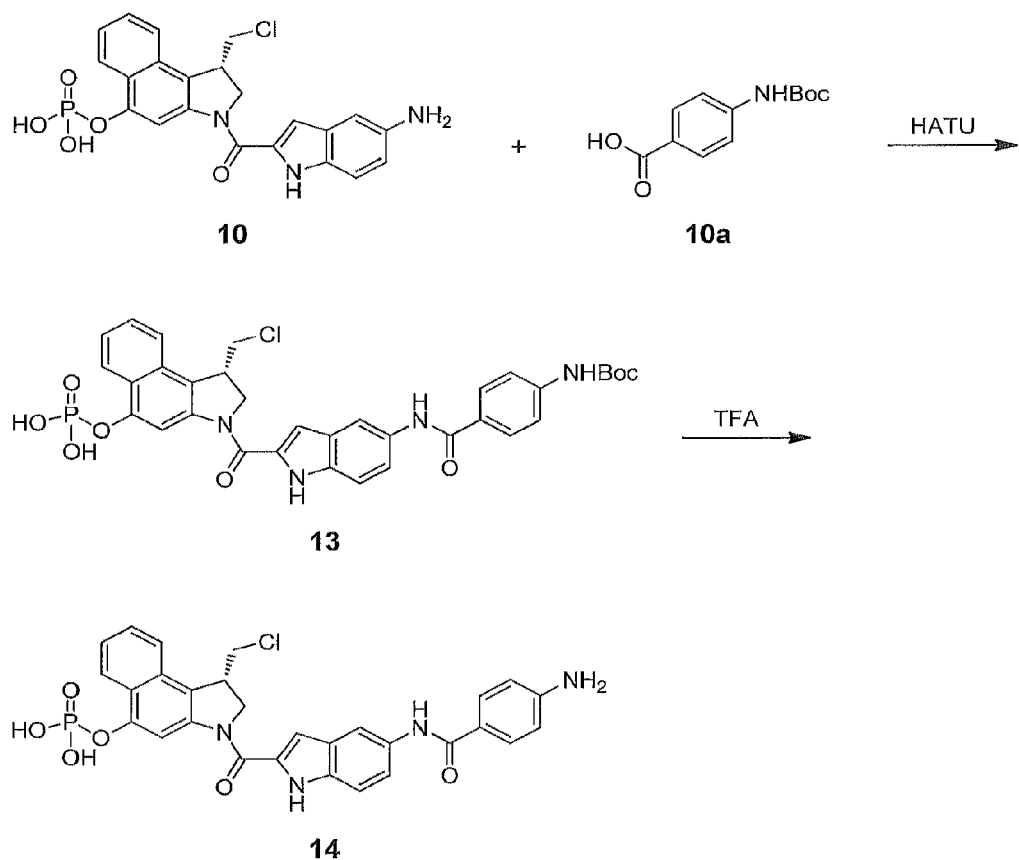

This Example relates to the synthesis of compound 14, also referred to herein as compound (Ia). The schematic for the synthesis is shown in FIG. 2.

Compound 13. DIPEA (Aldrich, 17 μL, 01 mmol) was added to a solution of compound 10a (Sigma-Aldrich, 15.7 mg, 0.051 mmol) and HATU (Oakwood, 19.4 mg, 0.051 mmol) in anhydrous DMF (Acros, 1 mL) The pH of reaction mixture was above 8. The reaction mixture was stirred at RT for 15 min. HPLC analysis showed starting material was completely activated. Compound 10 (30 mg, 0.051 mmol assuming mono-TFA salt) was added to this solution. More DIPEA was added to adjust the pH of the reaction mixture to above 8. The reaction mixture was stirred at RT for 1 hr. HPLC analysis showed the reaction was complete. The crude product was purified by preparative HPLC with 10-100% acetonitrile gradient in water (with 0.1% TFA by volume) as the eluent to yield compound 13 (25 mg, 71%) as an off-white solid.

Compound 14. TFA (VWR, 1 mL) was added to a solution of compound 13 (25 mg, 0.036 mmol) in anhydrous DCM (Acros, 1 mL). The reaction mixture was stirred at RT for 30 min. HPLC analysis showed that the reaction was complete. The reaction mixture was concentrated and purified by preparative HPLC with 10-65% acetonitrile gradient in water (with 0.1% TFA by volume) as the eluent to yield compound 14 (21 mg, 82% assuming mono-TFA salt) as an off-white solid. $^1$HNMR (DMSO-d$^6$): δ 11.65 (s, 1H), 9.67 (s, 1H), 8.46 (s, 1H), 8.07 (d, 2H), 7.91 (m, 2H), 7.69 (d, 2H), 7.35-7.55 (m, 4H), 7.15 (s, 1H), 6.57 (d, 2H), 4.82 (t, 1H), 4.57 (d, 1H), 4.03 (t, 1H), 3.954 (t, 1H). $^{31}$PNMR (DMSO-d$^6$): δ −5.909 (s, 1P), MS: [M+H] 591.

Example 3

Compound (IIb)

FIGS. 3A-3D show in combination the synthesis of compound 28, also referred to herein as compound (IIb). Those skilled in the art will appreciate that the general strategy employed here corresponds to the b/b'/b" pattern described above in Example 1.

Figure 3A:
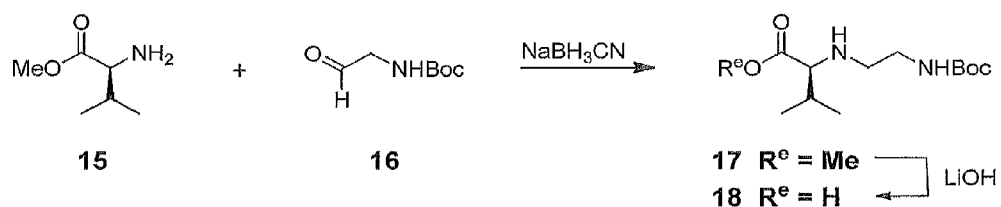

FIG. 3A shows the synthesis of a first intermediate compound 18.

Compound 17. A solution of tert-butyl (2-oxoethyl)carbamate (compound 16, Aldrich, 5 g, 31.4 mmol) in methanol (anhydrous, Acros, 15 mL) was added to a solution of (S)-methyl 2-amino-3-methylbutanoate (compound 15, BaChem, HCl salt, 5.26 g, 31.4 mmol), NaOAc (Aldrich, 10.3 g, 82.06 mmol) in methanol (anhydrous, Acros, 65 mL). Then NaBH$_3$CN (Aldrich, 3.95 g, 62.8 mmol) was added. The reaction mixture was stirred at 22.5° C. for 16 hr and concentrated to a slurry. The slurry was dissolved in water (100 mL) and the resultant solution was extracted with EtOAc (3×100 mL). The organic phases were combined, washed with brine (1×100 mL), concentrated, and dried under vacuum to yield compound 17 (oil, 9.4 g crude). [M+H] 275.

Compound 18. A solution of LiOH hydrate (Aldrich, 2.88 g, 68.6 mmol) in water (40 mL) was added to a solution of crude compound 17 (9.4 g) in methanol (40 mL). The reaction mixture was stirred at RT overnight and diluted with water (40 mL). The resultant solution was extracted with DCM (40 mL). The aqueous layer was separated and acidified with KHSO$_4$ solution (Aldrich, 20% in water) to pH 5. The suspension was filtered and the solid was dried under high vacuum to yield compound 18 (4.85 g, 60.2% from compound 15) as a white solid. MS: [M+H] 261. $^1$HNMR (DMSO-d$^6$) δ 6.82 (t, 1 H), 3.06 (m, 2 H), 2.83 (d, 1 H), 2.62 (m, 2 H), 2.31 (m 1 H), 1.88 (m, 1 H), 1.38 (s, 9 H), 0.86 (d, 6 H).

Figure 3B:
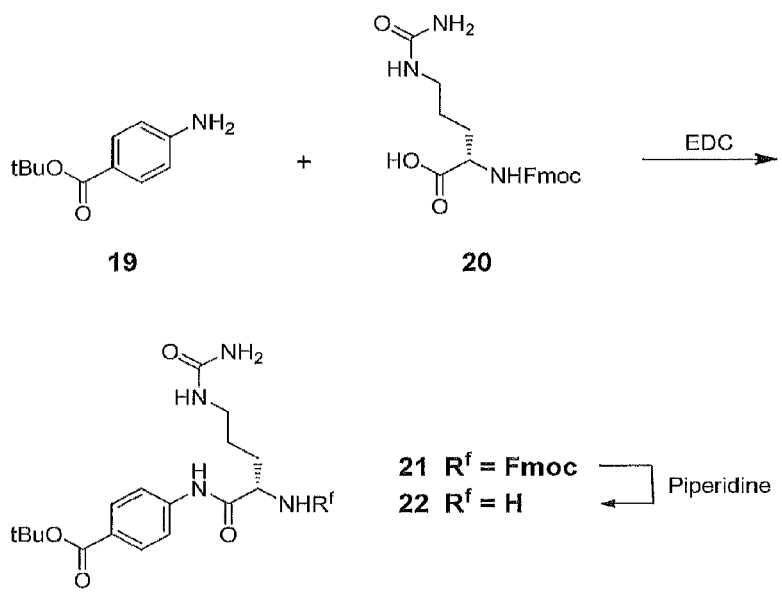

FIG. 3B shows the synthesis of a second intermediate compound 22.

Compound 21. tert-Butyl 4-aminobenzoate (compound 19, Fluka, 8.75 g, 45.3 mmol), N-(3-dimethylaminopropyl)-N'-ethylcarbodiimide hydrochloride ("EDC," Fluka, 8.68 g, 45.3 mmol), 1-hydroxybenzotriazole (Chem-Impex, 6.12 g, 45.3 mmol) in anhydrous DMF (Acros, 150 mL), and CuCl$_2$ (Aldrich, 6.08 g, 45.3 mmol) were added to a solution of N$_α$-Fmoc-L-citrulline (compound 20, Fluka, 15 g, 37.74 mmol). The reaction mixture was stirred at RT overnight. The reaction mixture was diluted with EtOAc (600 mL) and the resultant solution was washed with Na$_2$CO$_3$ solution (5%, 200 mL), saturated NaHCO$_3$ solution (1×200 mL), and brine (1×200 mL). The combined organic phases were dried over anhydrous MgSO$_4$ and concentrated to yield crude compound 21 as a yellow solid. $^1$HNMR (DMSO-d$_6$) δ 10.39 (s, 1 H), 7.82 (q, 4 H), 7.68 (m, 4 H), 7.28-7.40 (m, 5 H), 6.01 (t, 1 H), 5.42 (s, 2 H), 4.10-4.29 (m, 4 H), 2.90-3.05 (m, 2 H), 1.32-1.70 (m, 13 H); MS: [M+H] 573.

Compound 22. Piperidine (Aldrich, 14 mL) was added to a solution of crude compound 21 in anhydrous DMF (Acros, 140 mL). The reaction mixture was stirred at RT for 1 hr. HPLC analysis showed the reaction was complete. The reaction mixture was concentrated and the residue was dissolved in EtOAc (600 mL). The organic phase was washed with brine (1×200 mL), dried over anhydrous MgSO$_4$, and concentrated with silica gel to a slurry. The slurry was purified by flash chromatography with 0-20% methanol gradient in DCM as the eluent to yield compound 22 as a white solid (9.5 g, 72% yield from compound 20). $^1$HNMR (DMSO-d$_6$) δ 7.82 (d, 2 H), 7.72 (d, 2 H), 5.97 (t, 1 H), 5.38 (s, 2 H), 3.43 (m, 1 H), 2.98 (t, 2 H), 1.30-1.62 (m, 13 H); MS: [M+H] 351.

Figure 3C:
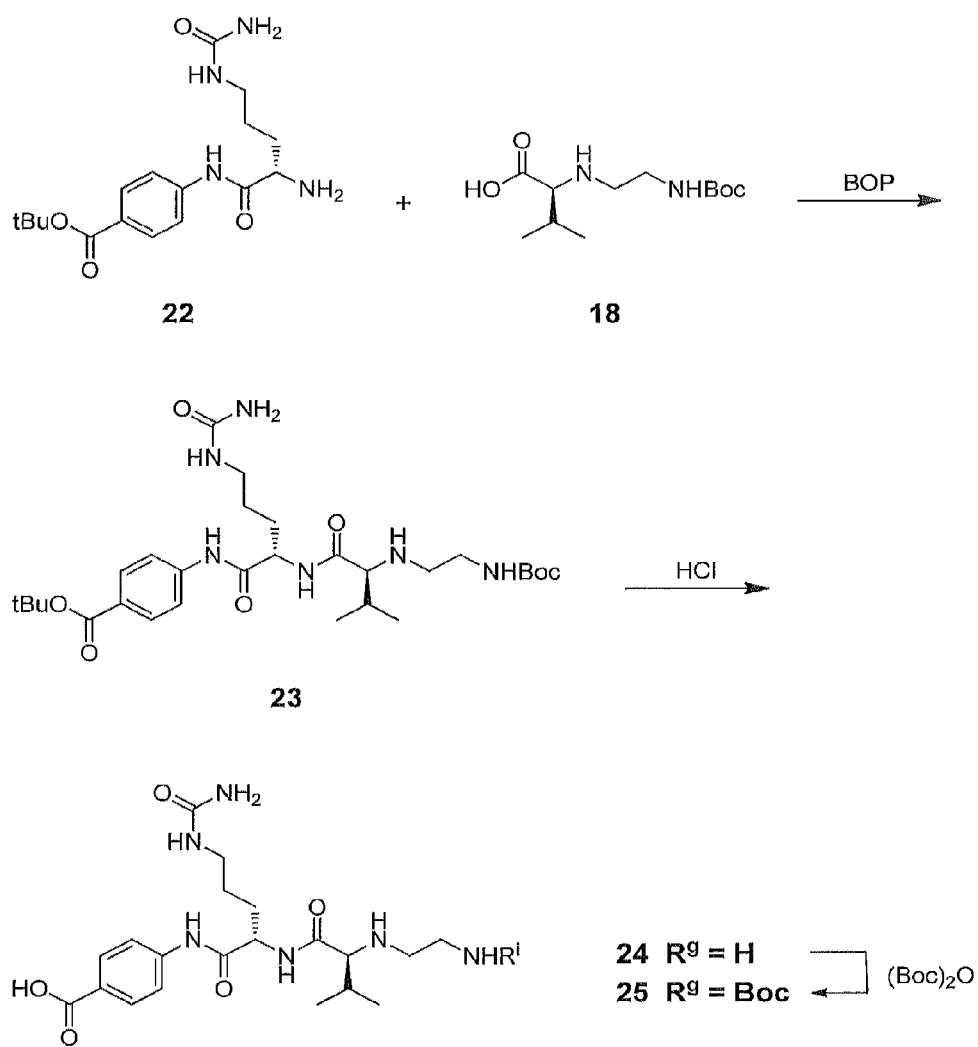

FIG. 3C shows the synthesis of a third intermediate compound 25.

Compound 23. DIPEA (Aldrich) was added to a solution of compound 18 (1.5 g, 5.77 mmol), benzotriazol-1-yloxy-tris (dimethylamino)-phosphonium hexafluorophosphate ("BOP," BaChem, 2.87 g, 6.5 mmol) and compound 22 (1.84 g, 5.26 mmol) in DMF (Acros, anhydrous, 15 mL), in an amount sufficient to adjust the pH of the solution to above 8. The reaction mixture was stirred at RT for 3 hr. HPLC analysis showed the reaction was complete. DCM (100 mL) and saturated NaHCO$_3$ solution (100 mL) were added to the reaction mixture. The aqueous layer was extracted with DCM (2×25 mL) The organic phases were combined and concentrated with silica gel (8 g) to a slurry. The slurry was purified on an 80 g CombiFlash column with 0-10% methanol gradient in DCM as the eluent. The product-containing fractions were combined, concentrated, and dried under high vacuum to yield compound 23 as a white solid (2.1 g, 68%). MS: [M+H] 593.

Compound 24. HCl in dioxane (Aldrich, 4 N, 7 mL) was added to a solution of compound 23 (1.8 g, 3.03 mmol) in acetonitrile (HPLC grade, Aldrich, 20 mL). The reaction mixture was stirred at RT for 3 hr. HPLC analysis showed the reaction was complete. The product was collected by filtration and dried under high vacuum overnight to yield compound 24 as an almost white solid (1.45 g, 94%). MS: [M+H] 437.

Compound 25. DIPEA was added to a solution of compound 24 (200 mg, 0.39 mmol, assuming a double HCl salt) and (Boc)$_2$O (94.2 mg, 0.43 mmol) in DMF (anhydrous, 2 mL), in an amount sufficient to adjust the pH of the reaction mixture to above 8. The reaction mixture was stirred at RT for 2 hr. HPLC analysis showed the reaction was complete. Diethyl ether (20 mL) was added and the mixture was stirred at RT for 15 min. The product separated as a semi-solid. The solvent was decanted and the product was dried under high vacuum overnight to yield compound 25 as a white solid (178 mg, 85%, HCl salt). MS: [M+H] 537. $^1$HNMR (DMSO-d$_6$) δ 10.51 (s, 1 H), 8.85 (b, 1 H), 7.88 (d, 2 H), 7.71 (d, 2 H), 7.03 (b, 1 H), 6.18 (d, 1 H), 5.42 (b, 2 H), 4.48 (s, 1 H), 2.75-3.10 (m, 7 H), 2.18 (b, 1 H), 1.42-1.78 (m. 4 H), 1.38 (s, 9 H), 0.92 (m, 6 H).

Figure 3D:
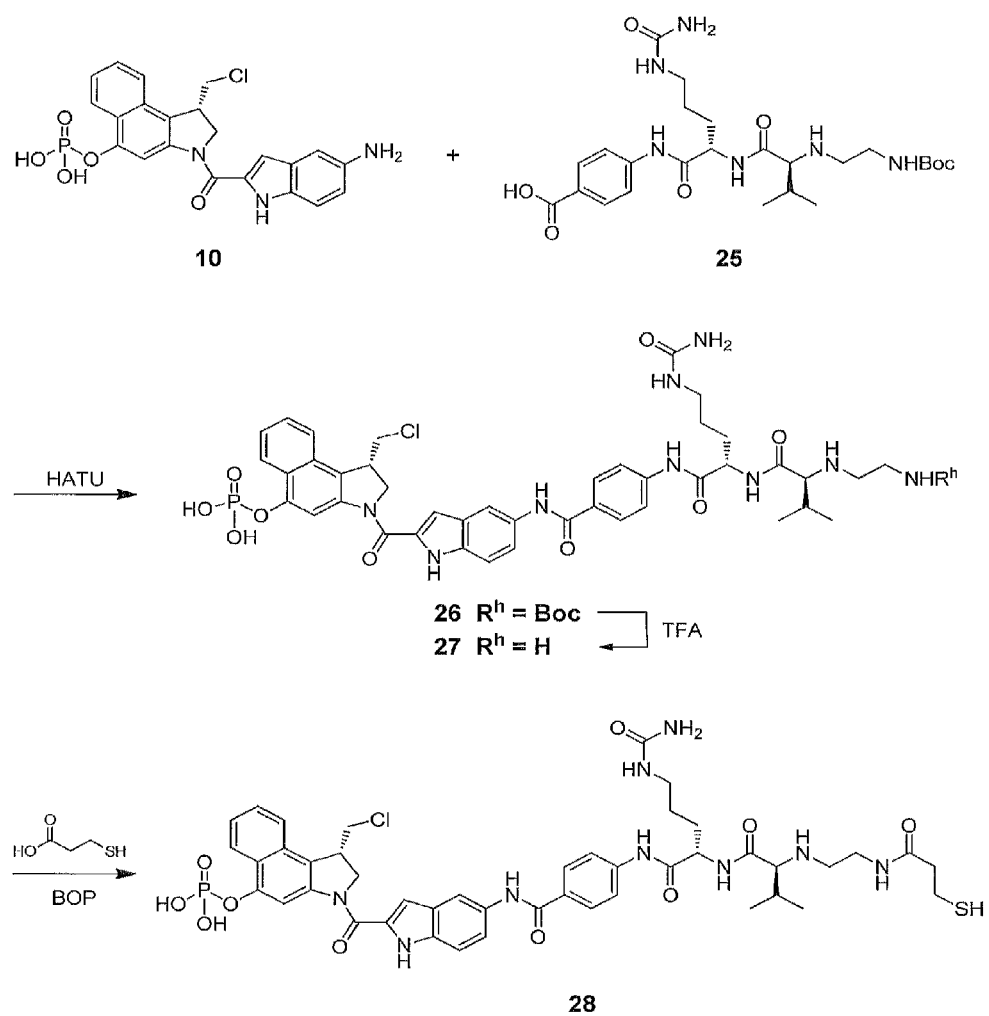

FIG. 3D shows the completion of the synthesis of compound 28, also referred to herein as compound (IIb).

Compound 26. DIPEA (Aldrich, 0.142 mL, 0.816 mmol) was added to a solution of compound 25 (394 mg, 0.734 mmol) and HATU (Oakwood, 186 mg, 0.489 mmol) in DMF (Acros, anhydrous, 3 mL). The pH of the reaction mixture was above 8. The reaction mixture was stirred at RT for 15 min. Compound 10 (Example 1, 192 mg, 0.407 mmol) was added. More DIPEA was added to keep the pH of reaction mixture above 8. The reaction mixture was stirred at RT for 30 min. The reaction mixture was injected into a preparative HPLC and purified by elution with 10-65% acetonitrile gradient in water (with 0.1% TFA). The product-containing fractions were combined and freeze-dried to yield compound 26 (205 mg, 51%) as a white solid. MS: [M+H] 990.

Compound 27. TFA (VWR, 5 mL) was added to a solution of compound 26 (205 mg, 0.207 mmol) in DCM (Acros, anhydrous, 5 mL). The reaction mixture was stirred at RT for 30 min. The reaction mixture was concentrated and freeze-dried to yield compound 27 as its TFA salt (210 mg, 100%). MS: [M+H] 890.

Compound 28. DIPEA (Aldrich, 0.147 mL, 0.842 mmol) was added to a solution of 3-mercaptopropanoic acid (Aldrich, 59.6 mg, 0.562 mmol), compound 27 (100 mg, 0.112 mmol) and BOP (Aldrich, 124 mg, 0.281 mmol) in DMF (Acros, anhydrous, 2 mL). The pH of the reaction mixture was above 8. The reaction mixture was stirred at RT for 1 hr. The reaction mixture was injected into a preparative HPLC and purified by elution with 10-65% acetonitrile gradient in water (with 0.01% TFA) to yield compound 28 (45 mg, 45.5%). MS: [M+H] 978.

Example 4

Preparation of Immunoconjugates

The following is an illustrative general procedure for the preparation of immunoconjugates of this invention, based on introduction of free thiol groups into an antibody by reaction of lysine ε-amino groups with 2-iminothiolane, followed by reaction with a maleimide-containing prodrugged moiety such as compound (IIa). Initially the antibody is buffer exchanged into 0.1 M phosphate buffer (pH 8.0) containing 50 mM NaCl and 2 mM diethylene triamine pentaacetic acid ("DTPA") and concentrated to 5-10 mg/mL Thiolation is achieved through addition of 2-iminothiolane to the antibody. The amount of 2-iminothiolane to be added can be determined by a preliminary experiment and varies from antibody to antibody. In the preliminary experiment, a titration of increasing amounts of 2-iminothiolane is added to the antibody, and following incubation with the antibody for 1 h at RT 25° C.), the antibody is desalted into 50 mM pH 6.0 HEPES buffer using a SEPHADEX™ G-25 column and the number of thiol groups introduced determined rapidly by reaction with dithiodipyridine ("DTDP"). Reaction of thiol groups with DTDP results in liberation of thiopyridine, which can be monitored spectroscopically at 324 nm. Samples at a protein concentration of 0.5-1.0 mg/mL are typically used. The absorbance at 280 nm can be used to accurately determine the concentration of protein in the samples, and then an aliquot of each sample (0.9 mL) is incubated with 0.1 mL DTDP (5 mM stock solution in ethanol) for 10 min at RT. Blank samples of buffer alone plus DTDP are also incubated alongside. After 10 min, absorbance at 324 nm is measured and the number of thiol groups is quantitated using an extinction coefficient for thiopyridine of 19,800 $M^{-1}$.

Typically a thiolation level of about three thiol groups per antibody is desirable. For example, with some antibodies this can be achieved by adding a 15-fold molar excess of 2-iminothiolane followed by incubation at RT for 1 h. The antibody is then incubated with 2-iminothiolane at the desired molar ratio and then desalted into conjugation buffer (50 mM pH 6.0 HEPES buffer containing 5 mM glycine and 2 mM DTPA). The thiolated material is maintained on ice while the number of thiols introduced is quantitated as described above.

After verification of the number of thiols introduced, the drug-linker moiety is added at a 3-fold molar excess per thiol. The conjugation reaction is allowed to proceed in conjugation buffer also containing a final concentration of 5% dimethyl-sulfoxide (DMSO), or similar alternative solvent. Commonly, the drug-linker stock solution is dissolved in 100% DMSO. The stock solution is added directly to the thiolated antibody, which has enough DMSO added to bring the final concentration to 10%, or pre-diluted in conjugation buffer containing a final concentration of 10% DMSO, followed by addition to an equal volume of thiolated antibody.

The conjugation reaction mixture is incubated at RT for 2 h with stirring. Following incubation, the conjugation reaction mixture is centrifuged and filtered through a 0.2 μm filter. Purification of the conjugate can be achieved through chromatography using a number of methods. In one method, the conjugate is purified using size-exclusion chromatography on a SEPHACRYL™ S200 column pre-equilibrated with 50 mM pH 7.2 HEPES buffer containing 5 mM glycine and 50 mM NaCl. Chromatography is carried out at a linear flow rate of 28 cm/h. Fractions containing conjugate are collected, pooled and concentrated. In an alternative method, purification can be achieved through ion-exchange chromatography. Conditions vary from antibody to antibody and should to be optimized in each case. For example, antibody-drug conjugate reaction mix is applied to an SP-SEPHAROSE™ column pre-equilibrated in 50 mM pH 5.5 HEPES containing 5 mM glycine. The antibody conjugate is eluted using a gradient of 0-1 M NaCl in equilibration buffer at pH 5.5. Relevant fractions containing the immunoconjugate are pooled and dialyzed against formulation buffer (50 mM pH 7.2 HEPES buffer containing 5 mM glycine and 100 mM NaCl).

Following the above procedure, immunoconjugates of compound (IIa) were prepared with an anti-PSMA human monoclonal antibody (2A10, Huang et al. 2009 and Cardarelli et al. 2011); an anti-mesothelin human monoclonal antibody (6A4, Terrett et al. 2009b), an anti-CD70 human monoclonal antibody (2H5, Terrett et al. 2009a), and an anti-CD19 human monoclonal antibody (21D4, Rao-Naik et al. 2009). Comparative immunoconjugates with compound (A) was likewise prepared.

Those skilled in the art will understand that the above-described conditions and methodology are exemplary and non-limiting and that other approaches for conjugation are known in the art and usable in the present invention.

Example 5

$^3$H-Thymidine Incorporation Assays

This example generally describes the procedure used to assay the antiproliferative activity of immunoconjugates of this invention. Human tumor cell lines were obtained from the American Type Culture Collection (ATCC), P.O. Box 1549, Manassas, Va. 20108, USA, and cultured according to ATCC instructions. CHO-Meso cells were generated by transfecting CHO cells with DNA containing human Mesothelin gene and selecting for stable clones expressing human Mesothelin. Cells were seeded at $1.0 \times 10^4$ cells/well in 96-well plates for 3 hr for $^3$H thymidine assays, respectively. Serial dilutions (1:3) of immunoconjugates were added to the wells. Plates were allowed to incubate for 72 hr. The plates were pulsed with 1.0 μCi of $^3$H-thymidine per well for the last 24 hr of the total incubation period, harvested, and read on a Top Count Scintillation Counter (Packard Instruments, Meriden, Conn.). The $EC_{50}$ values—the concentration at which an agent inhibits or reduces cell proliferation by 50% of the maximum inhibition—were determined using PRISM™ software, version 4.0 (GraphPad Software, La Jolla, Calif., USA).

Antiproliferative results are shown in FIG. 4A-4F, discussed hereinabove.

Example 6

Dephosphorylation by Cell Lysates

This example demonstrates that phosphate prodrugged seco-MGBA compounds according to this invention can be dephosphorylated by human tumor cell lysates.

786-O cells, as frozen pellets with an estimated quantity of $10^7$ cells per vortexing tube, were resuspended and homogenized in 500 µL of lysis buffer (25 mM NaOAc, 1 mM EDTA, 0.25 M sucrose, 0.1% Triton X-100, pH 5.5). Homogenization involved vortex mixing for 30 sec, followed by a one min cooling on ice. For each tube, three vortex and cooling cycles were performed. Cell samples were then further mixed by shearing in a 19 gauge needle three times.

Following homogenization, the DNA of the cell lysate was hydrolyzed using BENZONASE™ DNAse. Samples were first brought up in 1 mM MgSO$_4$. After mixing, 2 µL of BENZONASE™ DNAse (neat) were added to each vial of lysate (4 µL/mL, v/v, final concentration). Samples were then stored at RT for 15 min and then cooled on ice. For this step, successful DNAse activity was evidenced by appearance of flocculent precipitate. Samples were then spun at maximum speed in a microcentrifuge for 5 min to remove cellular debris. Supernatant was frozen at −70° C. for later use. Protein concentration of the lysate was determined using Pierce BCA Protein Determination methodology (Thermo Scientific). Samples in this study were found to contain 2.85 mg/mL protein.

A 2000 µM stock solution of the compound of formula (Ia) was prepared. Lysate was diluted to 2.1 mg/mL in lysate buffer. For reaction, 5 µL of the compound (Ia) stock was added to 95 µL of lysate. Final concentrations were 100 µM compound (Ia) in lysate containing 2 mg/mL of protein. A buffer containing 25 mM NaOAc, 1 mM EDTA, 0.25 M sucrose, 0.1% Triton X 100, and 1 mM MgSO$_4$ provided buffering at pH 5.5.

Negative controls were employed, with lysate buffer in place of cell lysate, with BENZONASE™ DNAse and MgSO$_4$ also added.

Test samples and controls were placed in a hot block set at 37° C. At predetermined time intervals (5 min, 1 hr, 2 hr, 4 hr, and 8 hr), 50 µL aliquots were removed, and the reaction in each aliquot stopped by the addition of 150 µL (3×) of cold ethanol. Samples were stored on ice for one hour and centrifuged to remove protein. The supernatant was reserved for HPLC analysis, under the following conditions:

Column: Waters HSS T3 2.1×50 mm C18 HPLC

Mobile phase: "A" Buffer: water/0.1% TFA; "B" Buffer: Acetonitrile/0.1% TFA

HPLC system: Waters HPLC

Injection volume: 4 µL

Elution: 25 to 40% "B", in 1.8 min

Flow Rate: 1 mL/min

Detection: A340

Reaction was followed by monitoring for the production of compounds (IVa) and (IVb), which are the seco and cyclopropyl forms of dephosphorylated compound (Ia), respectively.

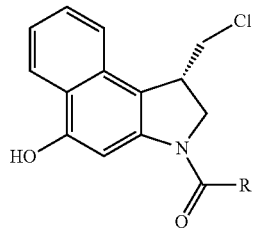

(IVa)

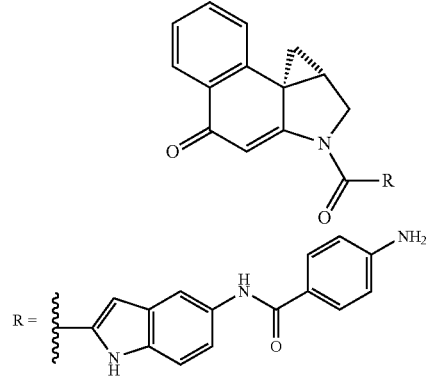

(IVb)

Dephosphorylation was found to be quite rapid, being complete within 8 hr. Since the pH of the reaction mixture was 5.5, approximating that found in lysosomal organelles, the results implicate acid phosphatase in the dephosphorylation reaction.

A similar experiment was conducted, using H226 cell lysates. Dephosphorylation was found to be complete within 3 hr.

Example 7

Dephosphorylation by Liver Microsomes

This example demonstrates the dephosphorylation of compound (Ia) by human and mouse liver microsome enzymes.

Human liver microsomes derived from pooled liver sources were obtained from Xenotech (Part Number H-0630). They were supplied at a nominal protein concentration of 20 mg/mL in a 20% sucrose solution. Protein content was verified with BCA analysis using reagent from Thermo-Fisher.

Human liver microsomes were diluted to 8.42 mg/mL in reaction buffer (100 mM Tris-HCl, 1 mM MgCl$_2$ 0.9% NaCl, pH 7.4). Dilution quantity was designed to deliver exactly 0.8 mg per 95 µL of a final 100 µL reaction volume. Stock was then serially diluted at 1:1 volume to volume, producing ten stock solutions for delivering between 8 and 0.0156 mg/mL of microsomes per stock solution.

A 2000 µM stock solution of the compound of formula (Ia) was prepared. For reactions, 95 µL of each microsome stock was allowed to equilibrate in a 37° C. hot block. A 5 µL aliquot of the compound (Ia) stock solution was then added to each reaction vial in precisely staggered 30 sec intervals. The final compound (Ia) concentration was 100 µM. Samples were allowed to react at temperature for 1 hr, after which reaction was stopped with the addition of 100 µL of cold ethanol. Stop was performed again in precise 30 second intervals, such that each vial was allowed to react for exactly 1 hour. Samples were prepared in duplicate. Protein was allowed to precipitate on ice for 30 min. The supernatant was collected following centrifugation. HPLC chromatographic analysis was performed using the same conditions as described in the previous example, again monitoring for the production of compounds (IVa) and (IVb). Chromatographic traces showing the conversion of compound (Ia) to compounds (IVa) and (IVb) as a function of microsome concentration are shown in FIG. 5.

Figure 6:
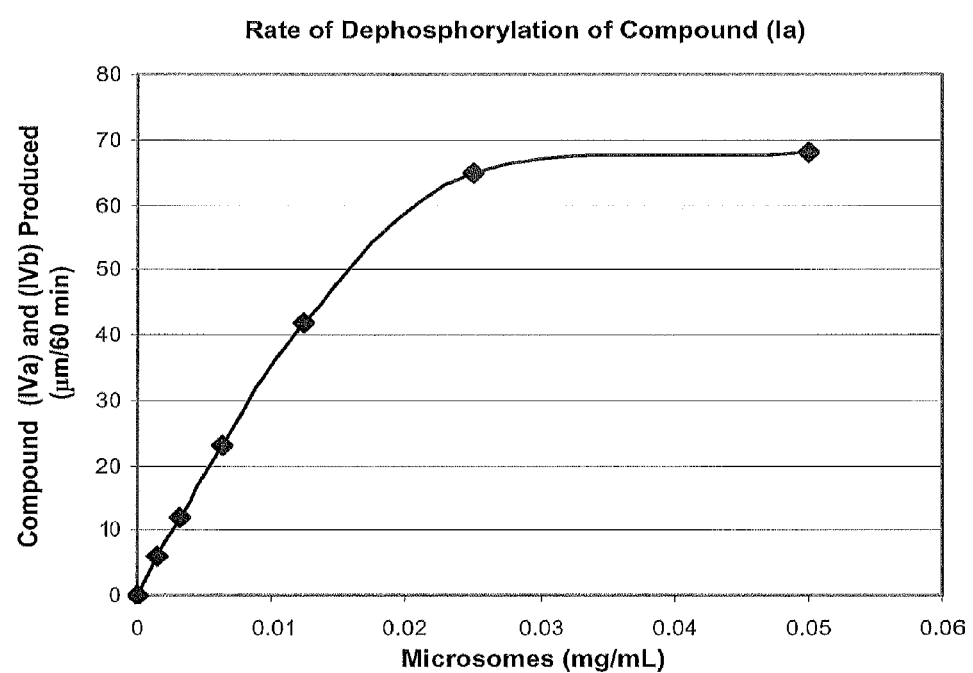
FIG. 6 is a plot of the amount of dephosphorylated product produced as a function of microsome concentration, over a period of one hour.

FIG. 6 is a plot of the amount of compounds (IVa) and (IVb) produced from compound (Ia) after 60 mM as a function of microsome concentration. The rate of production was essentially linear for microsome concentrations between 0.00156 and 0.0125 mg/mL. Using the data in this range, a rate for the production of compounds (IVa) and (IVb) of 0.0054 µmol/min/mg was calculated.

Employing the same procedure but with mouse liver microsomes (Xenotech, Part No. M-3000), a rate of 0.0018 µmol/min/mg was obtained.

Example 8

Compound (IIc)

Figure 7:
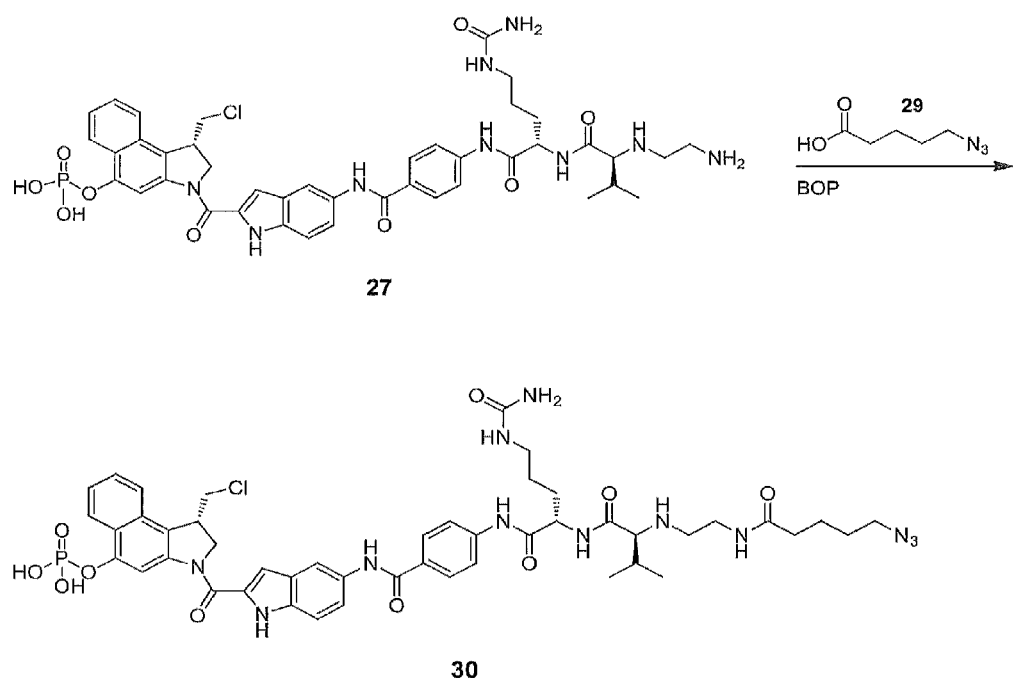
FIG. 7 shows the synthesis of yet another compound of this invention, having an azide reactive functional group for conjugation to an antibody.

This example and FIG. 7 describe the synthesis of compound 30, also referred to herein as compound (IIc).

Compound 30. DIPEA (Aldrich, 7.85 µL, 0.045 mmol) was added to a solution of compound 27 (20 mg, 0.022 mmol), 5-azidopentanoic acid 29 (BaChem, 6.43 mg, 0.045 mmol) and BOP (Aldrich, 19.87 mg, 0.045 mmol) in DMF (Acros, anhydrous, 0.5 mL). The pH of the reaction mixture remained above 8. The reaction mixture was stirred at RT for 1 h. The reaction mixture was injected into a preparative HPLC column and purified by elution with 10-65% acetonitrile gradient in water (with 0.1% TFA) to yield compound 30 (5 mg, 21.9%). MS: [M+H] 1015.

Compound 30 (IIc) has an azido reactive functional group, making it suitable for conjugation employing "click" chemistry.

Example 9

Compound (IId)

Figure 8:
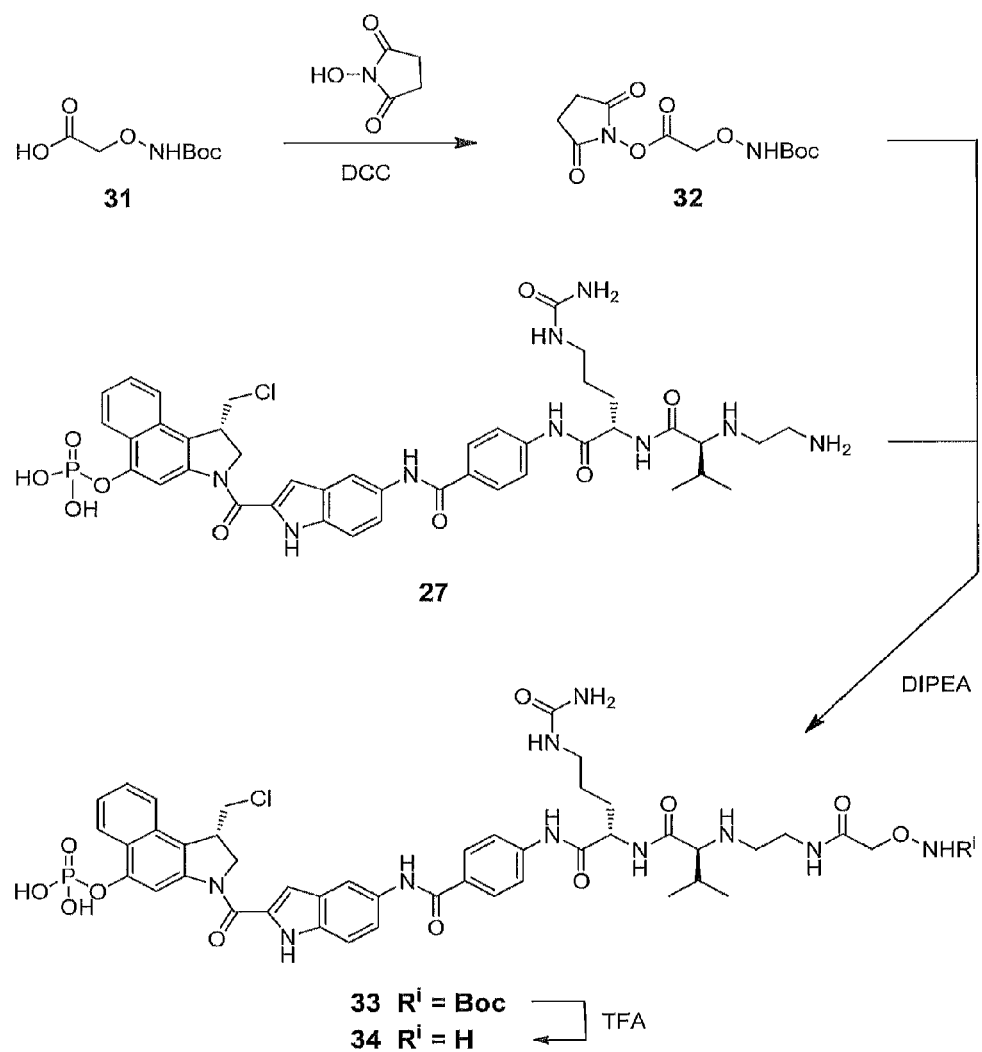
FIG. 8 shows the synthesis of yet another compound of this invention, having a hydroxylamine reactive functional group for conjugation to an antibody.

This example and FIG. 8 describe the synthesis of compound 34, also referred to herein as compound (IId).

Compound 32. Dicyclohexylcarbodiimide ("DCC," Novabiochem, 277 mg, 1.098 mmol) was added to a solution of 1-hydroxypyrrolidin-2,5-dione (Acros, 126 mg, 1.098 mmol), (Boc-aminoxy)acetic acid 31 (TCI, 200 mg, 1.046 mmol) in 1,4-dioxane (Aldrich, anhydrous, 2 mL). The reaction mixture was stirred at RT for 5 h. The reaction mixture was filtered through CELITE™ and the filtrate was concentrated. The residue was dissolved in EtOAc (30 mL), washed with saturated NaHCO$_3$ solution (20 mL) and water (20 mL). The organic phases were concentrated and dried under high vacuum to yield compound 32 (275 mg, 91.2%). $^1$H NMR (400 MHz, CDCl$_3$): δ 7.66 (s, 1H), 4.78 (s, 2H), 2.87 (s, 4H), 1.49 (s, 9H).

Compound 33. DIPEA (Aldrich, 36.5 µL, 0.21 mmol) was added to a solution of compound 32 (20 mg, 0.07 mmol) and compound 27 (31 mg, 0.035 mmol) in DMF (Aldrich, anhydrous, 1 mL). The reaction mixture was stirred at RT for 1 h. The reaction mixture was purified by preparative HPLC with 10-65% acetonitrile gradient in water (with 0.1% TFA). The product-containing fractions were combined and freeze-dried to yield compound 33 (24 mg, 64.5%). MS: [M+H] 1063.

Compound 34. TFA (Acros, 0.5 mL) was added to a solution of compound 33 (24 mg, 0.023 mmol) in DCM (Aldrich, anhydrous, 0.5 mL). The reaction mixture was stirred at RT for 0.5 h. The reaction mixture was purified by preparative HPLC with 10-65% acetonitrile gradient in water (with 0.1% TFA). The product-containing fractions were combined and freeze-dried to yield compound 34 (10 mg, 45.7%). MS: [M+H] 963.

Compound 34 (IId) has a hydroxylamine reactive functional group, making it suitable for conjugation by oxime formation with an antibody modified to contain a ketone group, for example by the incorporation of the non-natural amino acid p-acetylphenylalanine.

Example 10

Compound (IIe)

Figure 9A:
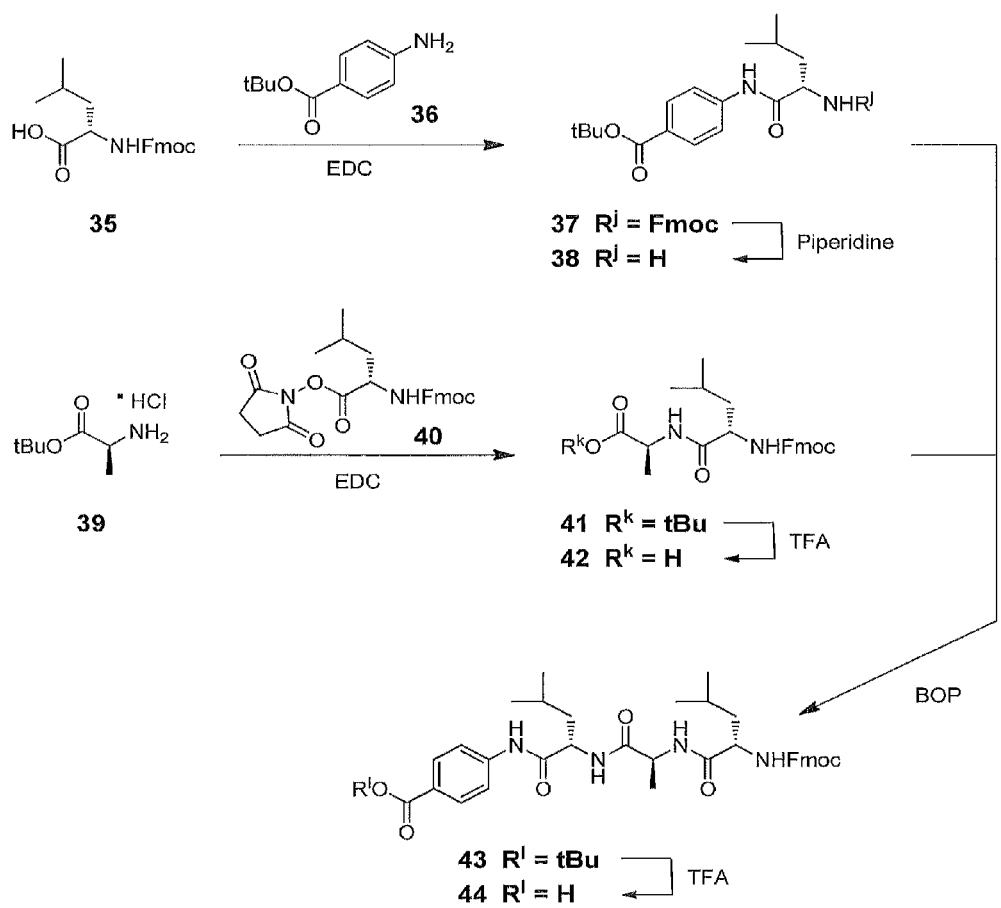
FIGS. 9A and 9B show in combination the synthesis of a compound of this invention, having a Leu-Ala-Leu tripeptide.
Figure 9B:
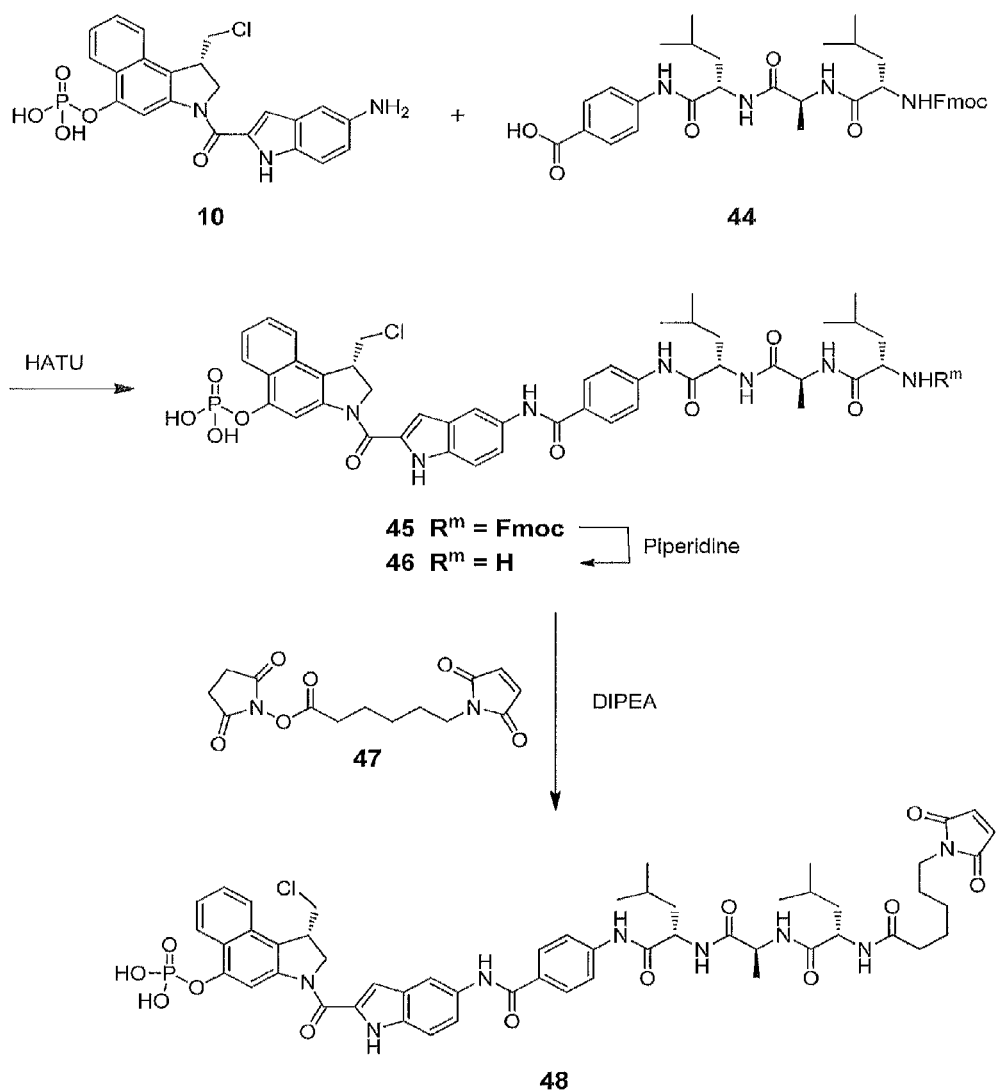

This example and FIGS. 9A-9B in combination describe the synthesis of compound 48, also referred to herein as compound (IIe).

Compound 37. Copper(II) chloride (Aldrich, 1.252 g, 9.31 mmol) was added to a solution of tert-butyl 4-aminobenzoate 36 (Fluka, 1.5 g, 7.76 mmol), Fmoc-protected leucine 35 (BaChem, 2 g, 5.66 mmol), EDC (Fluka, 1.786 g, 9.31 mmol) and t-butanol (Chem-impex, 1.426 g, 9.31 mmol) in DMF (Aldrich, anhydrous, 15 mL). The reaction mixture was stirred at RT overnight. The reaction mixture was worked up with EtOAc (30 mL), water (30 mL) and brine (30 mL). The organic phases were concentrated and dried under high vacuum to yield compound 37 (3.7 g). MS: [M+H] 529.

Compound 38. Piperidine (Aldrich, 3 mL) was added to a solution of crude compound 37 (3.7 g) in DMF (Aldrich, anhydrous, 15 mL). The reaction mixture was kept at RT for 1 h and then purified by preparative HPLC, eluting with 10-65% acetonitrile gradient in water (with 0.1% TFA). The product-containing fractions were combined and freeze-dried to yield compound 38 (1.7 g, 70.8% over two steps). MS: [M+H] 307.

Compound 41. DIPEA (Aldrich, 0.97 mL, 5.5 mmol) was added to a solution of alanine t-butyl ester hydrochloride 39 (BaChem, 0.4 g, 2.22 mmol) and compound 40 (Bachem, 1 g, 2.22 mmol) in DMF (Aldrich, anhydrous, 20 mL). The reaction mixture was stirred at RT for 1 h and was worked up with EtOAc (100 mL), water (50 mL) and brine (50 mL). The organic phases were concentrated and dried under high vacuum to yield compound 41 (1.3 g). MS: [M+H] 481.

Compound 42. TFA (Acros, 10 mL) was added to a solution of crude compound 41 (1.3 g) in DCM (Acros, anhydrous, 10 mL). The reaction mixture was kept at RT for 1 h, concentrated and purified by preparative HPLC, eluting with 10-100% acetonitrile gradient in water (with 0.1% TFA). The product-containing fractions were combined and freeze-dried to yield compound 42 (0.68 g, 72.2% over two steps). MS: [M+H] 425.

Compound 43. DIPEA (Aldrich, 0.246 mL, 1.413 mmol) was added to a solution of compound 38 (289 mg, 0.842 mmol), compound 42 (200 mg, 0.471 mmol) and BOP (Bachem, 313 mg, 0.707 mmol) in DMF (Aldrich, anhydrous, 3 mL). The reaction mixture was stirred at RT for 2 h and worked up with EtOAc (30 mL), water (20 mL) and brine (20 mL). The organic phases were concentrated and purified on a 4 g COMBIFLASH™ column, eluting with 0-60% EtOAc gradient in hexane. The organic phases were combined, concentrated, and dried under high vacuum to yield compound 43 (126 mg, 37.5%). MS: [M+H] 713.

Compound 44. TFA (Acros, 3 mL) was added to a solution of compound 43 (126 mg) in DCM (Acros, anhydrous, 3 mL). The reaction mixture was kept at RT for 0.5 h, concentrated, and purified by preparative HPLC, eluting with 10-100% acetonitrile gradient in water (with 0.1% TFA). The product-containing fractions were combined and freeze-dried to yield compound 44 (84 mg, 72%). MS: [M+H] 657.

Compound 45. DIPEA (Aldrich, 21 µL, 0.122 mmol) was added to a solution of compound 44 (40 mg, 0.061 mmol), HATU (Oakwood, 18.53 mg, 0.049 mmol) in DMF (Aldrich, anhydrous, 1 mL) The pH of the reaction mixture was above 8. The reaction mixture was stirred at RT for 15 min. To this reaction mixture was added compound 10 (34.5 mg, 0.073 mmol), followed by additional DIPEA (Aldrich, 21 µL, 0.122 mmol). The reaction mixture was stirred at RT for 30 min and purified by preparative HPLC, eluting with 10-100% acetonitrile gradient in water (with 0.1% TFA). The product-containing fractions were combined and freeze-dried to yield compound 45 (20 mg, 30%). MS: [M+H] 1110.

Compound 46. Piperidine (Aldrich, 0.2 mL, 2.02 mmol) was added to a solution of compound 45 (20 mg) in DMF (Acros, anhydrous, 0.5 mL). The reaction mixture was kept at RT for 1 h. The reaction mixture was purified by preparative HPLC, eluting with 10-65% acetonitrile gradient in water (with 0.1% TFA). The product-containing fractions were combined and freeze-dried to yield compound 46 (8 mg, 50%). MS: [M+H] 888.

Compound 48. DIPEA (Aldrich, 10 µL, 0.006 mmol) was added to a solution of compound 46 (8 mg, 0.009 mmol) and N-succinimidyl 6-maleimidohexanote 47 (TCI, 5.55 mg, 0.018 mmol) in DMF (Acros, anhydrous, 1 mL). The reaction mixture was kept at RT for 1 h. The reaction mixture was purified by preparative HPLC, eluting with 10-100% acetonitrile gradient in water (with 0.1% TFA). The product-containing fractions were combined and freeze-dried to yield compound 48 (2 mg, 20%). MS: [M+H] 1081.

The Leu-Ala-Leu tripeptide of compound 48 (IIe) is a substrate motif for the enzyme CD10, so that conjugates made with this compound should be susceptible to cleavage by CD10.

Example 11

Compound (IIf)

Figure 10A:
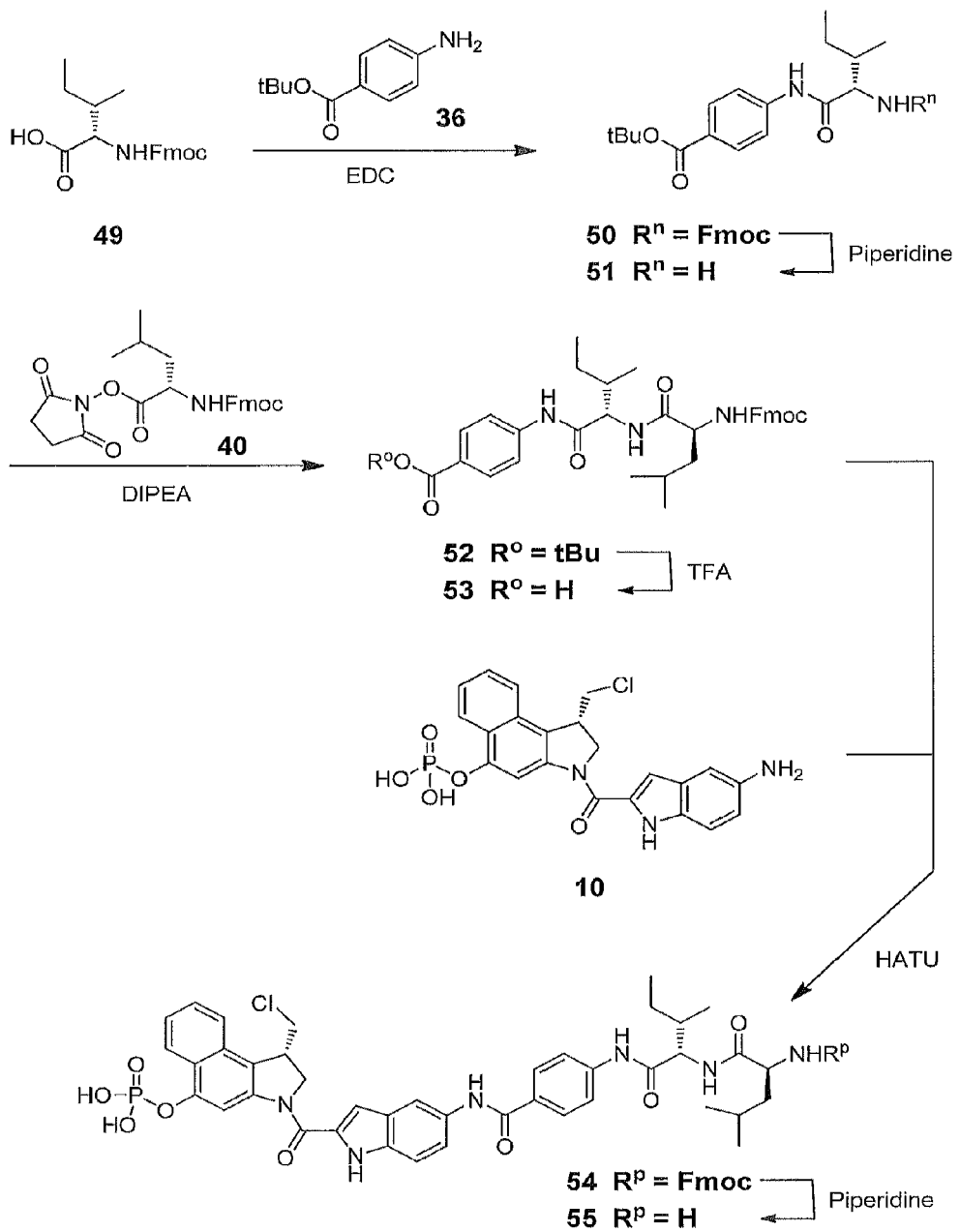
FIGS. 10A and 10B show in combination the synthesis of a compound of this invention, having a Leu-Ile dipeptide.
Figure 10B:
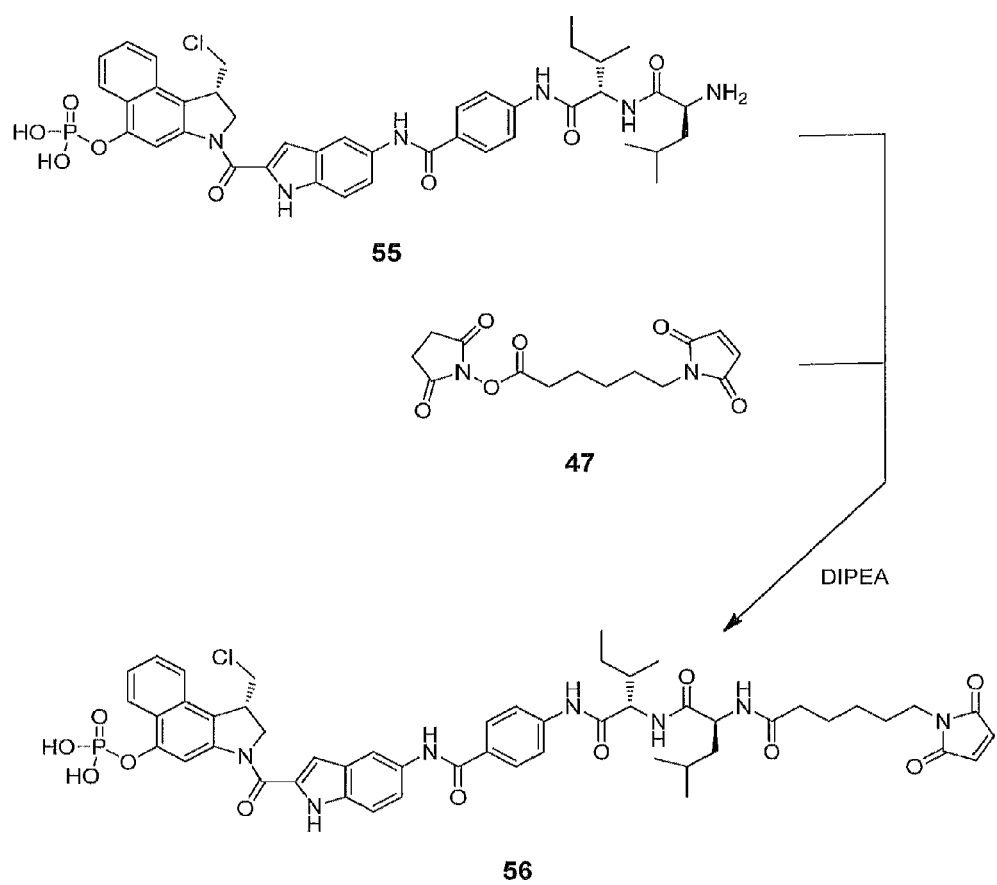

This example and FIGS. 10A-10B in combination describe the synthesis of compound 56, also referred to herein as compound (IIf).

Compound 50. Copper(II) chloride (Aldrich, 0.913 g, 6.79 mmol) was added to a solution of tert-butyl 4-aminobenzoate 36 (Fluka, 1.312 g, 6.79 mmol), Fmoc-protected isoleucine 49 (BaChem, 2 g, 5.66 mmol), EDC (Fluka, 1.302 g, 6.79 mmol) and t-butanol (Chem-impex, 1.040 g, 6.79 mmol) in DMF (Aldrich, anhydrous, 20 mL). The reaction mixture was stirred at RT overnight. The reaction mixture was worked up with EtOAc (30 mL), water (30 mL) and brine (30 mL). The combined organic phases were concentrated and purified on a 40 g COMBIFLASH™ column, eluting with 0-20% EtOAc gradient in hexane. The product-containing fractions were combined, concentrated, and dried under high vacuum to yield compound 50 (0.85 g, 28.4%). MS: [M+H] 529.

Compound 51. Piperidine (Aldrich, 0.5 mL) was added to a solution of crude compound 50 (3.7 g) in DMF (Aldrich, anhydrous, 5 mL). The reaction mixture was kept at RT for 1 h. The reaction mixture was worked up with EtOAc (20 mL), water (15 mL) and brine (15 mL). The organic phases were combined, concentrated, and purified on a 12 g COMBI-FLASH™ column, eluting with 0-75% EtOAc gradient in hexane. The product-containing fractions were combined, concentrated, and dried under high vacuum to yield compound 51 (0.38 g, 76.9%). MS: [M+H] 307.

Compound 52. DIPEA (Aldrich, 0.228 mL, 1.305 mmol) was added to a solution of compound 51 (0.2 g, 0.653 mmol) and compound 40 (Bachem, 294 mg, 0.653 mmol) in DMF (Aldrich, anhydrous, 3 mL). The reaction mixture was stirred at RT for 2 h. The reaction mixture was worked up with EtOAc (50 mL), water (20 mL) and brine (20 mL). The combined organic phases were concentrated and purified on a 4 g COMBIFLASH™ column, eluting with 0-40% EtOAc gradient in hexane. The product-containing fractions were concentrated to a residue, which was dried under high vacuum to yield compound 52 (178 mg, 42.5%). MS: [M+H] 642.

Compound 53. TFA (Acros, 3 mL) was added to a solution of compound 52 (178 mg, 0.277 mmol) in DCM (Acros, anhydrous, 3 mL). The reaction mixture was kept at RT for 0.5 h. The reaction mixture was concentrated and freeze-dried to yield compound 53 (145 mg, 89.5%). MS: [M+H] 586.

The Leu-Ile dipeptide of compound 56 (IIf) is a substrate motif for the enzyme cathepsin E, so that immunoconjugates made with this compound should be susceptible to cleavage by cathepsin E.

Example 12

Compound (IIg)

Figure 11A:
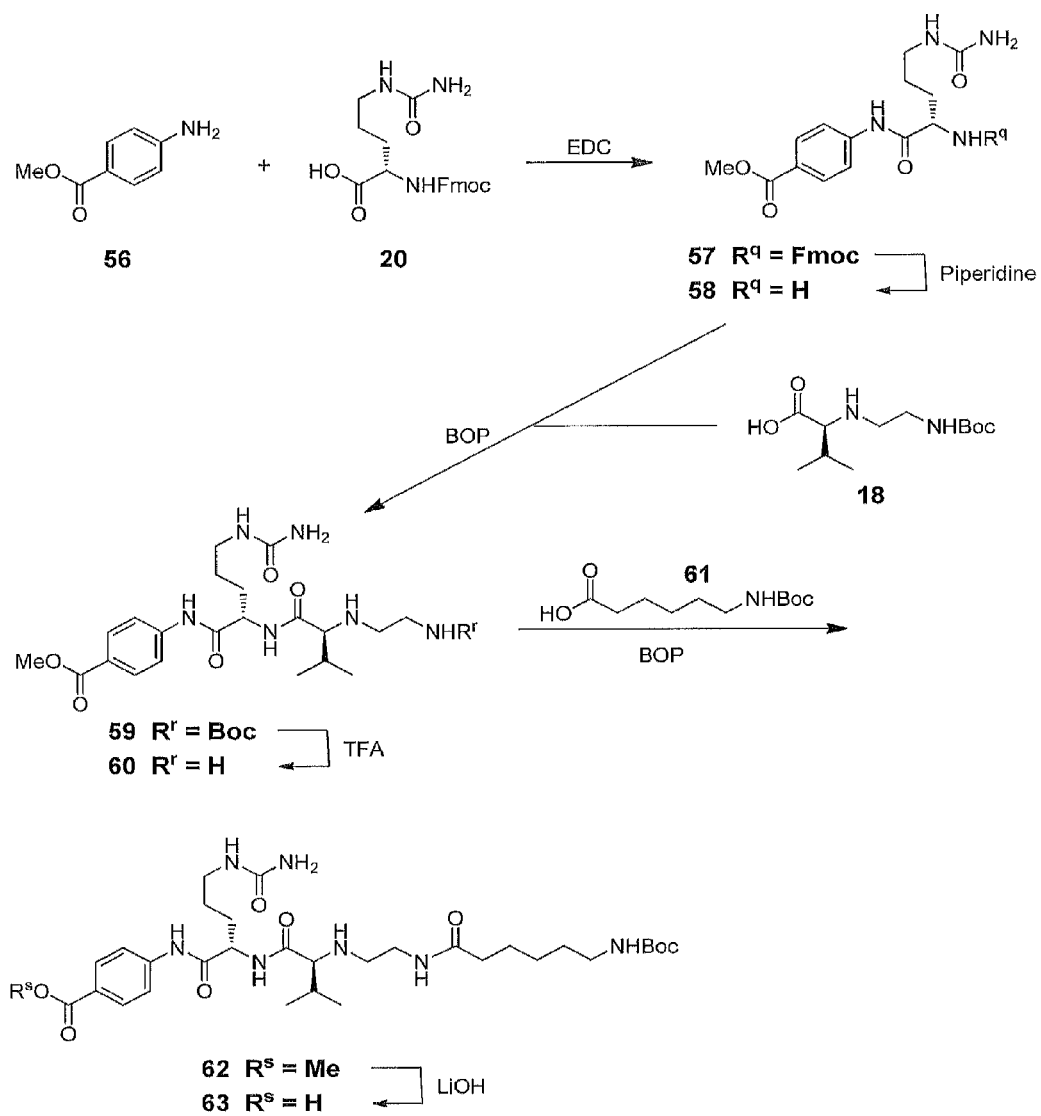
FIGS. 11A and 11B show in combination the synthesis of another compound of this invention.
Figure 11B:
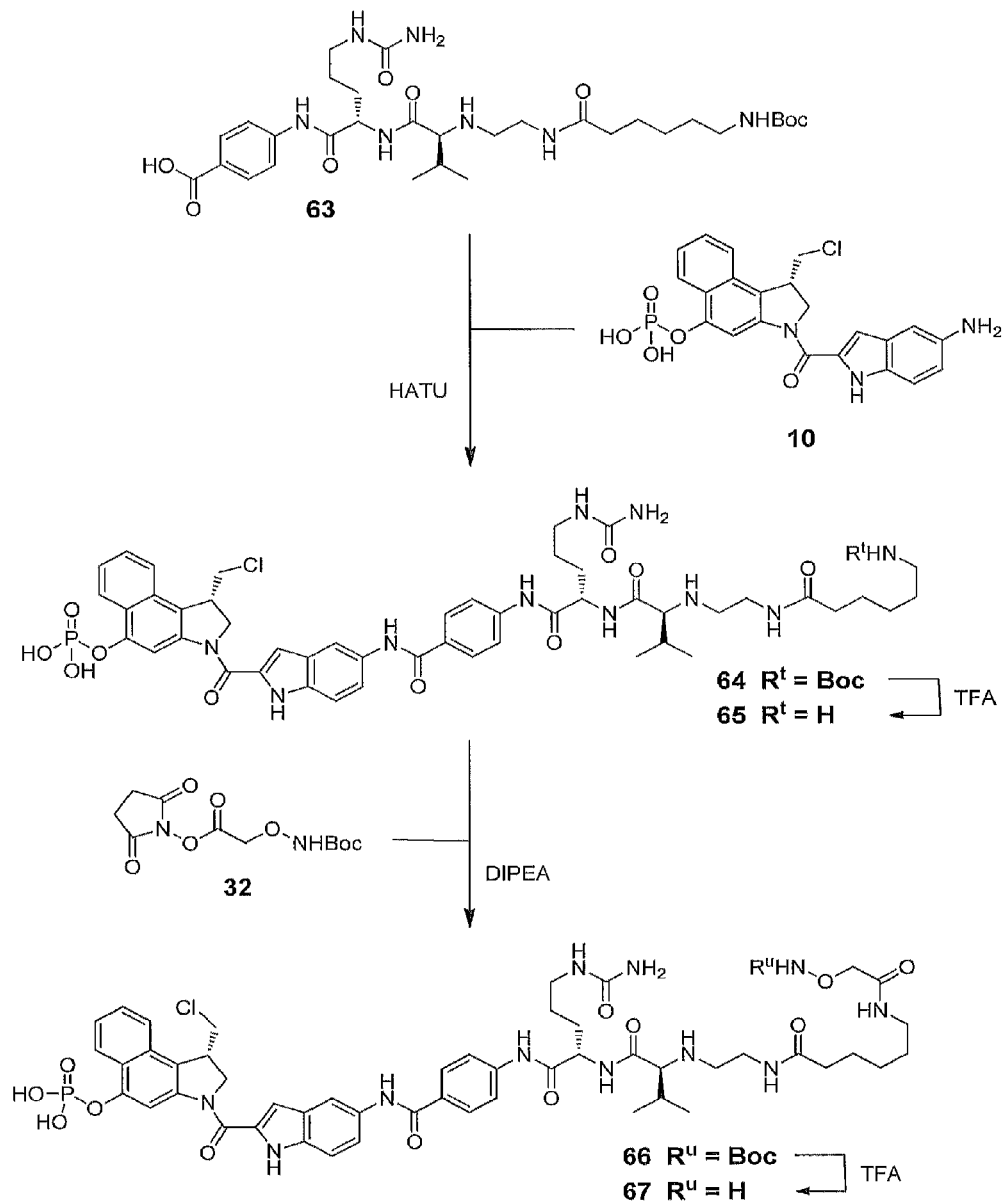

This example and FIGS. 11A-11B in combination describe the synthesis of compound 67, also referred to herein as compound (IIg).

Compound 57. Copper(II) chloride (Aldrich, 0.913 g, 6.79 mmol) was added to a solution of methyl 4-aminobenzoate 56 (Aldrich, 0.913 g, 6.05 mmol), Fmoc-protected citrulline 20 (BaChem, 2 g, 5.04 mmol), EDC (Fluka, 1.160 g, 6.05 mmol) and t-butanol (Chem-impex, 0.926 g, 6.05 mmol) in DMF (Aldrich, anhydrous, 20 mL). The reaction mixture was stirred at RT overnight. The reaction mixture was worked up with EtOAc (100 mL), water (30 mL), and brine (30 mL). The organic phases were concentrated and purified on a 40 g COMBIFLASH™ column, eluting with 0-20% methanol gradient in DCM. The product-containing fractions were combined, concentrated, and dried under high vacuum to yield compound 57 (1.825 g, 68.2%). MS: [M+H] 531.

Compound 58. Piperidine (Aldrich, 0.2 mL) was added to a solution of compound 57 (1.25 g, 3.437 mmol) in DMF (Aldrich, anhydrous, 3 mL). The reaction mixture was stirred at RT for 1 h. The reaction mixture was worked up with EtOAc (40 mL), water (15 mL), and brine (15 mL). The organic phases were combined, concentrated, and purified on a 12 g COMBIFLASH™ column, eluting with 0-30% methanol gradient in DCM. The product-containing fractions were combined, concentrated, and dried under high vacuum to yield compound 58 (0.778 g, 73.1%). MS: [M+H] 309.

Compound 59. DIPEA (Aldrich, 1.0 mL, 5.71 mmol) was added to a solution of compound 58 (778 mg, 2.52 mmol), compound 18 (655 mg, 2.52 mmol) and BOP (Bachem, 1.12 g, 2.52 mmol) in DMF (Aldrich, anhydrous, 10 mL). The reaction mixture was stirred at RT for 2 h. The reaction mixture was worked up with EtOAc (50 mL), water (20 mL), and brine (20 mL). The combined organic phases were concentrated and purified on a 40 g COMBIFLASH™ column, eluting with 0-15% methanol gradient in DCM. The organic phases were combined, concentrated, and dried under high vacuum to yield compound 59 (1.06 g, 76%). MS: [M+H] 551.

Compound 60. TFA (Acros, 5 mL) was added to a solution of compound 59 (1.06 g, 1.92 mmol) in DCM (Acros, anhydrous, 5 mL). The reaction mixture was stirred at RT for 0.5 h. The reaction mixture was concentrated and freeze-dried to yield compound 60 as its TFA salt (1.09 g). MS: [M+H] 451.

Compound 62. DIPEA (Aldrich, 1.02 mL, 5.838 mmol) was added to a solution of compound 60 (500 mg, 1.109 mmol), 6-((tert-butoxycarbonyl)amino)hexanoic acid 61 (Fluka, 450 mg, 1.946 mmol) and BOP (Bachem, 0.720 g, 1.629 mmol) in DMF (Aldrich, anhydrous, 10 mL). The reaction mixture was stirred at RT for 1 h. The reaction mixture was worked up with EtOAc (60 mL), water (30 mL), and brine (30 mL). The combined organic phases were concentrated and purified on a 12 g COMBIFLASH™ column, eluting with 0-20% methanol gradient in DCM. The organic phases were combined, concentrated, and dried under high vacuum to yield compound 62 (427 mg, 58%). MS: [M+H] 664.

Compound 63. LiOH solution (Aldrich, 150 mg in 10 mL water) was added to a solution of compound 62 (0.427 g, 0.643 mmol) in acetone (Baker, 10 mL). The reaction mixture was stirred at RT for 3 h and neutralized with acetic acid (Fisher, glacial, 0.3 mL). The reaction mixture was purified by preparative HPLC, eluting with 10-65% acetonitrile gradient in water (with 0.1% TFA). The product-containing fractions were combined and freeze-dried to yield compound 63 (325 mg, 77.8%). MS: [M+H] 650.

Compound 64. DIPEA (Aldrich, 27 µL, 0.153 mmol) was added to a solution of compound 63 (59.5 mg, 0.092 mmol), HATU (Oakwood, 23.21 mg, 0.061 mmol) in DMF (Aldrich, anhydrous, 1 mL). The reaction mixture was stirred at RT for 30 min. To this was added compound 10 (36 mg, 0.076 mmol), followed by additional DIPEA (Aldrich, 27 µL, 0.153 mmol). The reaction mixture was stirred at RT for 1 h and purified by preparative HPLC, eluting with 10-65% acetonitrile gradient in water (with 0.1% TFA). The product-containing fractions were combined and freeze-dried to yield compound 64 (38 mg, 55.7%). MS: [M+H] 1103.

Compound 65. TFA (Acros, 1 mL) was added to a solution of compound 64 (38 mg, 0.034 mmol) in DCM (Acros, anhydrous, 1 mL). The reaction mixture was stirred at RT for 0.5 h. The reaction mixture was concentrated and freeze-dried to yield compound 65 as its TFA salt (43 mg). MS: [M+H] 1003.

Compound 66. DIPEA (Aldrich, 29 µL, 0.159 mmol) was added to a solution of compound 32 (15.4 mg, 0.053 mmol) and compound 65 (43 mg, 0.043 mmol) in DMF (Aldrich, anhydrous, 1 mL). The reaction mixture was stirred at RT for 1 h. The reaction mixture was purified by preparative HPLC, eluting with 10-65% acetonitrile gradient in water (with 0.1% TFA). The product-containing fractions were combined and freeze-dried to yield compound 66 (22 mg, 43.5%). MS: [M+H] 1176.

Compound 67. A solution of compound 66 (22 mg, 0.019 mmol) in 4N HCl 1,4-dioxane solution (Aldrich, 10 mL) was stirred at RT for 1 h. The reaction mixture was concentrated and purified by preparative HPLC, eluting with 10-65% acetonitrile gradient in water (with 0.1% TFA). The product-containing fractions were combined and freeze-dried to yield compound 67 (12 mg, 58.7%). MS: [M+H] 1076.

Example 13

In Vivo Studies

FIGS. 12A-12I demonstrate the in vivo efficacy of immunoconjugates of this invention in xenograft studies with mice, against a variety of cancer types.

Figure 12A:
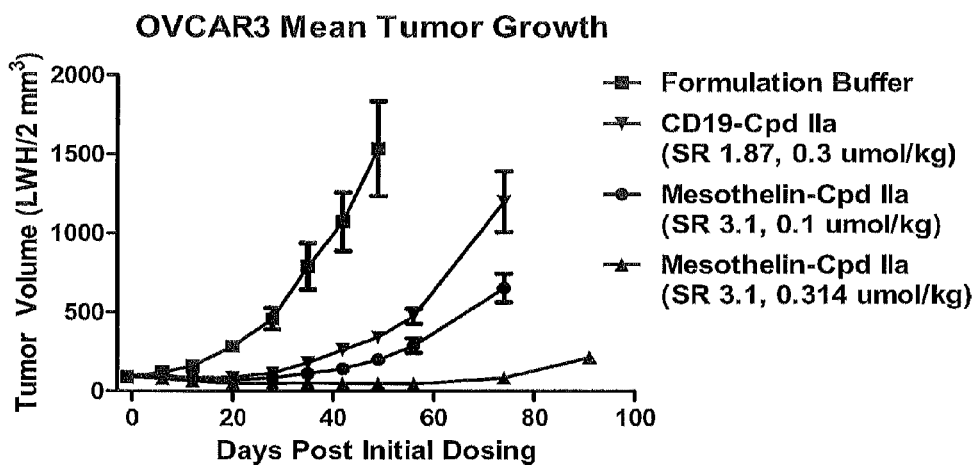
FIGS. 12A-12I show the results of various xenograft studies.

OVCAR3 cell study. Five million OVCAR3 ovarian cancer cells, resuspended in 0.1 mL phosphate buffered saline ("PBS") plus 0.1 mL matrigel, were implanted subcutaneously at the flank region of SCID mice. Tumor measurements started 23 days later, and mice were randomized into groups of 6 mice each with average tumor sizes of 90 mm$^3$ estimated by LWH/2 of tumors. At 24 days post tumor implantation, mice were dosed intraperitoneally singly with testing compounds. FIG. 12A shows that, against OVCAR3 cells, immunoconjugates of anti-mesothelin antibody 6A4 with compound (IIa) suppressed tumor growth, especially at the higher dosage of 0.314 mol/kg of cytotoxin. Comparative data for the corresponding immunoconjugate of the anti-CD19 antibody 21D4 is also presented, as an isotype control.

Figure 12B:
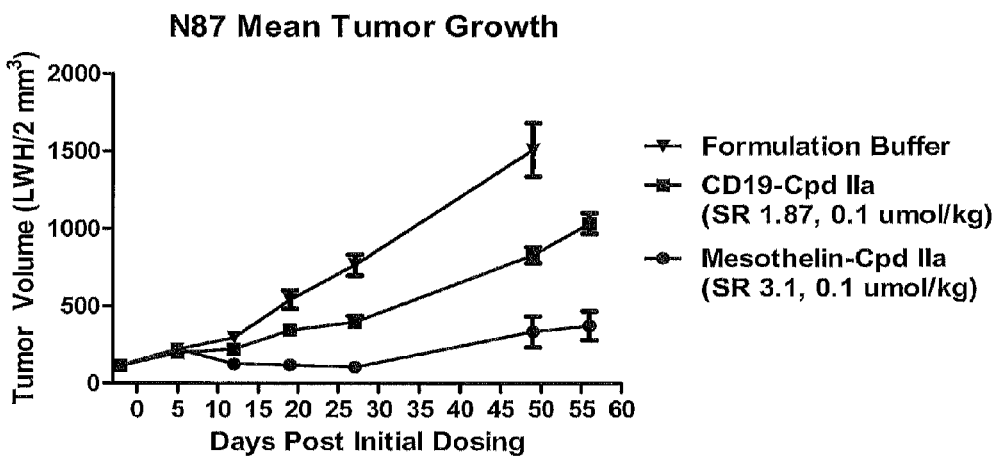

N87 cell study. Two and a half million N87 gastric tumor cells, resuspended in 0.1 mL PBS plus 0.1 mL matrigel, were implanted subcutaneously at the flank region of SCID mice. Tumor measurements started 12 days later, and mice were randomized into groups of 7 mice each with average tumor sizes of 110 mm$^3$ estimated by LWH/2 of tumors. At 14 days post tumor implantation, mice were dosed intraperitoneally singly with testing compounds. FIG. 12B shows that, against N87 cells, an immunoconjugate of anti-mesothelin antibody 6A4 with compound (IIa) strongly inhibits tumor growth. Comparative data for formulation buffer alone or an immunoconjugate of anti-CD19 antibody 21D4 and compound (IIa) are presented, the latter as an isotype control.

Figure 12C:
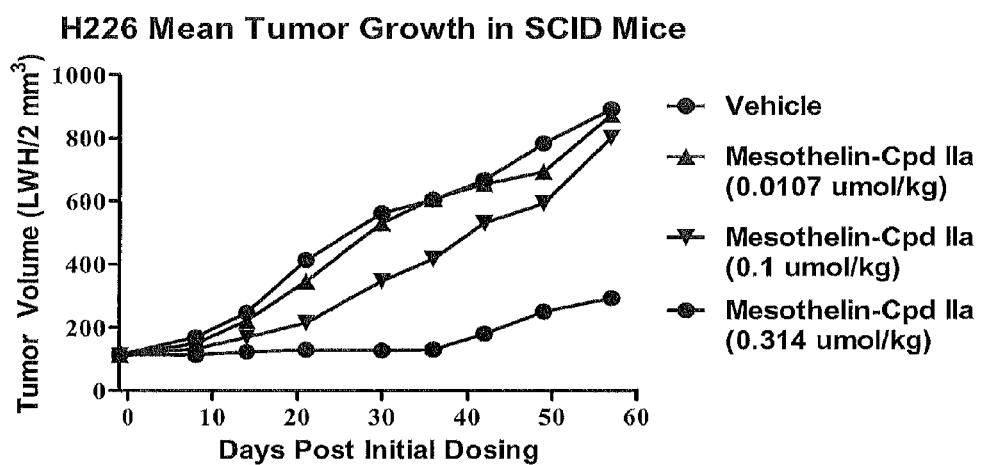

H226 cell study. Five million H226 mesothelioma cells, resuspended in 0.1 mL PBS plus 0.1 mL matrigel, were implanted subcutaneously at the flank region of SCID mice. Tumor measurements started 14 days later, and mice were randomized into groups of 9 mice each with average tumor sizes of 110 mm$^3$ estimated by LWH/2 of tumors. At 15 days post tumor implantation, mice were dosed intraperitoneally singly with testing compounds. FIG. 12C shows the dose-dependent effect of an immunoconjugate of anti-mesothelin antibody 6A4 and compound (IIa) on tumor growth. The SR was 3.6 in each instance.

Figure 12D:
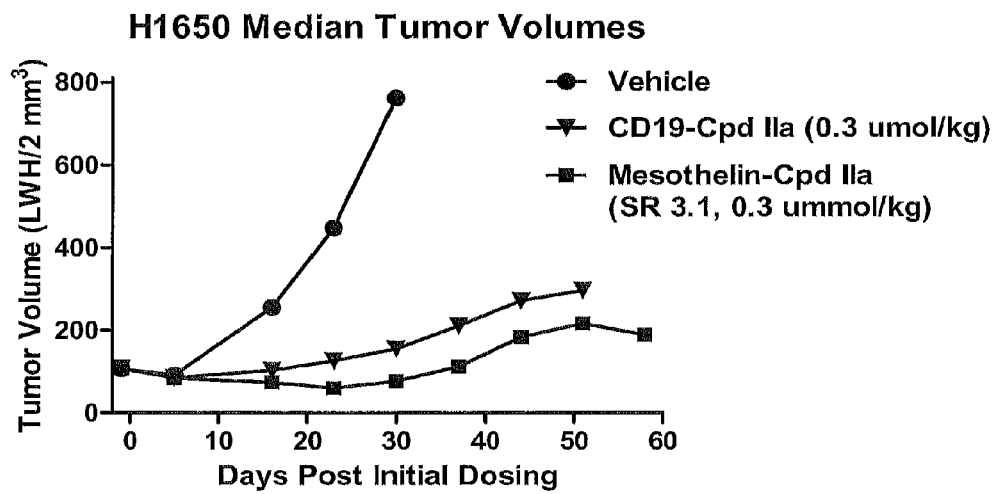

H1650 cell study. Two and a half million H1650 lung tumor (adenocarcinoma) cells, resuspended in 0.1 mL PBS plus 0.1 mL matrigel, were implanted subcutaneously at the flank region of SCID mice. Tumor measurements started 7 days later, and mice were randomized into groups of 6 mice each with average tumor sizes of 110 mm$^3$ estimated by LWH/2 of tumors. At 9, 14 and 21 days post tumor implantation, mice were dosed intraperitoneally repeatedly with testing compounds. FIG. 12D shows the tumor inhibition by an immunoconjugate of anti-mesothelin antibody 6A4 and compound (IIa). Comparative data for a vehicle control and an immunoconjugate of anti-CD19 antibody 21D4 and compound (IIa) are presented, the latter as an isotype control.

Figure 12E:
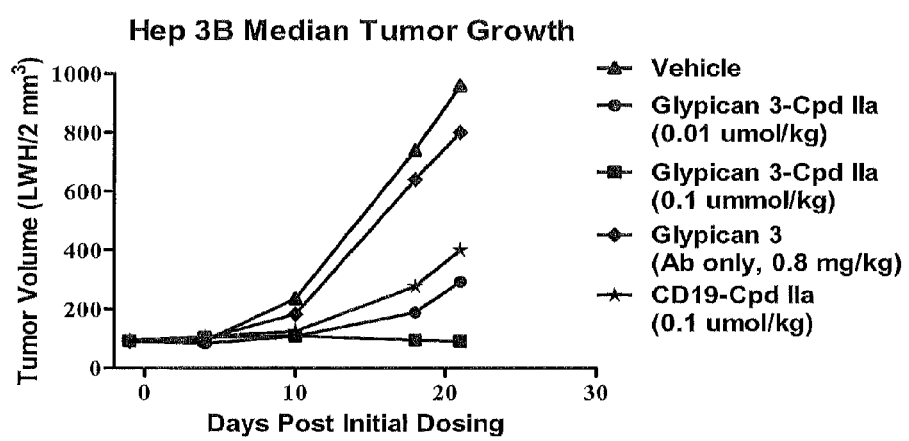
Figure 12F:
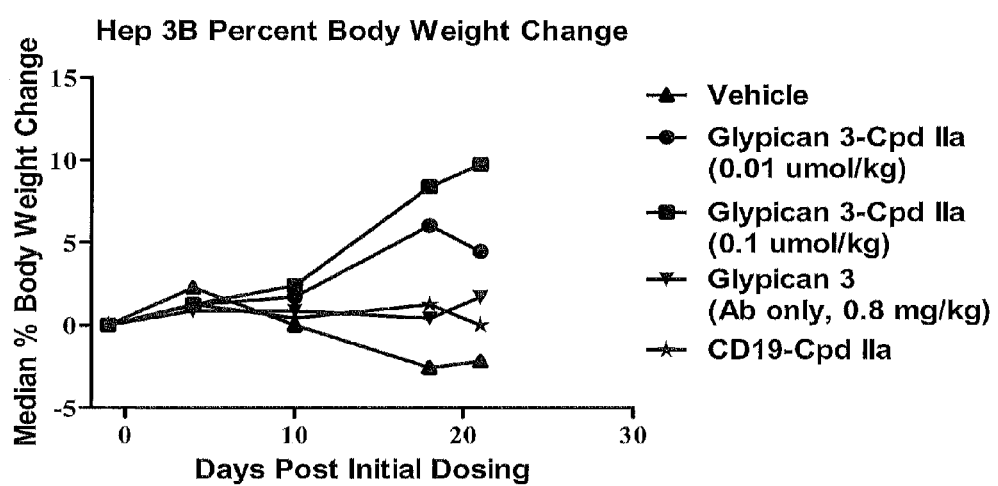

Hep 3B cell study. Four million Hep 3B liver tumor cells, resuspended in 0.1 mL PBS plus 0.1 mL matrigel, were implanted subcutaneously at the flank region of SCID mice. Tumor measurements started 10 days later, and mice were randomized into groups of 7 mice each with average tumor sizes of 90 mm$^3$ estimated by LWH/2 of tumors. At 11 days post tumor implantation, mice were dosed intraperitoneally singly with testing compounds. FIG. 12E shows the dose-dependent tumor growth inhibitory effect of an immunoconjugate of anti-glypican 3 antibody 4A6 and compound (IIa). The strongest effect was seen with a dose of 0.1 µmol/kg. Comparative data for vehicle alone, antibody 4A6 alone, or an immunoconjugate of anti-CD19 antibody 21D4 and compound (IIa) are also shown, the latter as an isotype control. FIG. 12F is a graph from the same study, but demonstrating the ability of the antibody 4A6-compound (IIa) immunoconjugate to alleviate tumor-associated cachexia. Data for the anti-CD19-compound (IIa) immunoconjugate is also presented showing that the anti-CD19 conjugate, while it reduces tumor growth (per FIG. 12E), it does not alleviate cachexia (per FIG. 12F).

Figure 12G:
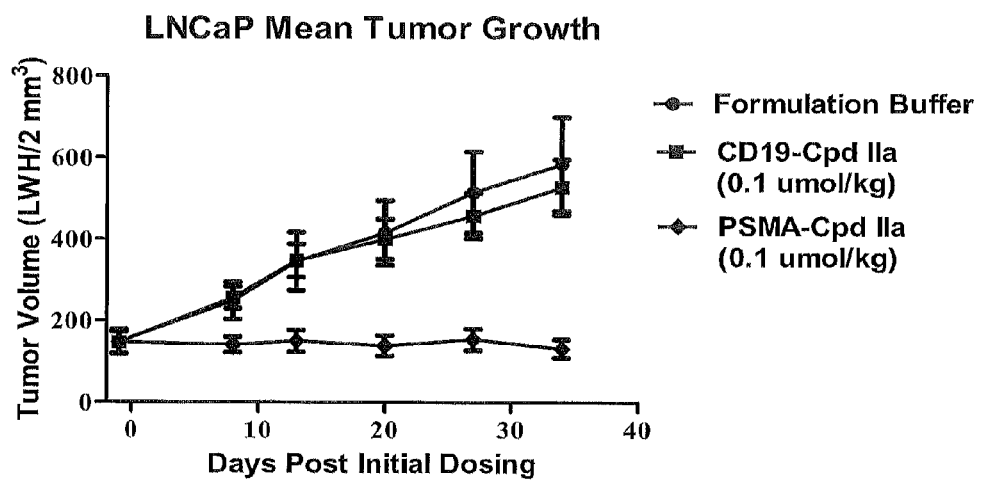
Figure 12H:
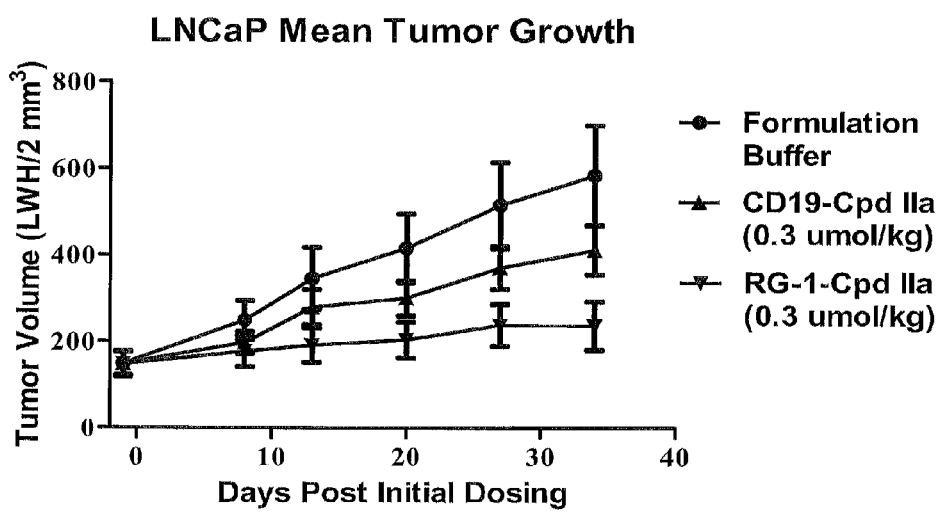

LNCaP cell study. Two and a half million LNCaP prostate tumor cells, resuspended in 0.1 mL PBS plus 0.1 mL matrigel, were implanted subcutaneously at the flank region of SCID mice. Tumor measurements started 30 days later, and mice were randomized into groups of 7 mice each with average tumor sizes of 150 mm$^3$ estimated by LWH/2 of tumors. At 31 days post tumor implantation, mice were dosed intraperitoneally singly with testing compounds. FIG. 12G shows the tumor growth inhibition by an immunoconjugate of anti-PSMA antibody 2A10 and compound (IIa), compared to formulation buffer and an immunoconjugate of anti-CD19 antibody 21D4 and compound (IIa) as isotype control. In each instance the cytotoxin concentration was 0.1 μmol/kg. FIG. 12H shows another set of results from the same study, with an immunoconjugate of anti-RG-1 antibody 19G9 and compound (IIa), with an isotype control of an anti-CD19 immunoconjugate.

Figure 12I:
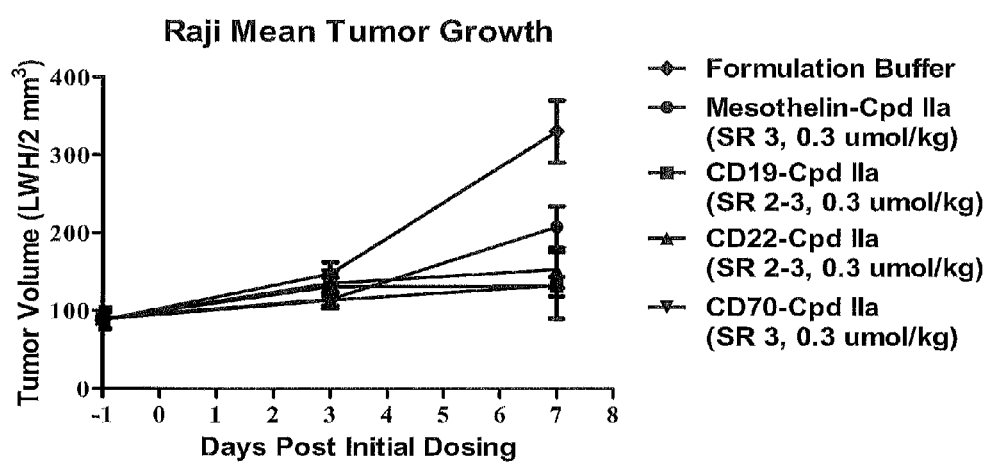

Raji cell study. Ten million Raji human Burkitt's lymphoma cells, resuspended in 0.1 mL PBS plus 0.1 mL matrigel, were implanted subcutaneously at the flank region of SCID mice. Tumor measurements started 6 days later, and mice were randomized into groups of 8 mice each with average tumor sizes of 90 mm$^3$ estimated by LWH/2 of tumors. At 7 days post tumor implantation, mice were dosed intraperitoneally singly with testing compounds. FIG. 12I shows the tumor growth inhibitory effect by immunoconjugates of anti-mesothelin antibody 6A4, anti-CD19 antibody 21D4, anti-CD22 antibody 12C5, and anti-CD70 antibody 1F4, each with compound (IIa). (The full sequence information for antibody 1F4 is disclosed in Coccia et al. 2010, the disclosure of which is incorporated herein by reference. The $V_H$ CDR1, CDR2, and CDR3 and $V_K$ CDR1, CDR2, and CDR3 sequences for antibody 1F4 are given in SEQ ID NO:55, SEQ ID NO:56, SEQ ID NO:57, SEQ ID NO:58, SEQ ID NO:59, and SEQ ID NO:60, respectively.)

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

References

Full citations for the following references cited in abbreviated fashion by first author (or inventor) and date earlier in this specification are provided below. Each of these references is incorporated herein by reference for all purposes.

Aristoff et al., WO 91/16324 (1991).
Best, *Biochemistry* 2009, 48, 6571-6584.
Boger et al., *Synthesis* 1999, 1505-1509.
Boyd et al., US 2008/0279868 A1 (2008).
Boyd et al., U.S. Pat. No. 7,691,962 B2 (2010).
Cacciari et al., *Expert Opinion Therapeutic Patents* 2000, 10(12), 1853-1871.
Cardarelli et al., U.S. Pat. No. 7,875,278 B2 (2011).
Chen et al., U.S. Pat. No. 7,517,903 B2 (2009).
Chen et al., US 2010/0113476 A1 (2010).
Coccia et al., US 2010/0150950 A1 (2010).
Dubowchik et al., *Bioconjugate Chem.* 2002, 13, 855-869.
Gangwar et al., US 2008/0293800 A1 (2008).
Glazier, WO 03/000201 A2 (2003).
Huang et al., US 2009/0297438 A1 (2009).
King et al., US 2010/0104509 A1 (2010) [2010a].
King et al., US 2010/0143368 A1 (2010) [2010b].
King et al., US 2011/0020329 A1 (2011).
Kobayashi et al., *Cancer Res.* 1994, 54, 2404-2410.
Korman et al., US 2009/0074660 A1 (2009).
Kutyavin et al., U.S. Pat. No. 5,659,022 (1997).
Ng et al., WO 02/096910 A1 (2002).
Ng et al., U.S. Pat. No. 6,989,452 B2 (2006) [2006a].
Ng et al., U.S. Pat. No. 7,129,261 B2 (2006) [2006b].
Ng et al., U.S. Pat. No. 7,498,302 B2 (2009) [2009a].
Ng et al., U.S. Pat. No. 7,507,420 B2 (2009) [2009b].
Ng et al., US RE41,252 E (2010).
Rao-Naik et al., U.S. Pat. No. 8,097,703 B2 (2012).
Suckling, *Expert Opinion Therapeutic Patents* 2004, 14(12), 1693-1724.
Sufi et al., US 2010/0145036 A1 (2010).
Terrett et al., US 2010/0034826 A1 (2010) [2010a].
Terrett et al., US 2010/0209432 A1 (2010) [2010b].
Terrett et al., Us 2011/0085970 A1 (2011) [2011a].
Terrett et al., US 2011/0262448 A1 (2011) [2011b].
Terrett et al., US 2012/0027782 A1 (2012) [2012a].
Terrett et al., U.S. Pat. No. 8,124,738 B2 (2012) [2012b].
Zhao et al., Poster 45, 28th National Medicinal Chemistry Symposium (San Diego, Calif., 8-12 Jun. 2002), "An improved synthesis of CC-1065 analogs and development of prodrugs" (abstract). [2002a].
Zhao et al., Poster MEDI 147, 224th National Meeting of the American Chemical Society (Boston, Mass., 18-22 Aug. 2002), "New water-soluble CC-1065 analog prodrugs: Design, synthesis and evalution" (abstract) [2002b].
Zhao et al., U.S. Pat. No. 7,655,660 B2 (2010).

Table of Sequences

The following table summarizes the descriptions of the sequences disclosed in this application.

| SEQ ID NO: | SEQUENCE DESCRIPTION |
|---|---|
| 1 | 2H5 $V_H$ CDR1 amino acid |
| 2 | 2H5 $V_H$ CDR2 amino acid |
| 3 | 2H5 $V_H$ CDR3 amino acid |
| 4 | 2H5 $V_K$ CDR1 amino acid |
| 5 | 2H5 $V_K$ CDR2 amino acid |
| 6 | 2H5 $V_K$ CDR3 amino acid |
| 7 | 6A4 $V_H$ CDR1 amino acid |
| 8 | 6A4 $V_H$ CDR2 amino acid |
| 9 | 6A4 $V_H$ CDR3 amino acid |
| 10 | 6A4 $V_K$ CDR1 amino acid |
| 11 | 6A4 $V_K$ CDR2 amino acid |
| 12 | 6A4 $V_K$ CDR3 amino acid |
| 13 | 21D4 $V_H$ CDR1 amino acid |
| 14 | 21D4 $V_H$ CDR2 amino acid |
| 15 | 21D4 $V_H$ CDR3 amino acid |
| 16 | 21D4 $V_K$ CDR1 amino acid |
| 17 | 21D4 $V_K$ CDR2 amino acid |
| 18 | 21D4 $V_K$ CDR3 amino acid |
| 19 | 2A10 $V_H$ CDR1 amino acid |

| SEQ ID NO: | SEQUENCE DESCRIPTION |
|---|---|
| 20 | 2A10 $V_H$ CDR2 amino acid |
| 21 | 2A10 $V_H$ CDR3 amino acid |
| 22 | 2A10 $V_K$ CDR1 amino acid |
| 23 | 2A10 $V_K$ CDR2 amino acid |
| 24 | 2A10 $V_K$ CDR3 amino acid |
| 25 | 4A6 $V_H$ CDR1 amino acid |
| 26 | 4A6 $V_H$ CDR2 amino acid |
| 27 | 4A6 $V_H$ CDR3 amino acid |
| 28 | 4A6 $V_K$ CDR1 amino acid |
| 29 | 4A6 $V_K$ CDR2 amino acid |
| 30 | 4A6 $V_K$ CDR3 amino acid |
| 31 | 2A7 $V_H$ CDR1 amino acid |
| 32 | 2A7 $V_H$ CDR2 amino acid |
| 33 | 2A7 $V_H$ CDR3 amino acid |
| 34 | 2A7 $V_L$ CDR1 amino acid |
| 35 | 2A7 $V_L$ CDR2 amino acid |
| 36 | 2A7 $V_L$ CDR3 amino acid |
| 37 | 19G9 $V_H$ CDR1 amino acid |
| 38 | 19G9 $V_H$ CDR2 amino acid |
| 39 | 19G9 $V_H$ CDR3 amino acid |
| 40 | 19G9 $V_L$ CDR1 amino acid |
| 41 | 19G9 $V_L$ CDR2 amino acid |
| 42 | 19G9 $V_L$ CDR3 amino acid |
| 43 | 12C5 $V_H$ CDR1 amino acid |
| 44 | 12C5 $V_H$ CDR2 amino acid |
| 45 | 12C5 $V_H$ CDR3 amino acid |
| 46 | 12C5 $V_K$ CDR1 amino acid |
| 47 | 12C5 $V_K$ CDR2 amino acid |
| 48 | 12C5 $V_K$ CDR3 amino acid |
| 49 | 4D5 $V_H$ CDR1 amino acid |
| 50 | 4D5 $V_H$ CDR2 amino acid |
| 51 | 4D5 $V_H$ CDR3 amino acid |
| 52 | 4D5 $V_K$ CDR1 amino acid |
| 53 | 4D5 $V_K$ CDR2 amino acid |
| 54 | 4D5 $V_K$ CDR3 amino acid |
| 55 | 1F4 $V_H$ CDR1 amino acid |
| 56 | 1F4 $V_H$ CDR2 amino acid |
| 57 | 1F4 $V_H$ CDR3 amino acid |
| 58 | 1F4 $V_K$ CDR1 amino acid |
| 59 | 1F4 $V_K$ CDR2 amino acid |
| 60 | 1F4 $V_K$ CDR3 amino acid |

What is claimed is:

1. A method for treating a cancer in a subject suffering from such cancer, comprising administering to the subject a therapeutically effective amount of an immunoconjugate having a structure according to formula (IIIa').

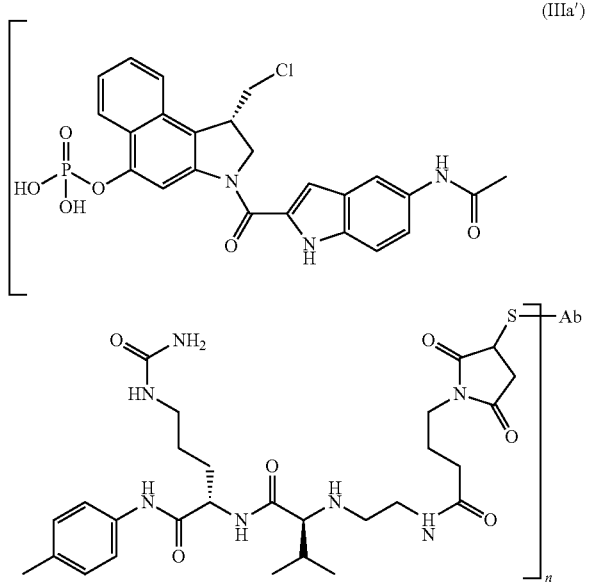

(IIIa')

wherein
n is 1, 2, 3, 4, or 5; and
Ab represents a human monoclonal antibody that recognizes a human antigen selected from the group consisting of CD70, mesothelin, PSMA, CD19, glypican-3, and CD22;
or a pharmaceutically acceptable salt thereof;
and wherein the cancer is renal cancer, pancreatic cancer, ovarian cancer, lymphoma, colon cancer, mesothelioma, gastric cancer, lung cancer, prostate cancer, adenocarcinoma, liver cancer, or breast cancer.

2. A method according to claim 1, wherein the cancer comprises cancer cells that express human CD70, mesothelin, PSMA, CD19, glypican-3, or CD22.

3. A method according to claim 1, wherein the human antigen is CD70.

4. A method according to claim 1, wherein the human antigen is mesothelin.

5. A method according to claim 1, wherein the human antigen is PSMA.

6. A method according to claim 1, wherein the human antigen is CD19.

7. A method according to claim 1, wherein the human antigen is glypican-3.

8. A method according to claim 1, wherein the human antigen is CD22.

9. A method according to claim 1, wherein the cancer is renal cancer.

10. A method according to claim 1, wherein the cancer is pancreatic cancer.

11. A method according to claim 1, wherein the cancer is ovarian cancer.

12. A method according to claim 1, wherein the cancer is lymphoma.

13. A method according to claim 1, wherein the cancer is colon cancer.

14. A method according to claim 1, wherein the cancer is mesothelioma.

15. A method according to claim 1, wherein the cancer is gastric cancer.

16. A method according to claim 1, wherein the cancer is lung cancer.

17. A method according to claim 1, wherein the cancer is prostate cancer.

18. A method according to claim 1, wherein the cancer is adenocarcinoma.

19. A method according to claim 1, wherein the cancer is liver cancer.

20. A method according to claim 1, wherein the cancer is breast cancer.

* * * * *